United States Patent
Komanduri et al.

(10) Patent No.: US 11,656,462 B2
(45) Date of Patent: May 23, 2023

(54) ADAPTIVE LENS ASSEMBLIES INCLUDING POLARIZATION-SELECTIVE LENS STACKS FOR AUGMENTED REALITY DISPLAY

(71) Applicant: Magic Leap, Inc., Plantation, FL (US)

(72) Inventors: Ravi Kumar Komanduri, Austin, TX (US); Chulwoo Oh, Cedar Park, TX (US)

(73) Assignee: MAGIC LEAP, INC., Plantation, FL (US)

( * ) Notice: Subject to any disclaimer, the term of this patent is extended or adjusted under 35 U.S.C. 154(b) by 224 days.

(21) Appl. No.: 16/978,165

(22) PCT Filed: Mar. 5, 2019

(86) PCT No.: PCT/US2019/020823
§ 371 (c)(1),
(2) Date: Sep. 3, 2020

(87) PCT Pub. No.: WO2019/173390
PCT Pub. Date: Sep. 12, 2019

(65) Prior Publication Data
US 2021/0041703 A1    Feb. 11, 2021

Related U.S. Application Data

(60) Provisional application No. 62/639,882, filed on Mar. 7, 2018.

(51) Int. Cl.
*G09G 5/00* (2006.01)
*G02B 27/01* (2006.01)
(Continued)

(52) U.S. Cl.
CPC ....... *G02B 27/0172* (2013.01); *C12Q 1/6844* (2013.01); *G06T 19/006* (2013.01); *G02F 1/13363* (2013.01); *G02F 1/133526* (2013.01)

(58) Field of Classification Search
CPC ........ G02B 27/0172; G02B 2027/0134; G02B 2027/0178; G02B 2027/0185; G02B 3/14;
(Continued)

(56) References Cited

U.S. PATENT DOCUMENTS

| | | |
|---|---|---|
| 4,904,063 A | 2/1990 | Okada et al. |
| 5,142,411 A | 8/1992 | Fiala |

(Continued)

FOREIGN PATENT DOCUMENTS

| | | |
|---|---|---|
| JP | 2002-156603 A | 5/2002 |
| WO | WO 2019/173390 | 9/2019 |

OTHER PUBLICATIONS

International Search Report and Written Opinion for PCT Application No. PCT/US2019/020823, dated May 16, 2019.
(Continued)

*Primary Examiner* — Thuy N Pardo
(74) *Attorney, Agent, or Firm* — Seed IP Law Group LLP

(57) ABSTRACT

The present disclosure relates to display systems and, more particularly, to augmented reality display systems. In one aspect, an adaptive lens assembly includes a lens stack configured to exert polarization-dependent optical power to linearly polarized light. The lens stack includes a birefringent lens and an isotropic lens contacting each other to form a conformal interface therebetween. The adaptive lens assembly is configured to be selectively switched between a plurality of states having different optical powers.

36 Claims, 31 Drawing Sheets

(51) Int. Cl.
*G06T 19/00* (2011.01)
*C12Q 1/6844* (2018.01)
*G02F 1/1335* (2006.01)
*G02F 1/13363* (2006.01)

(58) Field of Classification Search
CPC .... G02B 26/06; C12Q 1/6844; G06T 19/006;
G02F 1/133526; G02F 1/13363; G02F
1/133638; G02F 1/1396; G02F 1/294;
G02C 2202/20; G02C 7/12; G02C 7/083
USPC .................................................. 345/8, 5, 7
See application file for complete search history.

(56) References Cited

U.S. PATENT DOCUMENTS

| | | |
|---|---|---|
| 5,150,234 A | 9/1992 | Takahashi et al. |
| 6,850,221 B1 | 2/2005 | Tickle |
| 7,426,068 B2 | 9/2008 | Woodgate et al. |
| 9,417,452 B2 | 8/2016 | Schowengerdt et al. |
| 9,958,699 B2 | 5/2018 | Watson et al. |
| 10,042,038 B1 | 8/2018 | Lord |
| 2005/0232530 A1 | 10/2005 | Kekas |
| 2006/0028436 A1 | 2/2006 | Armstrong |
| 2007/0081123 A1 | 4/2007 | Lewis |
| 2008/0106806 A1 | 5/2008 | Hendriks et al. |
| 2012/0127062 A1 | 5/2012 | Bar-Zeev et al. |
| 2012/0147038 A1 | 6/2012 | Perez et al. |
| 2012/0162549 A1 | 6/2012 | Gao et al. |
| 2012/0274892 A1 | 11/2012 | Bonnin et al. |
| 2013/0082922 A1 | 4/2013 | Miller |
| 2013/0117377 A1 | 5/2013 | Miller |
| 2013/0125027 A1 | 5/2013 | Abovitz |
| 2013/0208234 A1 | 8/2013 | Lewis |
| 2013/0242262 A1 | 9/2013 | Lewis |
| 2014/0071539 A1 | 3/2014 | Gao |
| 2014/0177023 A1 | 6/2014 | Gao et al. |
| 2014/0218468 A1 | 8/2014 | Gao et al. |
| 2014/0267420 A1 | 9/2014 | Schowengerdt |
| 2015/0016777 A1 | 1/2015 | Abovitz et al. |
| 2015/0103306 A1 | 4/2015 | Kaji et al. |
| 2015/0178939 A1 | 6/2015 | Bradski et al. |
| 2015/0205126 A1 | 7/2015 | Schowengerdt |
| 2015/0302652 A1 | 10/2015 | Miller et al. |
| 2015/0309263 A2 | 10/2015 | Abovitz et al. |
| 2015/0326570 A1 | 11/2015 | Publicover et al. |
| 2015/0346495 A1 | 12/2015 | Welch et al. |
| 2016/0011419 A1 | 1/2016 | Gao |
| 2016/0026253 A1 | 1/2016 | Bradski et al. |
| 2016/0033698 A1 | 2/2016 | Escuti et al. |
| 2016/0139402 A1 | 5/2016 | Lapstun |
| 2016/0377867 A1 | 12/2016 | Kessler |
| 2017/0097449 A1 | 4/2017 | Ouderkirk et al. |
| 2017/0373459 A1 | 12/2017 | Weng et al. |
| 2018/0074331 A1* | 3/2018 | Ouderkirk ............ G02B 27/142 |
| 2018/0275410 A1* | 9/2018 | Yeoh ...................... G06F 3/013 |
| 2018/0356639 A1* | 12/2018 | Schaefer .............. G02B 27/017 |
| 2020/0012090 A1* | 1/2020 | Lapstun ............... H04N 13/229 |
| 2020/0159025 A1* | 5/2020 | Ouderkirk ................ G02B 5/28 |
| 2021/0199879 A1* | 7/2021 | Robinson .......... G02F 1/133536 |
| 2022/0026733 A1* | 1/2022 | Karafin ............... H04N 13/344 |
| 2022/0137418 A1* | 5/2022 | Schaefer .................. G02F 1/29 359/259 |
| 2022/0146888 A1* | 5/2022 | Oh ........................ G02F 1/1337 |

OTHER PUBLICATIONS

International Preliminary Report for Patentability for PCT Application No. PCT/US2019/020823, dated Sep. 8, 2020.

ARToolKit: https://web.archive.org/web/20051013062315/http://www.hitl.washington.edu:80/artoolkit/documentation/hardware.htm, archived Oct. 13, 2005.

Azuma, "a Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.

Azuma, "Predictive Tracking for Augmented Realty," TR95-007, Department of Computer Science, UNC-Chapel Hill, NC, Feb. 1995.

Bimber, et al., "Spatial Augmented Reality - Merging Real and Virtual Worlds," 2005 https://web.media.mit.edu/~raskar/book/BimberRaskarAugmentedRealityBook.pdf.

Jacob, "Eye Tracking in Advanced interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).

Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).

Extended European Search Report, dated Feb. 23, 2022, for European Application No. 19764481,8-1020, 13 pages.

* cited by examiner

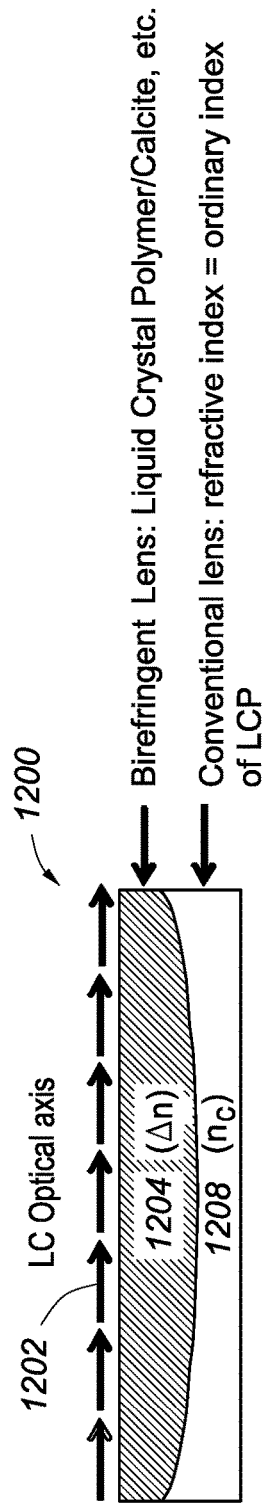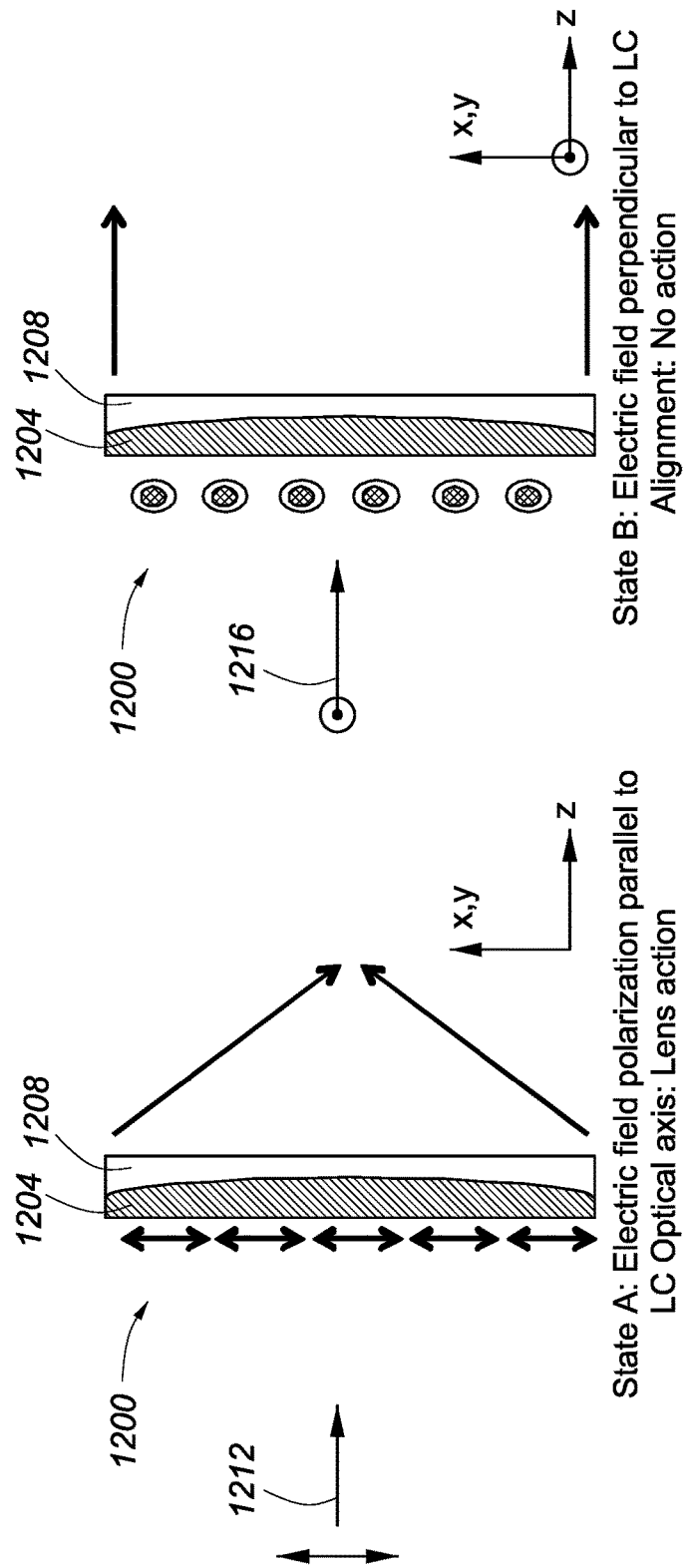
FIG. 12A
FIG. 12B
FIG. 12C

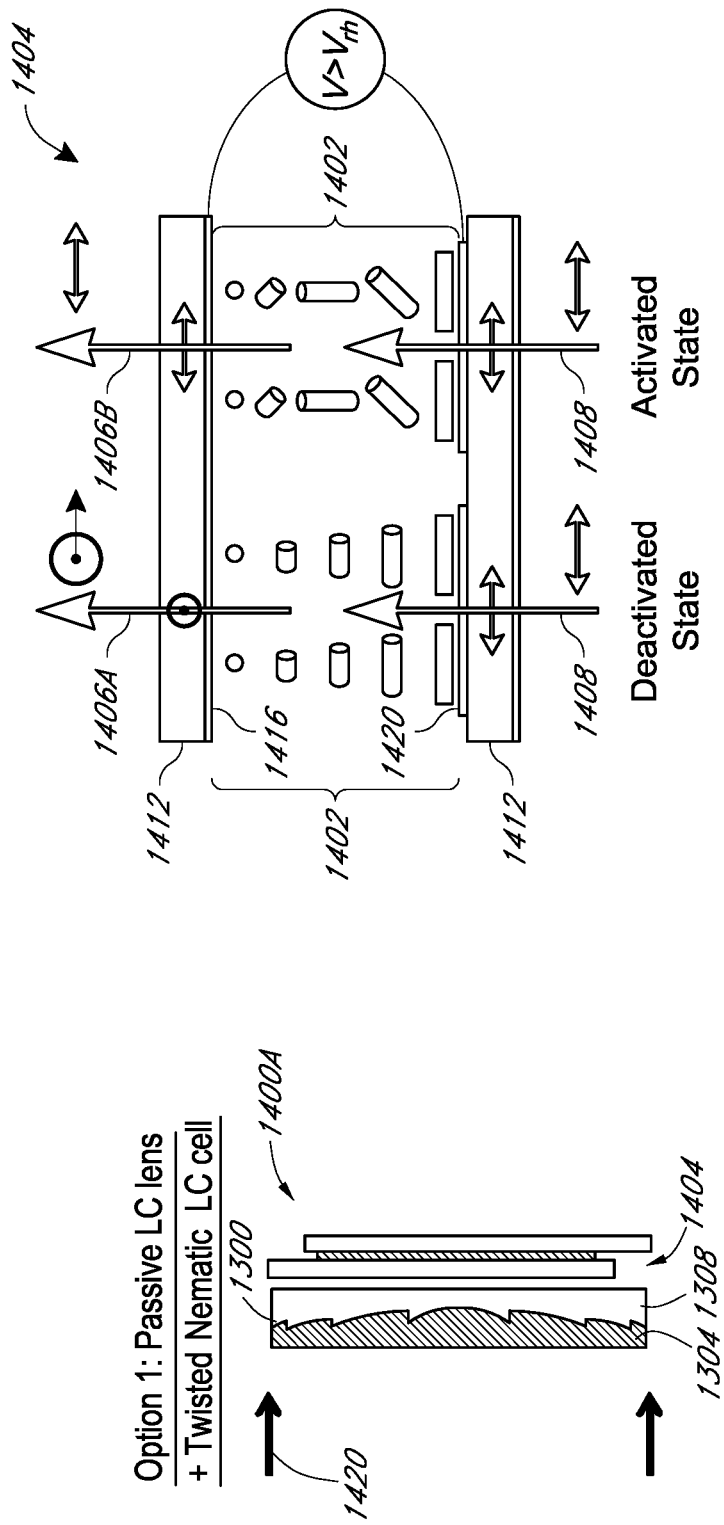

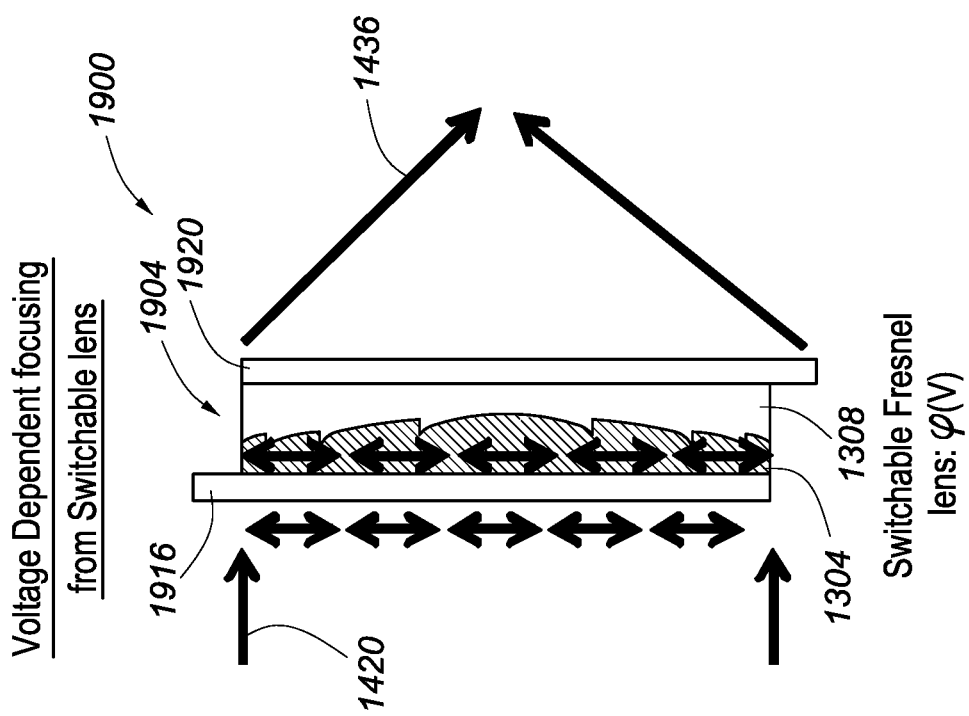

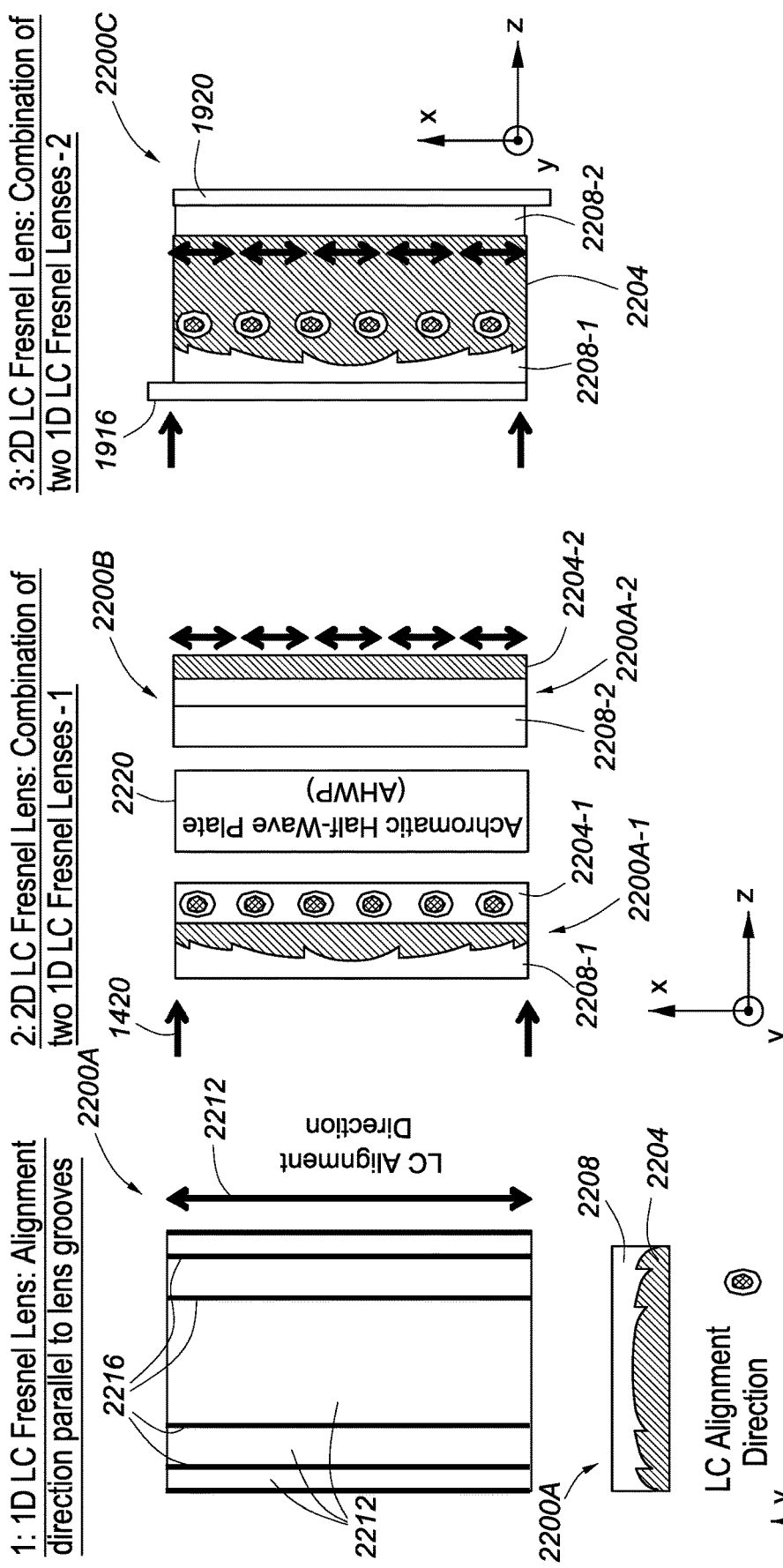

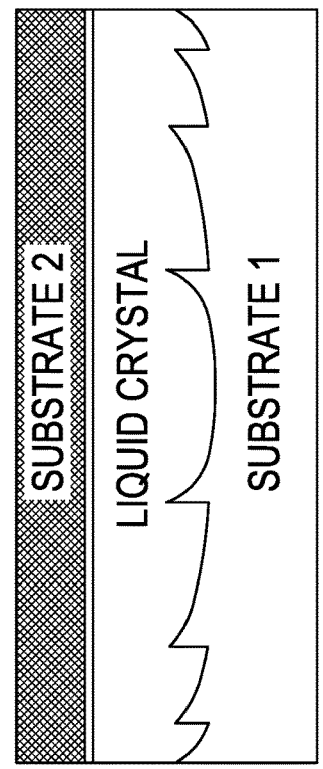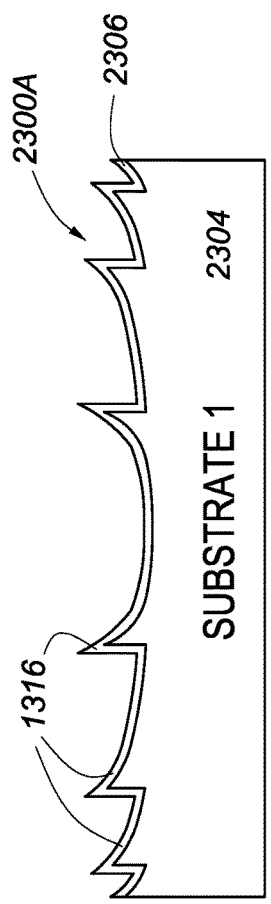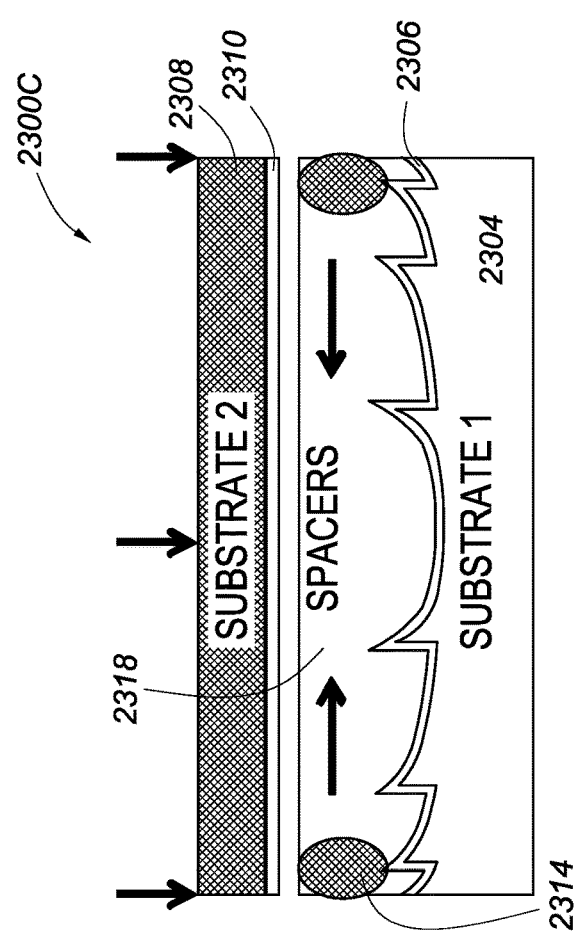
FIG. 22A
FIG. 22B
FIG. 22C
FIG. 22D

ADAPTIVE LENS ASSEMBLIES INCLUDING POLARIZATION-SELECTIVE LENS STACKS FOR AUGMENTED REALITY DISPLAY

CROSS-REFERENCE TO RELATED APPLICATIONS

This application claims the benefit of priority to U.S. Provisional Patent Application No. 62/639,882, filed Mar. 7, 2018, entitled "ADAPTIVE LENS ASSEMBLIES INCLUDING POLARIZATION-SELECTIVE LENS STACKS FOR AUGMENTED REALITY DISPLAY," the content of which is hereby incorporated by reference herein in its entirety.

INCORPORATION BY REFERENCE

This application incorporates by reference the entirety of each of the following patent applications: U.S. application Ser. No. 14/555,585 filed on Nov. 27, 2014, published on Jul. 23, 2015 as U.S. Publication No. 2015/0205126; U.S. application Ser. No. 14/690,401 filed on Apr. 18, 2015, published on Oct. 22, 2015 as U.S. Publication No. 2015/0302652; U.S. application Ser. No. 14/212,961 filed on Mar. 14, 2014, now U.S. Pat. No. 9,417,452 issued on Aug. 16, 2016; and U.S. application Ser. No. 14/331,218 filed on Jul. 14, 2014, published on Oct. 29, 2015 as U.S. Publication No. 2015/0309263.

BACKGROUND

Field

The present disclosure relates to display systems and, more particularly, to augmented and virtual reality display systems.

Description of the Related Art

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, in an MR scenario, AR image content may be blocked by or otherwise be perceived as interacting with objects in the real world.

Referring to FIG. 1, an augmented reality scene 10 is depicted wherein a user of an AR technology sees a real-world park-like setting 20 featuring people, trees, buildings in the background, and a concrete platform 30. In addition to these items, the user of the AR technology also perceives that he "sees" "virtual content" such as a robot statue 40 standing upon the real-world platform 30, and a cartoon-like avatar character 50 flying by which seems to be a personification of a bumble bee, even though these elements 40, 50 do not exist in the real world. Because the human visual perception system is complex, it is challenging to produce an AR technology that facilitates a comfortable, natural-feeling, rich presentation of virtual image elements amongst other virtual or real-world imagery elements.

Systems and methods disclosed herein address various challenges related to AR and VR technology.

SUMMARY

In a first aspect, an adaptive lens assembly includes a lens stack configured to exert polarization-dependent optical power to linearly polarized light. The lens stack includes a birefringent lens and an isotropic lens contacting each other to form a conformal interface therebetween. The adaptive lens assembly is configured to be selectively switched between a plurality of states having different optical powers.

In a second aspect, a display device includes a waveguide assembly configured to guide light in a lateral direction parallel to an output surface of the waveguide assembly. The waveguide assembly is further configured to outcouple the guided light through the output surface. The display device additionally includes an adaptive lens assembly disposed on a first side of the waveguide assembly. The adaptive lens assembly is disposed to receive outcoupled light from the waveguide assembly and to be selectively switched between a plurality of states having different optical powers. The adaptive lens assembly includes a lens stack configured to exert polarization-dependent optical power to linearly polarized light. The lens stack includes a birefringent lens and an isotropic lens contacting each other, wherein contacting surfaces of the birefringent lens and the isotropic lens form a conformal interface.

BRIEF DESCRIPTION OF THE DRAWINGS

FIG. 12A illustrates a cross-sectional view of an example polarization-selective lens stack comprising a birefringent lens and an isotropic lens.

FIG. 12B illustrates the polarization-selective lens stack of FIG. 12A in operation, passing therethrough linearly polarized light having a first polarization.

FIG. 12C illustrates the polarization-selective lens stack of FIG. 12A in operation, passing therethrough linearly polarized light having a second polarization.

FIG. 14A illustrates a cross-sectional view of an example adaptive lens assembly comprising a polarization-selective lens stack coupled with a switchable waveplate comprising twisted nematic liquid crystals.

FIG. 14B illustrates the switchable waveplate comprising twisted nematic liquid crystals of the adaptive lens assembly illustrated in FIG. 14A.

FIG. 18 illustrates a cross-sectional view of an example switchable polarization-selective lens stack comprising a birefringent Fresnel lens and an isotropic lens.

FIG. 21A illustrates a plan-view and a cross-sectional view of an example one-dimensional (1D) Fresnel lens stack.

FIG. 21B illustrates a cross-sectional view of an example two-dimensional (2D) Fresnel lens stack.

FIG. 21C illustrates a cross-sectional view of an example two-dimensional (2D) Fresnel lens stack.

FIGS. 22A-22D illustrate intermediate structures at different stages of manufacturing an example polarization-selective lens stack comprising a Fresnel birefringent lens and an isotropic lens.

Figure 1:
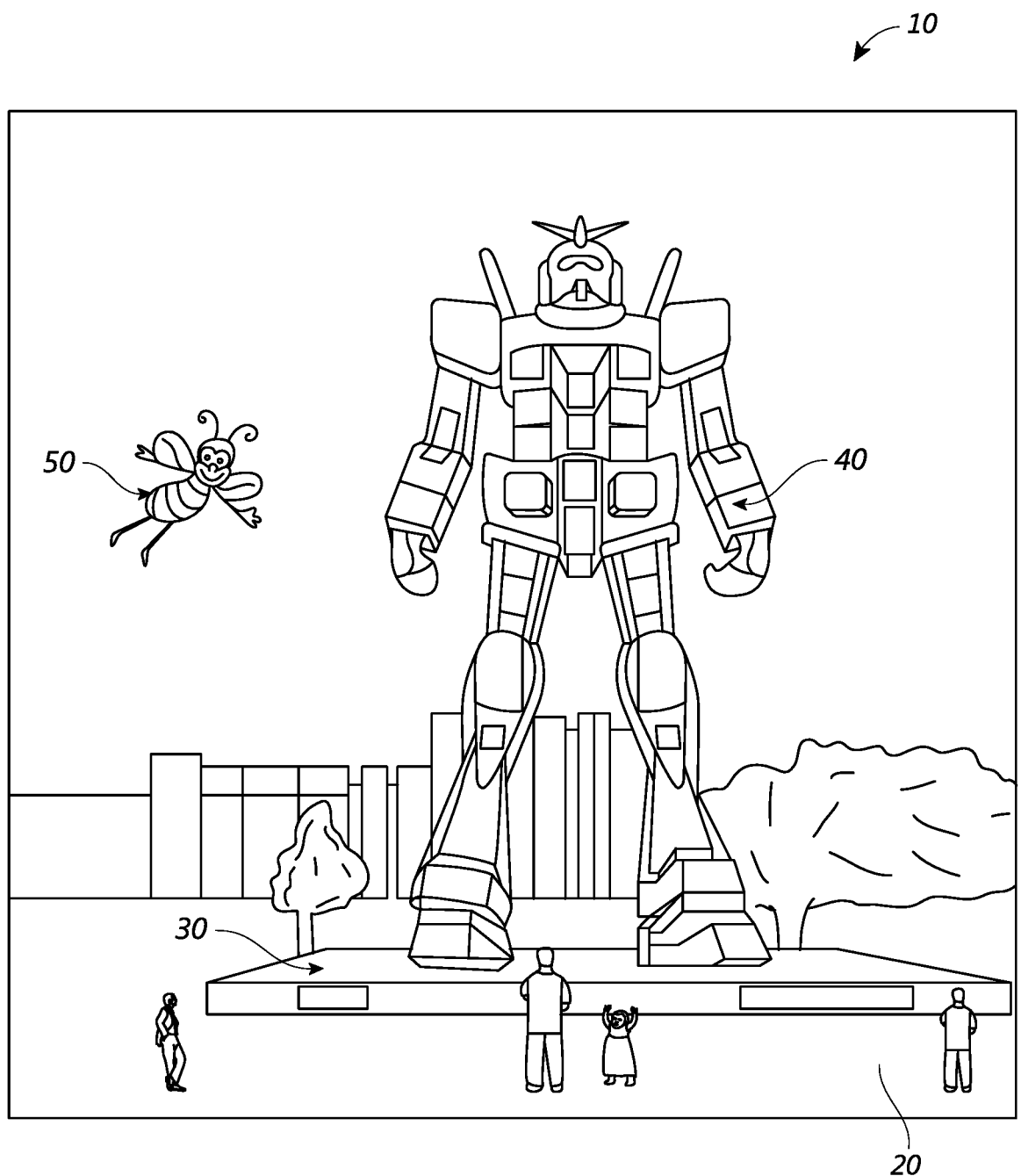
FIG. 1 illustrates a user's view of augmented reality (AR) through an AR device.

Throughout the drawings, reference numbers may be re-used to indicate correspondence between referenced elements. The drawings are provided to illustrate example embodiments described herein and are not intended to limit the scope of the disclosure.

DETAILED DESCRIPTION

AR systems may display virtual content to a user, or viewer, while still allowing the user to see the world around them. Preferably, this content is displayed on a head-mounted display, e.g., as part of eyewear, that projects image information to the user's eyes. In addition, the display may also transmit light from the surrounding environment to the user's eyes, to allow a view of that surrounding environment. As used herein, it will be appreciated that a "head-mounted" or "head mountable" display is a display that may be mounted on the head of a viewer or user.

In some AR systems, a plurality of waveguides may be configured to form virtual images at a plurality of virtual depth planes (also referred to simply a "depth planes" herein). Different waveguides of the plurality of waveguides may have different optical powers and may be formed at different distances from the user's eye. The display systems may also include a plurality lenses that provide or additionally provide optical powers. The optical powers of the waveguides and/or the lenses may provide images at different virtual depth planes. Undesirably, each of the waveguides and lenses may increase the overall thickness, weight and cost of the display.

Advantageously, in various embodiments described herein, an adaptive lens assembly may be utilized to provide variable optical power to, e.g., modify the wavefront divergence of light propagating through the lens assembly to provide virtual depth planes at different perceived distances from a user. The adaptive lens assembly may include a polarization-selective lens stack comprising a birefringent lens and an isotropic lens contacting each other, wherein contacting surfaces of the birefringent lens and the isotropic lens form a conformal interface. The birefringent lens has an optical axis and a birefringence ($\Delta n$) and is configured to exert a first optical power to light having a polarization direction parallel to the optical axis. The birefringent lens is also configured to exert a second optical power to light having a polarization direction perpendicular to the optical axis. The isotropic lens has a refractive index and configured to exert to light passing therethrough a third optical power opposite in sign as the first optical power and the second optical power. The adaptive lens assembly is configured to be selectively switched between a plurality of states having different optical powers. The polarization-selective lens stack is configured to exert an optical power proportional to the $\Delta n$ to light having a polarization direction parallel to the optical axis. The third optical power can be substantially the same or different in magnitude as the second optical power. When the third and second optical powers are substantially the same in magnitude, the polarization-selective lens stack is configured to exert substantially no optical power to light having a polarization direction perpendicular to the optical axis. When the third and second optical powers are substantially different in magnitude, the polarization-selective lens stack is configured to exert an optical power that may, e.g., be partially but not fully compensated to light having a polarization direction perpendicular to the optical axis. In some applications, e.g., when the user normally benefits from wearing corrective lenses such as prescription lenses or glasses, a partial compensation may be desirable for the polarization-selective lens stack to serve at least partially as corrective lenses. Thus, as configured, the polarization-selective lens stack is polarization-selective.

The adaptive lens assembly can be configured to be selectively switched between a plurality of states having different optical powers based on different configurations. In some embodiments, the adaptive lens assembly can be selectively switched by optically coupling a switchable half waveplate comprising twisted nematic (TN) liquid crystals (LCs) to the polarization-selective lens stack. In some embodiments, the birefringent lens comprises reactive mesogens, and the polarization-selective lens stack comprises electrodes configured to apply an electric field across the birefringent lens such that the polarization-selective lens stack can be electrically switchable between at least two optical power states.

In some embodiments, the adaptive lens assembly forms part of a display device with a waveguide assembly to form images at different virtual depth planes. In various embodiments, the display device comprises a pair of adaptive lens assemblies interposed by a waveguide assembly. The waveguide assembly includes a waveguide configured to propagate light (e.g., visible light) therein (e.g., via total internal reflection) and to outcouple the light. For example, the light may be outcoupled along an optical axis direction normal to a major surface of the waveguide. One of the pair of adaptive lens assemblies may be formed on a first side of the waveguide assembly and may be configured to provide variable optical power to modify the wavefront of light passing through the adaptive lens assembly to form images at each of a plurality of virtual depth planes. For example, the adaptive lens assemblies may converge or diverge outcoupled light received from the waveguide assembly. To compensate for modifications of real world views due to the convergence or divergence of ambient light propagating through the adaptive lens assembly and/or the waveguide assembly, the other of the pair of adaptive lens assemblies is additionally provided on a second side of the waveguide assembly opposite the first side. When the switchable waveplates of each adaptive lens assembly assume a corresponding state, the adaptive lens assemblies may have optical powers with opposite signs, such that the other of the adaptive lens assemblies correct for distortions caused by the adaptive lens assembly on the first side of the waveguide assembly.

Advantageously, relative to a continuously variable adaptive lens having continuously variable optical elements, utilizing a switchable waveplate that is switchable between two states simplifies the driving of the adaptive lens assembly and reduces the computational power needed to determine how to appropriately activate the adaptive lens assembly for a desired optical power. In addition, by allowing the adaptive lens assembly to modify the wavefront divergence of light outputted by a waveguide, the number waveguides needed to provide a plurality of depth planes is reduced relative to an arrangement in which each waveguide provides a particular amount of wavefront divergence.

Reference will now be made to the drawings, in which like reference numerals refer to like parts throughout. Unless indicated otherwise, the drawings are schematic not necessarily drawn to scale.

Example Display Systems

Figure 2:
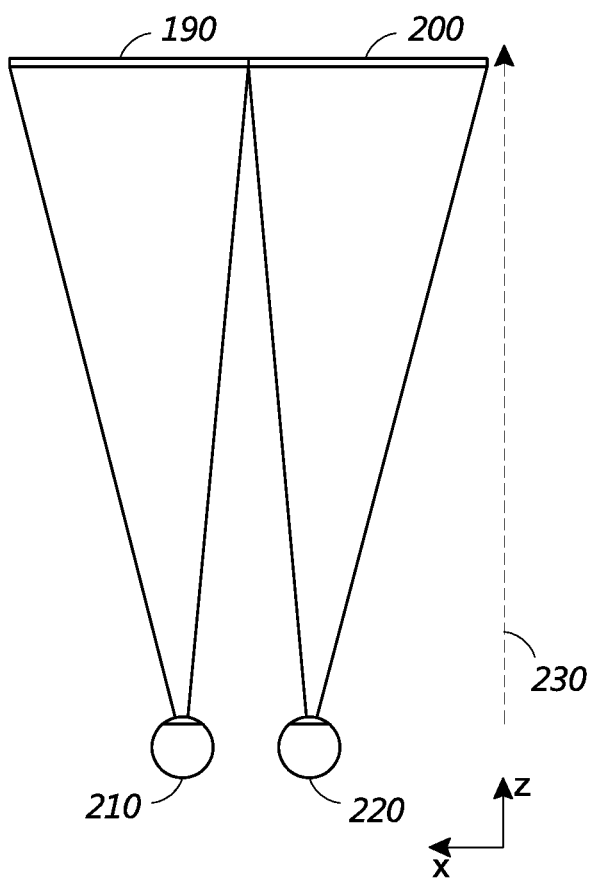
FIG. 2 illustrates a conventional display system for simulating three-dimensional imagery for a user.

FIG. 2 illustrates a conventional display system for simulating three-dimensional imagery for a user. It will be appreciated that a user's eyes are spaced apart and that, when looking at a real object in space, each eye will have a slightly different view of the object and may form an image of the object at different locations on the retina of each eye. This may be referred to as binocular disparity and may be utilized by the human visual system to provide a perception of depth. Conventional display systems simulate binocular disparity by presenting two distinct images 190, 200 with slightly different views of the same virtual object—one for each eye 210, 220—corresponding to the views of the virtual object that would be seen by each eye were the virtual object a real object at a desired depth. These images provide binocular cues that the user's visual system may interpret to derive a perception of depth.

With continued reference to FIG. 2, the images 190, 200 are spaced from the eyes 210, 220 by a distance 230 on a z-axis. The z-axis is parallel to the optical axis of the viewer with their eyes fixated on an object at optical infinity directly ahead of the viewer. The images 190, 200 are flat and at a fixed distance from the eyes 210, 220. Based on the slightly different views of a virtual object in the images presented to the eyes 210, 220, respectively, the eyes may naturally rotate such that an image of the object falls on corresponding points on the retinas of each of the eyes, to maintain single binocular vision. This rotation may cause the lines of sight of each of the eyes 210, 220 to converge onto a point in space at which the virtual object is perceived to be present. As a result, providing three-dimensional imagery conventionally involves providing binocular cues that may manipulate the vergence of the user's eyes 210, 220, and that the human visual system interprets to provide a perception of depth.

Figure 3A:
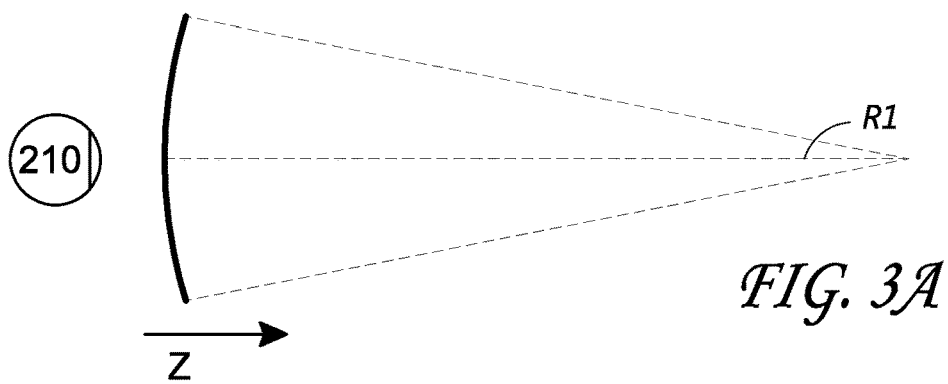
FIGS. 3A-3C illustrate relationships between radius of curvature and focal radius.
Figure 3B:
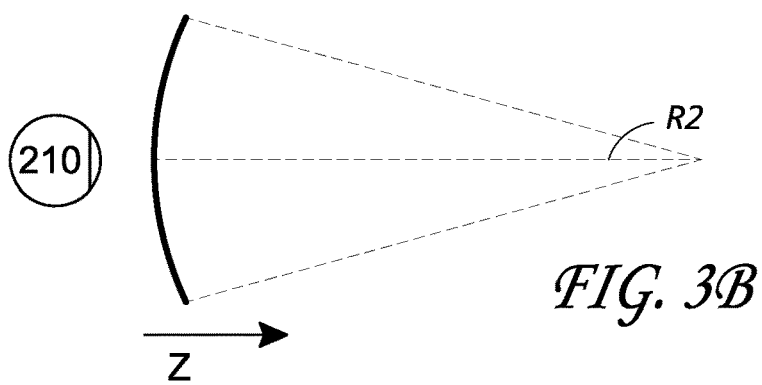
Figure 3C:
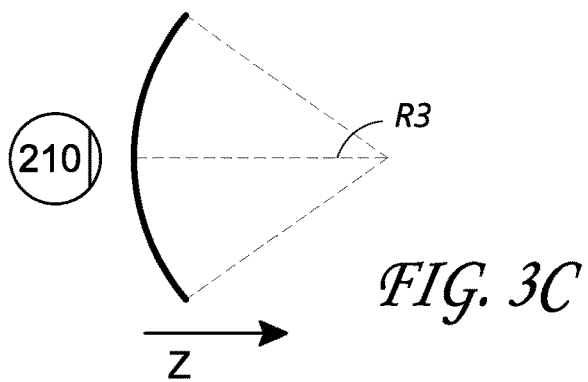

Generating a realistic and comfortable perception of depth is challenging, however. It will be appreciated that light from objects at different distances from the eyes have wavefronts with different amounts of divergence. FIGS. 3A-3C illustrate relationships between distance and the divergence of light rays. The distance between the object and the eye 210 is represented by, in order of decreasing distance, R1, R2, and R3. As shown in FIGS. 3A-3C, the light rays become more divergent as distance to the object decreases. Conversely, as distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 210. While only a single eye 210 is illustrated for clarity of illustration in FIGS. 3A-3C and other figures herein, the discussions regarding eye 210 may be applied to both eyes 210 and 220 of a viewer.

With continued reference to FIGS. 3A-3C, light from an object that the viewer's eyes are fixated on may have different degrees of wavefront divergence. Due to the different amounts of wavefront divergence, the light may be focused differently by the lens of the eye, which in turn may require the lens to assume different shapes to form a focused image on the retina of the eye. Where a focused image is not formed on the retina, the resulting retinal blur acts as a cue to accommodation that causes a change in the shape of the lens of the eye until a focused image is formed on the retina. For example, the cue to accommodation may trigger the ciliary muscles surrounding the lens of the eye to relax or contract, thereby modulating the force applied to the suspensory ligaments holding the lens, thus causing the shape of the lens of the eye to change until retinal blur of an object of fixation is eliminated or minimized, thereby forming a focused image of the object of fixation on the retina (e.g., fovea) of the eye. The process by which the lens of the eye changes shape may be referred to as accommodation, and the shape of the lens of the eye required to form a focused image of the object of fixation on the retina (e.g., fovea) of the eye may be referred to as an accommodative state.

Figure 4A:
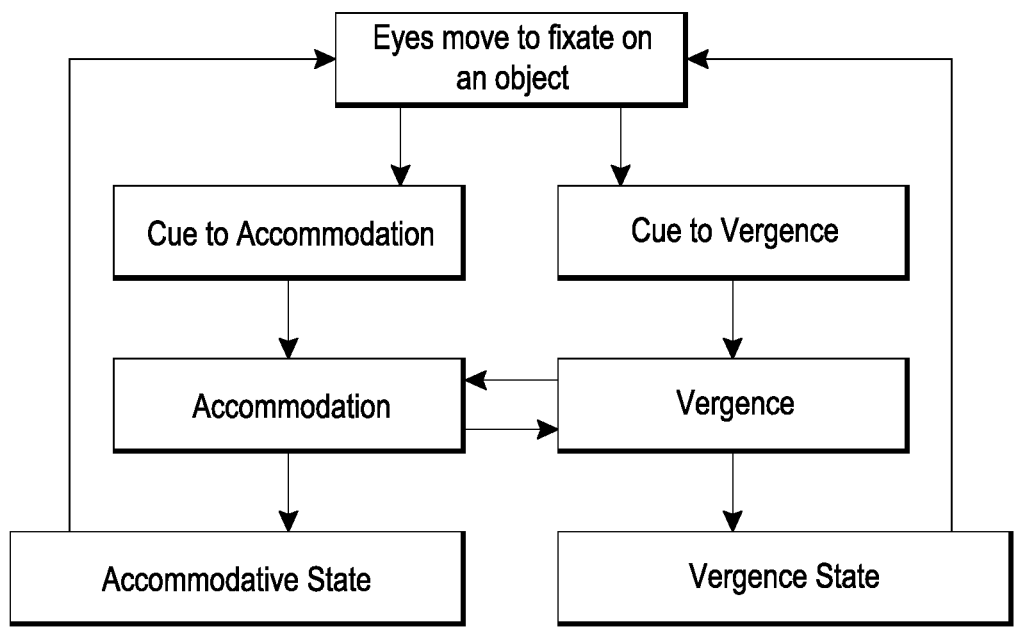
FIG. 4A illustrates a representation of the accommodation-vergence response of the human visual system.

With reference now to FIG. 4A, a representation of the accommodation-vergence response of the human visual system is illustrated. The movement of the eyes to fixate on an object causes the eyes to receive light from the object, with the light forming an image on each of the retinas of the eyes. The presence of retinal blur in the image formed on the retina may provide a cue to accommodation, and the relative locations of the image on the retinas may provide a cue to vergence. The cue to accommodation causes accommodation to occur, resulting in the lenses of the eyes each assuming a particular accommodative state that forms a focused image of the object on the retina (e.g., fovea) of the eye. On the other hand, the cue to vergence causes vergence movements (rotation of the eyes) to occur such that the images formed on each retina of each eye are at corresponding retinal points that maintain single binocular vision. In these positions, the eyes may be said to have assumed a particular vergence state. With continued reference to FIG. 4A, accommodation may be understood to be the process by which the eye achieves a particular accommodative state, and vergence may be understood to be the process by which the eye achieves a particular vergence state. As indicated in FIG. 4A, the accommodative and vergence states of the eyes may change if the user fixates on another object. For example, the accommodated state may change if the user fixates on a new object at a different depth on the z-axis.

Without being limited by theory, it is believed that viewers of an object may perceive the object as being "three-dimensional" due to a combination of vergence and accommodation. As noted above, vergence movements (e.g., rotation of the eyes so that the pupils move toward or away from each other to converge the lines of sight of the eyes to fixate upon an object) of the two eyes relative to each other are closely associated with accommodation of the lenses of the eyes. Under normal conditions, changing the shapes of the lenses of the eyes to change focus from one object to another object at a different distance will automatically cause a matching change in vergence to the same distance, under a relationship known as the "accommodation-vergence reflex." Likewise, a change in vergence will trigger a matching change in lens shape under normal conditions.

Figure 4B:
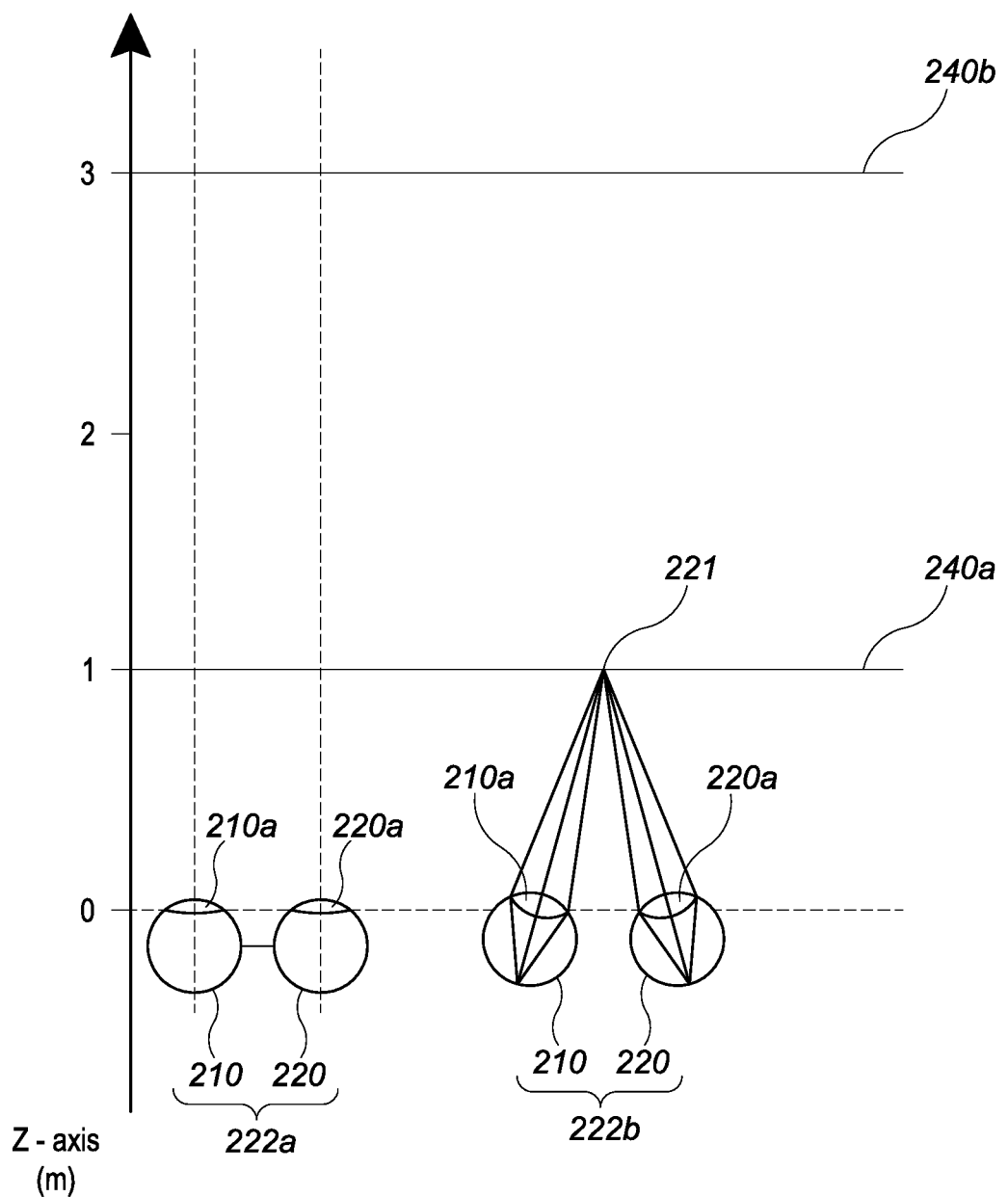
FIG. 4B illustrates examples of different accommodative states and vergence states of a pair of eyes of the user.

With reference now to FIG. 4B, examples of different accommodative and vergence states of the eyes are illustrated. The pair of eyes 222a is fixated on an object at optical infinity, while the pair eyes 222b are fixated on an object 221 at less than optical infinity. Notably, the vergence states of each pair of eyes is different, with the pair of eyes 222a directed straight ahead, while the pair of eyes 222 converge on the object 221. The accommodative states of the eyes forming each pair of eyes 222a and 222b are also different, as represented by the different shapes of the lenses 210a, 220a.

Undesirably, many users of conventional "3-D" display systems find such conventional systems to be uncomfortable or may not perceive a sense of depth at all due to a mismatch between accommodative and vergence states in these displays. As noted above, many stereoscopic or "3-D" display systems display a scene by providing slightly different images to each eye. Such systems are uncomfortable for many viewers, since they, among other things, simply provide different presentations of a scene and cause changes in the vergence states of the eyes, but without a corresponding change in the accommodative states of those eyes. Rather, the images are shown by a display at a fixed distance from the eyes, such that the eyes view all the image information at a single accommodative state. Such an arrangement works against the "accommodation-vergence reflex" by causing changes in the vergence state without a matching change in the accommodative state. This mismatch is believed to cause viewer discomfort. Display systems that provide a better match between accommodation and vergence may form more realistic and comfortable simulations of three-dimensional imagery.

Without being limited by theory, it is believed that the human eye typically may interpret a finite number of depth planes to provide depth perception. Consequently, a highly believable simulation of perceived depth may be achieved by providing, to the eye, different presentations of an image corresponding to each of these limited numbers of depth planes. In some embodiments, the different presentations may provide both cues to vergence and matching cues to accommodation, thereby providing physiologically correct accommodation-vergence matching.

With continued reference to FIG. 4B, two depth planes 240, corresponding to different distances in space from the eyes 210, 220, are illustrated. For a given depth plane 240, vergence cues may be provided by the displaying of images of appropriately different perspectives for each eye 210, 220. In addition, for a given depth plane 240, light forming the images provided to each eye 210, 220 may have a wavefront divergence corresponding to a light field produced by a point at the distance of that depth plane 240.

In the illustrated embodiment, the distance, along the z-axis, of the depth plane 240 containing the point 221 is 1 m. As used herein, distances or depths along the z-axis may be measured with a zero-point located at the exit pupils of the user's eyes. Thus, a depth plane 240 located at a depth of 1 in corresponds to a distance of 1 m away from the exit pupils of the user's eyes, on the optical axis of those eyes with the eyes directed towards optical infinity. As an approximation, the depth or distance along the z-axis may be measured from the display in front of the user's eyes (e.g., from the surface of a waveguide), plus a value for the distance between the device and the exit pupils of the user's eyes. That value may be called the eye relief and corresponds to the distance between the exit pupil of the user's eye and the display worn by the user in front of the eye. In practice, the value for the eye relief may be a normalized value used generally for all viewers. For example, the eye relief may be assumed to be 20 mm and a depth plane that is at a depth of 1 m may be at a distance of 980 mm in front of the display.

Figure 4C:
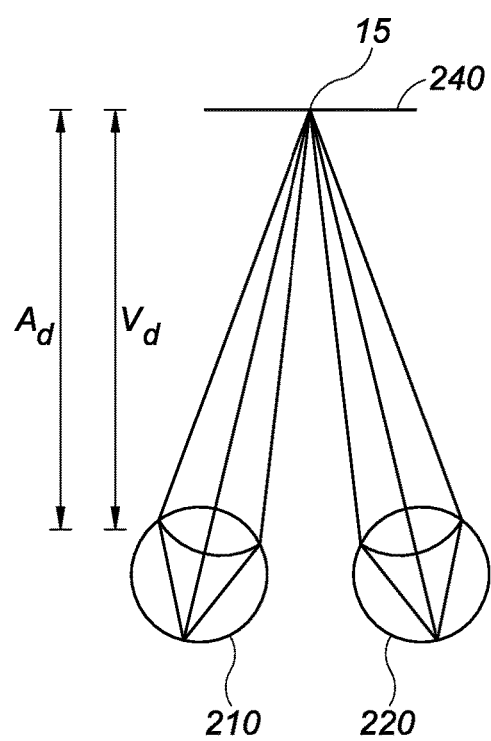
FIG. 4C illustrates an example of a representation of a top-down view of a user viewing content via a display system.
Figure 4D:
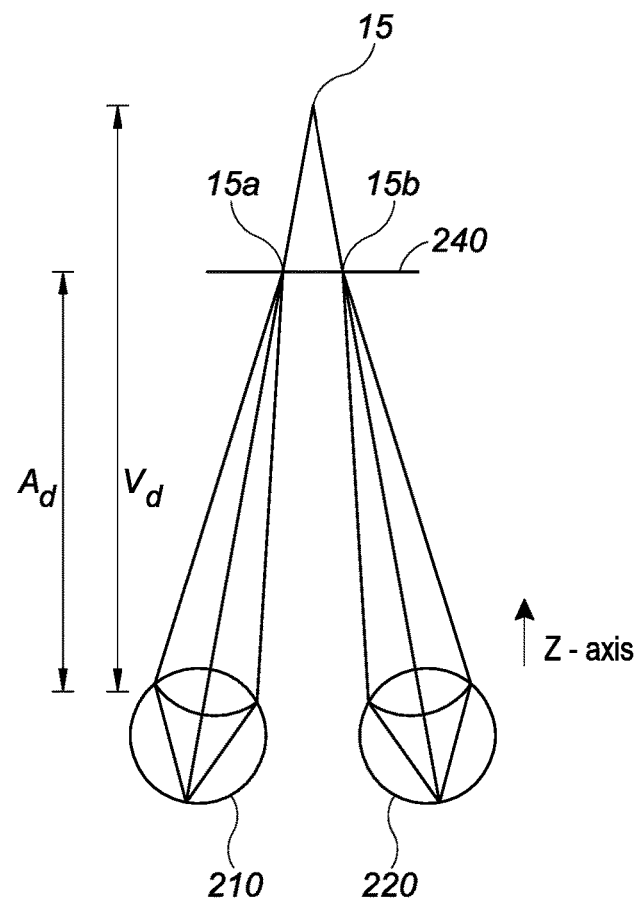
FIG. 4D illustrates another example of a representation of a top-down view of a user viewing content via a display system.

With reference now to FIGS. 4C and 4D, examples of matched accommodation-vergence distances and mismatched accommodation-vergence distances are illustrated, respectively. As illustrated in FIG. 4C, the display system may provide images of a virtual object to each eye 210, 220. The images may cause the eyes 210, 220 to assume a vergence state in which the eyes converge on a point 15 on a depth plane 240. In addition, the images may be formed by a light having a wavefront curvature corresponding to real objects at that depth plane 240. As a result, the eyes 210, 220 assume an accommodative state in which the images are in focus on the retinas of those eyes. Thus, the user may perceive the virtual object as being at the point 15 on the depth plane 240.

It will be appreciated that each of the accommodative and vergence states of the eyes 210, 220 are associated with a particular distance on the z-axis. For example, an object at a particular distance from the eyes 210, 220 causes those eyes to assume particular accommodative states based upon the distances of the object. The distance associated with a particular accommodative state may be referred to as the accommodation distance, $A_d$. Similarly, there are particular vergence distances, $V_d$, associated with the eyes in particular vergence states, or positions relative to one another. Where the accommodation distance and the vergence distance match, the relationship between accommodation and vergence may be said to be physiologically correct. This is considered to be the most comfortable scenario for a viewer.

In stereoscopic displays, however, the accommodation distance and the vergence distance may not always match. For example, as illustrated in FIG. 4D, images displayed to the eyes 210, 220 may be displayed with wavefront divergence corresponding to depth plane 240, and the eyes 210, 220 may assume a particular accommodative state in which the points 15a, 15b on that depth plane are in focus. However, the images displayed to the eyes 210, 220 may provide cues for vergence that cause the eyes 210, 220 to converge on a point 15 that is not located on the depth plane 240. As a result, the accommodation distance corresponds to the distance from the exit pupils of the eyes 210, 220 to the depth plane 240, while the vergence distance corresponds to the larger distance from the exit pupils of the eyes 210, 220 to the point 15, in some embodiments. The accommodation distance is different from the vergence distance. Consequently, there is an accommodation-vergence mismatch. Such a mismatch is considered undesirable and may cause discomfort in the user. It will be appreciated that the mismatch corresponds to distance (e.g., $V_d$-$A_d$) and may be characterized using diopters.

In some embodiments, it will be appreciated that a reference point other than exit pupils of the eyes 210, 220 may be utilized for determining distance for determining accommodation-vergence mismatch, so long as the same reference point is utilized for the accommodation distance and the vergence distance. For example, the distances could be measured from the cornea to the depth plane, from the retina to the depth plane, from the eyepiece (e.g., a waveguide of the display device) to the depth plane, and so on.

Without being limited by theory, it is believed that users may still perceive accommodation-vergence mismatches of up to about 0.25 diopter, up to about 0.33 diopter, and up to about 0.5 diopter as being physiologically correct, without the mismatch itself causing significant discomfort. In some embodiments, display systems disclosed herein (e.g., the display system 250, FIG. 6) present images to the viewer having accommodation-vergence mismatch of about 0.5 diopter or less. In some other embodiments, the accommodation-vergence mismatch of the images provided by the display system is about 0.33 diopter or less. In yet other embodiments, the accommodation-vergence mismatch of the images provided by the display system is about 0.25 diopter or less, including about 0.1 diopter or less.

Figure 5:
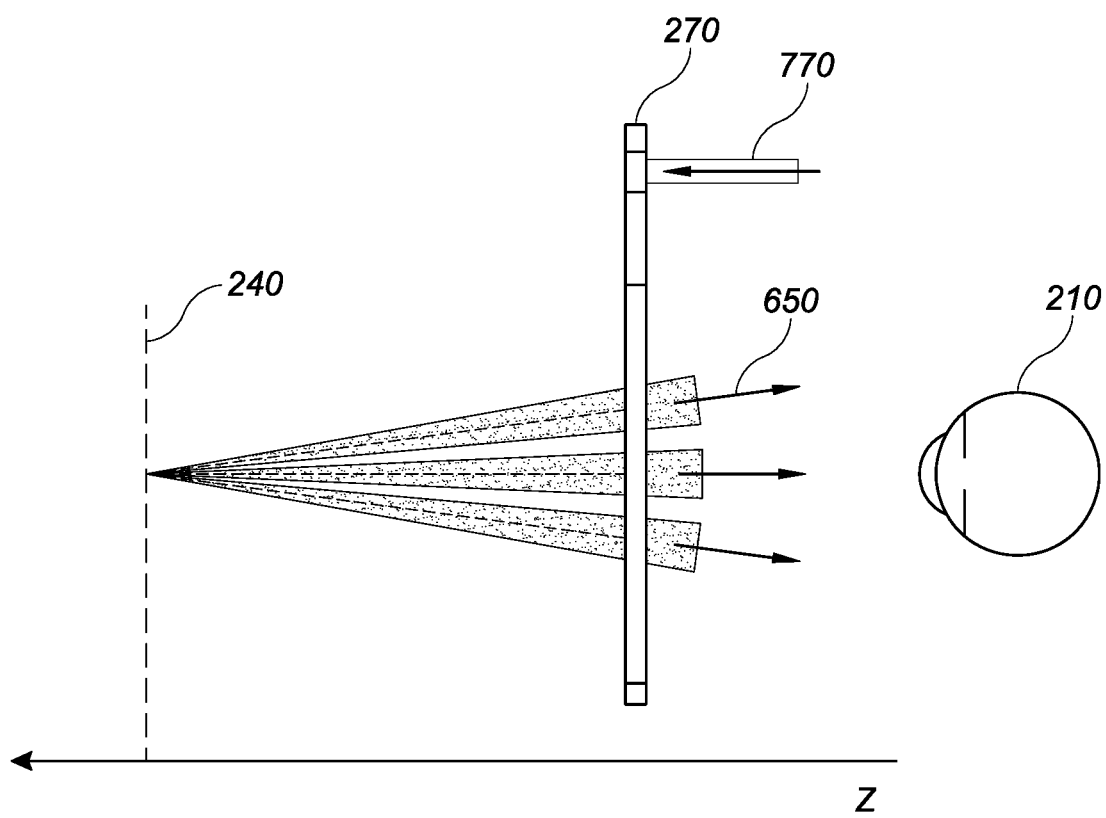
FIG. 5 illustrates aspects of an approach for simulating three-dimensional imagery by modifying wavefront divergence.

FIG. 5 illustrates aspects of an approach for simulating three-dimensional imagery by modifying wavefront divergence. The display system includes a waveguide 270 that is configured to receive light 770 that is encoded with image information, and to output that light to the user's eye 210. The waveguide 270 may output the light 650 with a defined amount of wavefront divergence corresponding to the wavefront divergence of a light field produced by a point on a desired depth plane 240. In some embodiments, the same amount of wavefront divergence is provided for all objects presented on that depth plane. In addition, it will be illustrated that the other eye of the user may be provided with image information from a similar waveguide.

In some embodiments, a single waveguide may be configured to output light with a set amount of wavefront divergence corresponding to a single or limited number of depth planes and/or the waveguide may be configured to output light of a limited range of wavelengths. Consequently, in some embodiments, a plurality or stack of waveguides may be utilized to provide different amounts of wavefront divergence for different depth planes and/or to output light of different ranges of wavelengths. As used herein, it will be appreciated at a depth plane may be planar or may follow the contours of a curved surface.

Figure 6:
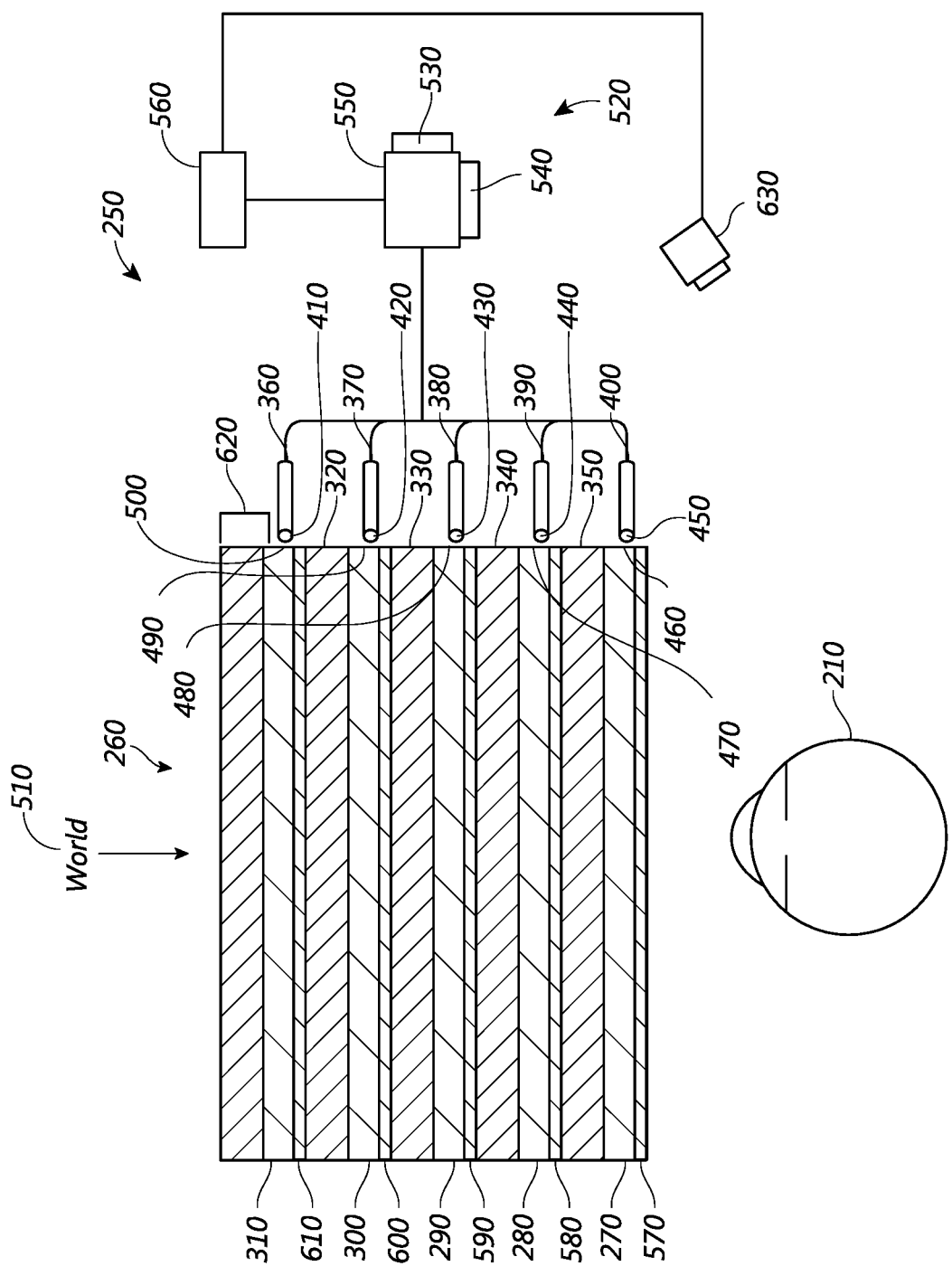
FIG. 6 illustrates an example of a waveguide stack for outputting image information to a user.

FIG. 6 illustrates an example of a waveguide stack for outputting image information to a user. A display system 250 includes a stack of waveguides, or stacked waveguide assembly, 260 that may be utilized to provide three-dimensional perception to the eye/brain using a plurality of waveguides 270, 280, 290, 300, 310. It will be appreciated that the display system 250 may be considered a light field display in some embodiments. In addition, the waveguide assembly 260 may also be referred to as an eyepiece.

In some embodiments, the display system 250 may be configured to provide substantially continuous cues to vergence and multiple discrete cues to accommodation. The cues to vergence may be provided by displaying different images to each of the eyes of the user, and the cues to accommodation may be provided by outputting the light that forms the images with selectable discrete amounts of wavefront divergence. Stated another way, the display system 250 may be configured to output light with variable levels of wavefront divergence. In some embodiments, each discrete level of wavefront divergence corresponds to a particular depth plane and may be provided by a particular one of the waveguides 270, 280, 290, 300, 310.

With continued reference to FIG. 6, the waveguide assembly 260 may also include a plurality of features 320, 330, 340, 350 between the waveguides. In some embodiments, the features 320, 330, 340, 350 may be one or more lenses. The waveguides 270, 280, 290, 300, 310 and/or the plurality of lenses 320, 330, 340, 350 may be configured to send image information to the eye with various levels of wavefront curvature or light ray divergence. Each waveguide level may be associated with a particular depth plane and may be configured to output image information corresponding to that depth plane. Image injection devices 360, 370, 380, 390, 400 may function as a source of light for the waveguides and may be utilized to inject image information into the waveguides 270, 280, 290, 300, 310, each of which may be configured, as described herein, to distribute incoming light across each respective waveguide, for output toward the eye 210. Light exits an output surface 410, 420, 430, 440, 450 of the image injection devices 360, 370, 380, 390, 400 and is injected into a corresponding input surface 460, 470, 480, 490, 500 of the waveguides 270, 280, 290, 300, 310. In some embodiments, each of the input surfaces 460, 470, 480, 490, 500 may be an edge of a corresponding waveguide, or may be part of a major surface of the corresponding waveguide (that is, one of the waveguide surfaces directly facing the world 510 or the viewer's eye 210). In some embodiments, a single beam of light (e.g. a collimated beam) may be injected into each waveguide to output an entire field of cloned collimated beams that are directed toward the eye 210 at particular angles (and amounts of divergence) corresponding to the depth plane associated with a particular waveguide. In some embodiments, a single one of the image injection devices 360, 370, 380, 390, 400 may be associated with and inject light into a plurality (e.g., three) of the waveguides 270, 280, 290, 300, 310.

In some embodiments, the image injection devices 360, 370, 380, 390, 400 are discrete displays that each produce image information for injection into a corresponding waveguide 270, 280, 290, 300, 310, respectively. In some other embodiments, the image injection devices 360, 370, 380, 390, 400 are the output ends of a single multiplexed display which may, e.g., pipe image information via one or more optical conduits (such as fiber optic cables) to each of the image injection devices 360, 370, 380, 390, 400. It will be appreciated that the image information provided by the image injection devices 360, 370, 380, 390, 400 may include light of different wavelengths, or colors (e.g., different component colors, as discussed herein).

In some embodiments, the light injected into the waveguides 270, 280, 290, 300, 310 is provided by a light projector system 520, which comprises a light module 530, which may include a light emitter, such as a light emitting diode (LED). The light from the light module 530 may be directed to and modified by a light modulator 540, e.g., a spatial light modulator, via a beam splitter 550. The light modulator 540 may be configured to change the perceived intensity of the light injected into the waveguides 270, 280, 290, 300, 310 to encode the light with image information. Examples of spatial light modulators include liquid crystal displays (LCD) including a liquid crystal on silicon (LCOS) displays. It will be appreciated that the image injection devices 360, 370, 380, 390, 400 are illustrated schematically and, in some embodiments, these image injection devices may represent different light paths and locations in a common projection system configured to output light into associated ones of the waveguides 270, 280, 290, 300, 310. In some embodiments, the waveguides of the waveguide assembly 260 may function as ideal lens while relaying light injected into the waveguides out to the user's eyes. In this conception, the object may be the spatial light modulator 540 and the image may be the image on the depth plane.

In some embodiments, the display system 250 may be a scanning fiber display comprising one or more scanning fibers configured to project light in various patterns (e.g., raster scan, spiral scan, Lissajous patterns, etc.) into one or more waveguides 270, 280, 290, 300, 310 and ultimately to the eye 210 of the viewer. In some embodiments, the illustrated image injection devices 360, 370, 380, 390, 400 may schematically represent a single scanning fiber or a bundle of scanning fibers configured to inject light into one or a plurality of the waveguides 270, 280, 290, 300, 310. In some other embodiments, the illustrated image injection devices 360, 370, 380, 390, 400 may schematically represent a plurality of scanning fibers or a plurality of bundles of scanning fibers, each of which are configured to inject light into an associated one of the waveguides 270, 280, 290, 300, 310. It will be appreciated that one or more optical fibers may be configured to transmit light from the light module 530 to the one or more waveguides 270, 280, 290, 300, 310. It will be appreciated that one or more intervening optical structures may be provided between the scanning fiber, or fibers, and the one or more waveguides 270, 280, 290, 300, 310 to, e.g., redirect light exiting the scanning fiber into the one or more waveguides 270, 280, 290, 300, 310.

A controller 560 controls the operation of one or more of the stacked waveguide assembly 260, including operation of the image injection devices 360, 370, 380, 390, 400, the light source 530, and the light modulator 540. In some embodiments, the controller 560 is part of the local data processing module 140. The controller 560 includes programming (e.g., instructions in a non-transitory medium) that regulates the timing and provision of image information to the waveguides 270, 280, 290, 300, 310 according to, e.g., any of the various schemes disclosed herein. In some embodiments, the controller may be a single integral device, or a distributed system connected by wired or wireless communication channels. The controller 560 may be part of the processing modules 140 or 150 (FIG. 9D) in some embodiments.

With continued reference to FIG. 6, the waveguides 270, 280, 290, 300, 310 may be configured to propagate light within each respective waveguide by total internal reflection (TIR). The waveguides 270, 280, 290, 300, 310 may each be planar or have another shape (e.g., curved), with major top and bottom surfaces and edges extending between those major top and bottom surfaces. In the illustrated configuration, the waveguides 270, 280, 290, 300, 310 may each include out-coupling optical elements 570, 580, 590, 600, 610 that are configured to extract light out of a waveguide by redirecting the light, propagating within each respective waveguide, out of the waveguide to output image information to the eye 210. Extracted light may also be referred to as out-coupled light and the out-coupling optical elements light may also be referred to light extracting optical elements. An extracted beam of light may be outputted by the waveguide at locations at which the light propagating in the waveguide strikes a light extracting optical element. The out-coupling optical elements 570, 580, 590, 600, 610 may, for example, be gratings, including diffractive optical features, as discussed further herein. While illustrated disposed at the bottom major surfaces of the waveguides 270, 280, 290, 300, 310, for ease of description and drawing clarity, in some embodiments, the out-coupling optical elements 570, 580, 590, 600, 610 may be disposed at the top and/or bottom major surfaces, and/or may be disposed directly in the volume of the waveguides 270, 280, 290, 300, 310, as discussed further herein. In some embodiments, the out-coupling optical elements 570, 580, 590, 600, 610 may be formed in a layer of material that is attached to a transparent substrate to form the waveguides 270, 280, 290, 300, 310. In some other embodiments, the waveguides 270, 280, 290, 300, 310 may be a monolithic piece of material and the out-coupling optical elements 570, 580, 590, 600, 610 may be formed on a surface and/or in the interior of that piece of material.

With continued reference to FIG. 6, as discussed herein, each waveguide 270, 280, 290, 300, 310 is configured to output light to form an image corresponding to a particular depth plane. For example, the waveguide 270 nearest the eye may be configured to deliver collimated light (which was injected into such waveguide 270), to the eye 210. The collimated light may be representative of the optical infinity focal plane. The next waveguide up 280 may be configured to send out collimated light which passes through the first lens 350 (e.g., a negative lens) before it may reach the eye 210; such first lens 350 may be configured to create a slight convex wavefront curvature so that the eye/brain interprets light coming from that next waveguide up 280 as coming from a first focal plane closer inward toward the eye 210 from optical infinity. Similarly, the third up waveguide 290 passes its output light through both the first 350 and second 340 lenses before reaching the eye 210; the combined optical power of the first 350 and second 340 lenses may be configured to create another incremental amount of wavefront curvature so that the eye/brain interprets light coming from the third waveguide 290 as coming from a second focal plane that is even closer inward toward the person from optical infinity than was light from the next waveguide up 280.

The other waveguide layers 300, 310 and lenses 330, 320 are similarly configured, with the highest waveguide 310 in the stack sending its output through all of the lenses between it and the eye for an aggregate focal power representative of the closest focal plane to the person. To compensate for the stack of lenses 320, 330, 340, 350 when viewing/interpreting light coming from the world 510 on the other side of the stacked waveguide assembly 260, a compensating lens layer 620 may be disposed at the top of the stack to compensate for the aggregate power of the lens stack 320, 330, 340, 350 below. Such a configuration provides as many perceived focal planes as there are available waveguide/lens pairings. Both the out-coupling optical elements of the waveguides and the focusing aspects of the lenses may be static (i.e., not dynamic or electro-active). In some alternative embodiments, either or both may be dynamic using electro-active features.

In some embodiments, two or more of the waveguides 270, 280, 290, 300, 310 may have the same associated depth plane. For example, multiple waveguides 270, 280, 290, 300, 310 may be configured to output images set to the same depth plane, or multiple subsets of the waveguides 270, 280, 290, 300, 310 may be configured to output images set to the same plurality of depth planes, with one set for each depth plane. This may provide advantages for forming a tiled image to provide an expanded field of view at those depth planes.

With continued reference to FIG. 6, the out-coupling optical elements 570, 580, 590, 600, 610 may be configured to both redirect light out of their respective waveguides and to output this light with the appropriate amount of divergence or collimation for a particular depth plane associated with the waveguide. As a result, waveguides having different associated depth planes may have different configurations of out-coupling optical elements 570, 580, 590, 600, 610, which output light with a different amount of divergence depending on the associated depth plane. In some embodiments, the light extracting optical elements 570, 580, 590, 600, 610 may be volumetric or surface features, which may be configured to output light at specific angles. For example, the light extracting optical elements 570, 580, 590, 600, 610 may be volume holograms, surface holograms, and/or diffraction gratings. In some embodiments, the features 320, 330, 340, 350 may not be lenses; rather, they may simply be spacers (e.g., cladding layers and/or structures for forming air gaps).

In some embodiments, the out-coupling optical elements 570, 580, 590, 600, 610 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 210 with each intersection of the DOE, while the rest continues to move through a waveguide via TIR. The light carrying the image information is thus divided into a number of related exit beams that exit the waveguide at a multiplicity of locations and the result is a fairly uniform pattern of exit emission toward the eye 210 for this particular collimated beam bouncing around within a waveguide.

In some embodiments, one or more DOES may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 630 (e.g., a digital camera, including visible light and infrared light cameras) may be provided to capture images of the eye 210 and/or tissue around the eye 210 to, e.g., detect user inputs and/or to monitor the physiological state of the user. As used herein, a camera may be any image capture device. In some embodiments, the camera assembly 630 may include an image capture device and a light source to project light (e.g., infrared light) to the eye, which may then be reflected by the eye and detected by the image capture device. In some embodiments, the camera assembly 630 may be attached to the frame 80 (FIG. 9D) and may be in electrical communication with the processing modules 140 and/or 150, which may process image information from the camera assembly 630. In some embodiments, one camera assembly 630 may be utilized for each eye, to separately monitor each eye.

Figure 7:
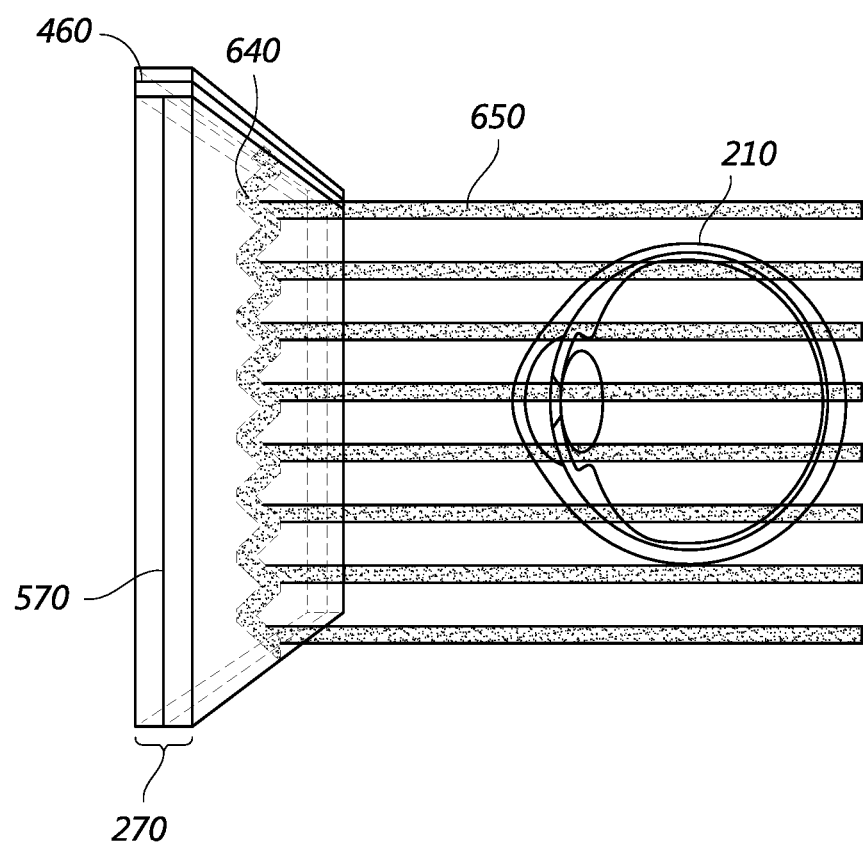
FIG. 7 illustrates an example of exit beams outputted by a waveguide.
Figure 8:
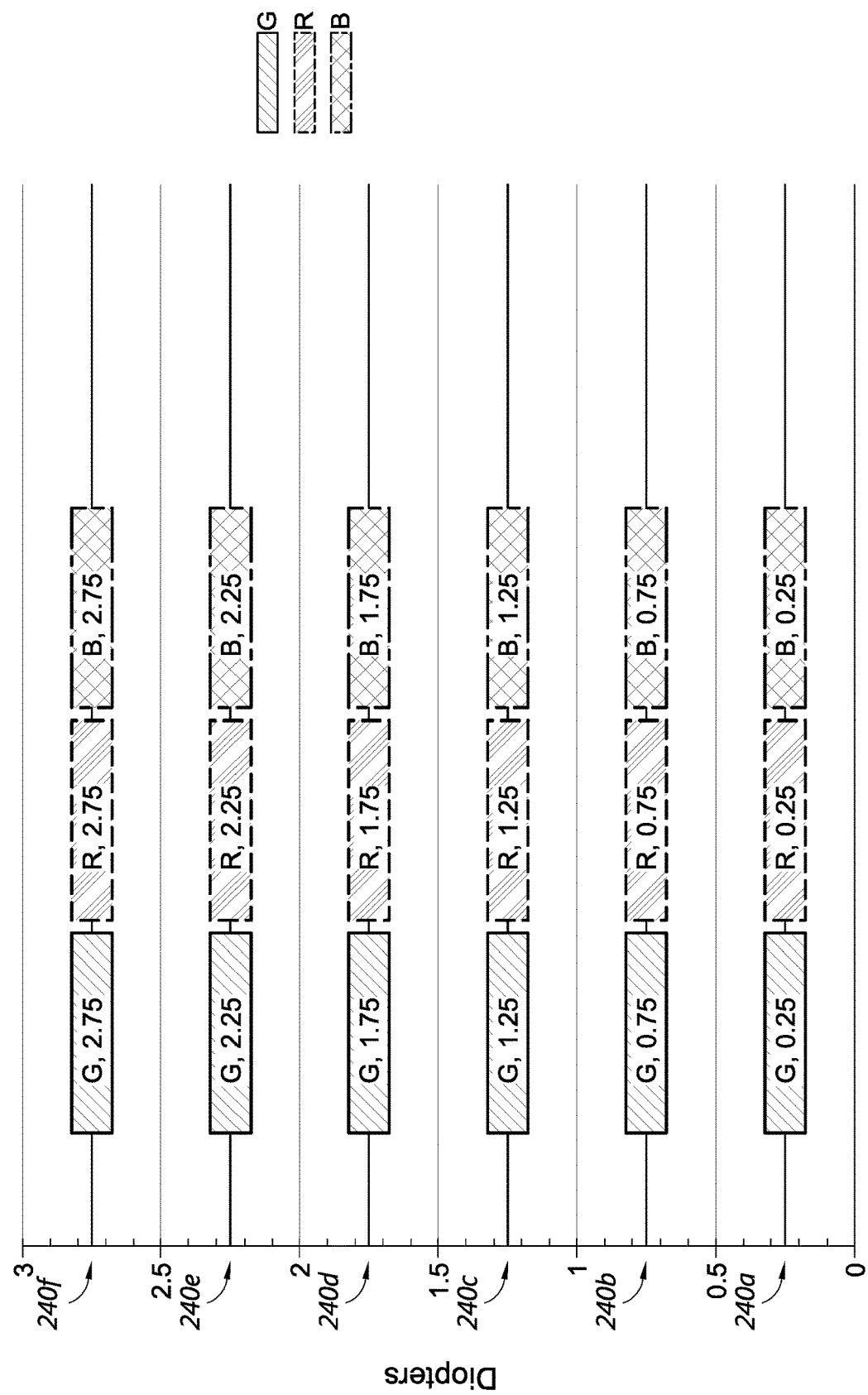
FIG. 8 illustrates an example of a stacked waveguide assembly in which each depth plane includes images formed using multiple different component colors.

With reference now to FIG. 7, an example of exit beams outputted by a waveguide is shown. One waveguide is illustrated, but it will be appreciated that other waveguides in the waveguide assembly 260 (FIG. 6) may function similarly, where the waveguide assembly 260 includes multiple waveguides. Light 640 is injected into the waveguide 270 at the input surface 460 of the waveguide 270 and propagates within the waveguide 270 by TIR. At points where the light 640 impinges on the DOE 570, a portion of the light exits the waveguide as exit beams 650. The exit beams 650 are illustrated as substantially parallel but, as discussed herein, they may also be redirected to propagate to the eye 210 at an angle (e.g., forming divergent exit beams), depending on the depth plane associated with the waveguide 270. It will be appreciated that substantially parallel exit beams may be indicative of a waveguide with out-coupling optical elements that out-couple light to form images that appear to be set on a depth plane at a large distance (e.g., optical infinity) from the eye 210. Other waveguides or other sets of out-coupling optical elements may output an exit beam pattern that is more divergent, which would require the eye 210 to accommodate to a closer distance to bring it into focus on the retina and would be interpreted by the brain as light from a distance closer to the eye 210 than optical infinity.

in some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 240a-240f, although more or fewer depths are also contemplated. Each depth plane may have three or more component color images associated with it, including: a first image of a first color, G; a second image of a second color, R; and a third image of a third color, B.

Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 530 (FIG. 6) may be configured to emit light of one or more wavelengths outside the visual perception range of the viewer, for example, infrared and/or ultraviolet wavelengths. In addition, the in-coupling, out-coupling, and other light redirecting structures of the waveguides of the display 250 may be configured to direct and emit this light out of the display towards the user's eye 210, e.g., for imaging and/or user stimulation applications.

Figure 9A:
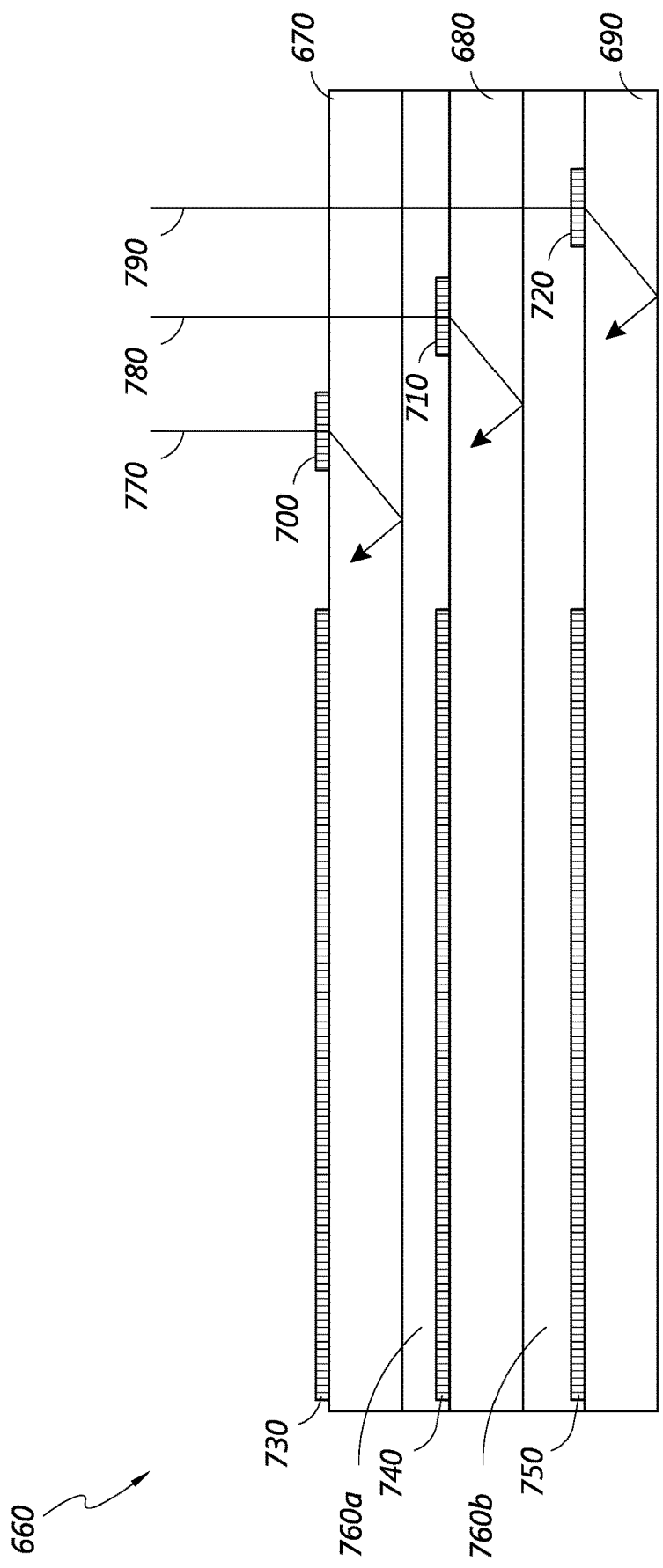
FIG. 9A illustrates a cross-sectional side view of an example of a set of stacked waveguides that each includes an incoupling optical element.

With reference now to FIG. 9A, in some embodiments, light impinging on a waveguide may need to be redirected to in-couple that light into the waveguide. An in-coupling optical element may be used to redirect and in-couple the light into its corresponding waveguide. FIG. 9A illustrates a cross-sectional side view of an example of a plurality or set 660 of stacked waveguides that each includes an in-coupling optical element. The waveguides may each be configured to output light of one or more different wavelengths, or one or more different ranges of wavelengths. It will be appreciated that the stack 660 may correspond to the stack 260 (FIG. 6) and the illustrated waveguides of the stack 660 may correspond to part of the plurality of waveguides 270, 280, 290, 300, 310, except that light from one or more of the image injection devices 360, 370, 380, 390, 400 is injected into the waveguides from a position that requires light to be redirected for in-coupling.

The illustrated set 660 of stacked waveguides includes waveguides 670, 680, and 690. Each waveguide includes an associated in-coupling optical element (which may also be referred to as a light input area on the waveguide), with, e.g., in-coupling optical element 700 disposed on a major surface (e.g., an upper major surface) of waveguide 670, in-coupling optical element 710 disposed on a major surface (e.g., an upper major surface) of waveguide 680, and in-coupling optical element 720 disposed on a major surface (e.g., an upper major surface) of waveguide 690. In some embodiments, one or more of the in-coupling optical elements 700, 710, 720 may be disposed on the bottom major surface of the respective waveguide 670, 680, 690 (particularly where the one or more in-coupling optical elements are reflective, deflecting optical elements). As illustrated, the in-coupling optical elements 700, 710, 720 may be disposed on the upper major surface of their respective waveguide 670, 680, 690 (or the top of the next lower waveguide), particularly where those in-coupling optical elements are transmissive, deflecting optical elements. In some embodiments, the in-coupling optical elements 700, 710, 720 may be disposed in the body of the respective waveguide 670, 680, 690. In some embodiments, as discussed herein, the in-coupling optical elements 700, 710, 720 are wavelength selective, such that they selectively redirect one or more wavelengths of light, while transmitting other wavelengths of light. While illustrated on one side or corner of their respective waveguide 670, 680, 690, it will be appreciated that the in-coupling optical elements 700, 710, 720 may be disposed in other areas of their respective waveguide 670, 680, 690 in some embodiments.

As illustrated, the in-coupling optical elements 700, 710, 720 may be laterally offset from one another. In some embodiments, each in-coupling optical element may be offset such that it receives light without that light passing through another in-coupling optical element. For example, each in-coupling optical element 700, 710, 720 may be configured to receive light from a different image injection device 360, 370, 380, 390, and 400 as shown in FIG. 6, and may be separated (e.g., laterally spaced apart) from other in-coupling optical elements 700, 710, 720 such that it substantially does not receive light from the other ones of the in-coupling optical elements 700, 710, 720.

Each waveguide also includes associated light distributing elements, with, e.g., light distributing elements 730 disposed on a major surface (e.g., a top major surface) of waveguide 670, light distributing elements 740 disposed on a major surface (e.g., a top major surface) of waveguide 680, and light distributing elements 750 disposed on a major surface (e.g., a top major surface) of waveguide 690. In some other embodiments, the light distributing elements 730, 740, 750, may be disposed on a bottom major surface of associated waveguides 670, 680, 690, respectively. In some other embodiments, the light distributing elements 730, 740, 750, may be disposed on both top and bottom major surface of associated waveguides 670, 680, 690, respectively; or the light distributing elements 730, 740, 750, may be disposed on different ones of the top and bottom major surfaces in different associated waveguides 670, 680, 690, respectively.

The waveguides 670, 680, 690 may be spaced apart and separated by, e.g., gas, liquid, and/or solid layers of material.

For example, as illustrated, layer 760a may separate waveguides 670 and 680; and layer 760b may separate waveguides 680 and 690. In some embodiments, the layers 760a and 760b are formed of low refractive index materials (that is, materials having a lower refractive index than the material forming the immediately adjacent one of waveguides 670, 680, 690). Preferably, the refractive index of the material forming the layers 760a, 760b is 0.05 or more, or 0.10 or less than the refractive index of the material forming the waveguides 670, 680, 690. Advantageously, the lower refractive index layers 760a, 760b may function as cladding layers that facilitate total internal reflection (TER) of light through the waveguides 670, 680, 690 (e.g., TIR between the top and bottom major surfaces of each waveguide). In some embodiments, the layers 760a, 760b are formed of air. While not illustrated, it will be appreciated that the top and bottom of the illustrated set 660 of waveguides may include immediately neighboring cladding layers.

Preferably, for ease of manufacturing and other considerations, the material forming the waveguides 670, 680, 690 are similar or the same, and the material forming the layers 760a, 760b are similar or the same. In some embodiments, the material forming the waveguides 670, 680, 690 may be different between one or more waveguides, and/or the material forming the layers 760a, 760b may be different, while still holding to the various refractive index relationships noted above.

With continued reference to FIG. 9A, light rays 770, 780, 790 are incident on the set 660 of waveguides. It will be appreciated that the light rays 770, 780, 790 may be injected into the waveguides 670, 680, 690 by one or more image injection devices 360, 370, 380, 390, 400 (FIG. 6).

In some embodiments, the light rays 770, 780, 790 have different properties, e.g., different wavelengths or different ranges of wavelengths, which may correspond to different colors. The in-coupling optical elements 700, 710, 720 each deflect the incident light such that the light propagates through a respective one of the waveguides 670, 680, 690 by TR. In some embodiments, the incoupling optical elements 700, 710, 720 each selectively deflect one or more particular wavelengths of light, while transmitting other wavelengths to an underlying waveguide and associated incoupling optical element.

For example, in-coupling optical element 700 may be configured to deflect ray 770, which has a first wavelength or range of wavelengths, while transmitting rays 780 and 790, which have different second and third wavelengths or ranges of wavelengths, respectively. The transmitted ray 780 impinges on and is deflected by the in-coupling optical element 710, which is configured to deflect light of a second wavelength or range of wavelengths. The ray 790 is deflected by the in-coupling optical element 720, which is configured to selectively deflect light of third wavelength or range of wavelengths.

With continued reference to FIG. 9A, the deflected light rays 770, 780, 790 are deflected so that they propagate through a corresponding waveguide 670, 680, 690; that is, the in-coupling optical elements 700, 710, 720 of each waveguide deflects light into that corresponding waveguide 670, 680, 690 to in-couple light into that corresponding waveguide. The light rays 770, 780, 790 are deflected at angles that cause the light to propagate through the respective waveguide 670, 680, 690 by TIR. The light rays 770, 780, 790 propagate through the respective waveguide 670, 680, 690 by UR until impinging on the waveguide's corresponding light distributing elements 730, 740, 750.

Figure 9B:
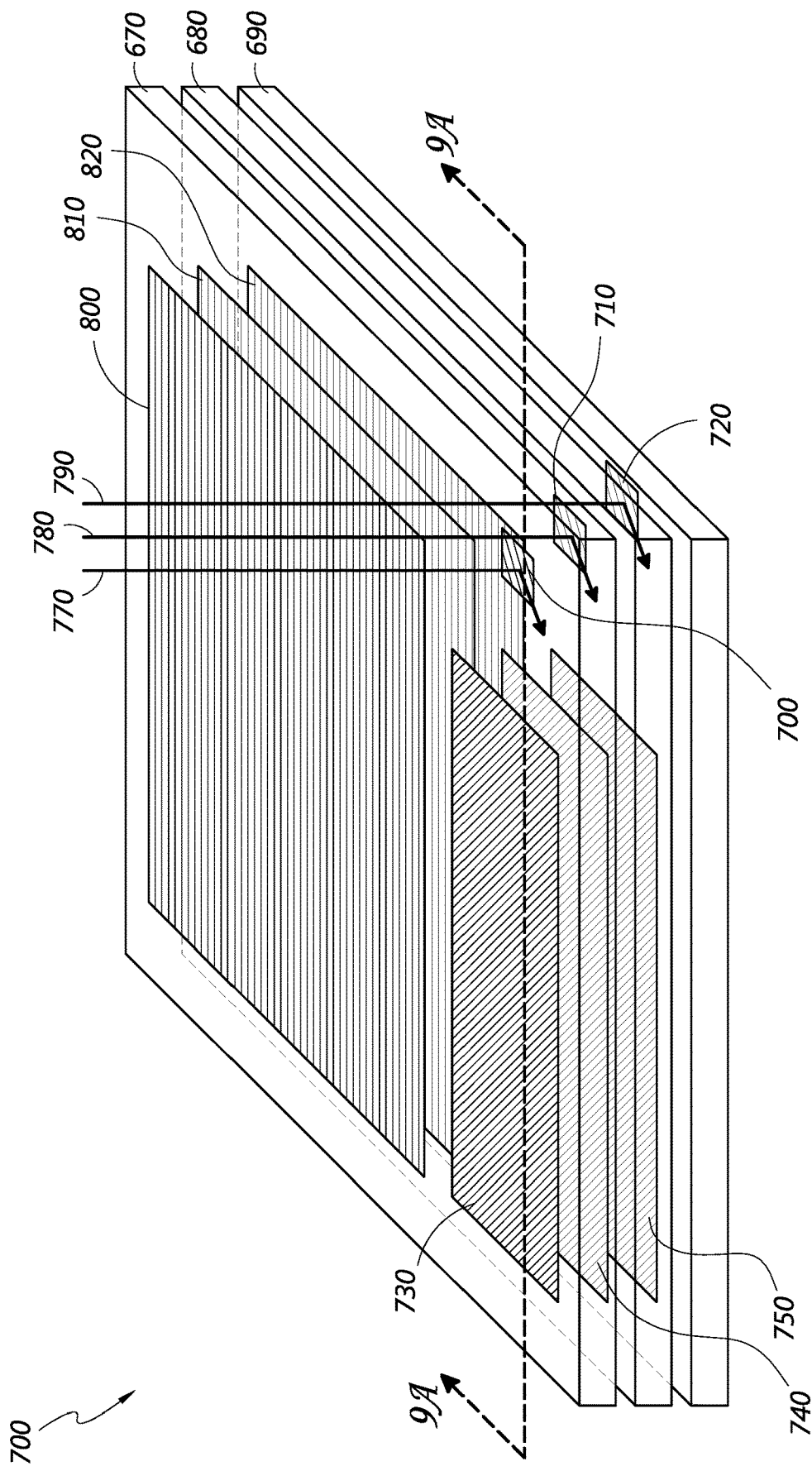
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the in-coupled light rays 770, 780, 790, are deflected by the in-coupling optical elements 700, 710, 720, respectively, and then propagate by TIR within the waveguides 670, 680, 690, respectively. The light rays 770, 780, 790 then impinge on the light distributing elements 730, 740, 750, respectively. The light distributing elements 730, 740, 750 deflect the light rays 770, 780, 790 so that they propagate towards the out-coupling optical elements 800, 810, 820, respectively.

In some embodiments, the light distributing elements 730, 740, 750 are orthogonal pupil expanders (OPE's). In some embodiments, the OPE's deflect or distribute light to the out-coupling optical elements 800, 810, 820 and, in some embodiments, may also increase the beam or spot size of this light as it propagates to the out-coupling optical elements. In some embodiments, the light distributing elements 730, 740, 750 may be omitted and the in-coupling optical elements 700, 710, 720 may be configured to deflect light directly to the out-coupling optical elements 800, 810, 820. For example, with reference to FIG. 9A, the light distributing elements 730, 740, 750 may be replaced with out-coupling optical elements 800, 810, 820, respectively. In some embodiments, the out-coupling optical elements 800, 810, 820 are exit pupils (EP's) or exit pupil expanders (EPE's) that direct light in a viewer's eye 210 (FIG. 7). It will be appreciated that the OPE's may be configured to increase the dimensions of the eye box in at least one axis and the EPE's may be to increase the eye box in an axis crossing, e.g., orthogonal to, the axis of the OPEs. For example, each OPE may be configured to redirect a portion of the light striking the OPE to an EPE of the same waveguide, while allowing the remaining portion of the light to continue to propagate down the waveguide. Upon impinging on the OPE again, another portion of the remaining light is redirected to the EPE, and the remaining portion of that portion continues to propagate further down the waveguide, and so on. Similarly, upon striking the EPE, a portion of the impinging light is directed out of the waveguide towards the user, and a remaining portion of that light continues to propagate through the waveguide until it strikes the EP again, at which time another portion of the impinging light is directed out of the waveguide, and so on. Consequently, a single beam of incoupled light may be "replicated" each time a portion of that light is redirected by an OPE or EPE, thereby forming a field of cloned beams of light, as shown in FIG. 6. In some embodiments, the OPE and/or EPE may be configured to modify a size of the beams of light.

Accordingly, with reference to FIGS. 9A and 9B, in some embodiments, the set 660 of waveguides includes waveguides 670, 680, 690; in-coupling optical elements 700, 710, 720; light distributing elements (e.g., OPE's) 730, 740, 750; and out-coupling optical elements (e.g., EP's) 800, 810, 820 for each component color. The waveguides 670, 680, 690 may be stacked with an air gap/cladding layer between each one. The in-coupling optical elements 700, 710, 720 redirect or deflect incident light (with different in-coupling optical elements receiving light of different wavelengths) into its waveguide. The light then propagates at an angle which will result in TIR within the respective waveguide 670, 680, 690. In the example shown, light ray 770 (e.g., blue light) is deflected by the first in-coupling optical element 700, and then continues to bounce down the waveguide, interacting with the light distributing element (e.g., OPE's) 730 and then the out-coupling optical element (e.g., EPs) 800, in a manner described earlier. The light rays 780 and 790 (e.g., green and red light, respectively) will pass through the waveguide 670, with light ray 780 impinging on and being deflected by in-coupling optical element 710. The light ray 780 then bounces down the waveguide 680 via TIR, proceeding on to its light distributing element (e.g., OPEs) 740 and then the out-coupling optical element (e.g., EP's) 810. Finally, light ray 790 (e.g., red light) passes through the waveguide 690 to impinge on the light in-coupling optical elements 720 of the waveguide 690. The light in-coupling optical elements 720 deflect the light ray 790 such that the light ray propagates to light distributing element (e.g., OPEs) 750 by TIR, and then to the out-coupling optical element (e.g., EPs) 820 by TIR. The out-coupling optical element 820 then finally out-couples the light ray 790 to the viewer, who also receives the out-coupled light from the other waveguides 670, 680.

Figure 9C:
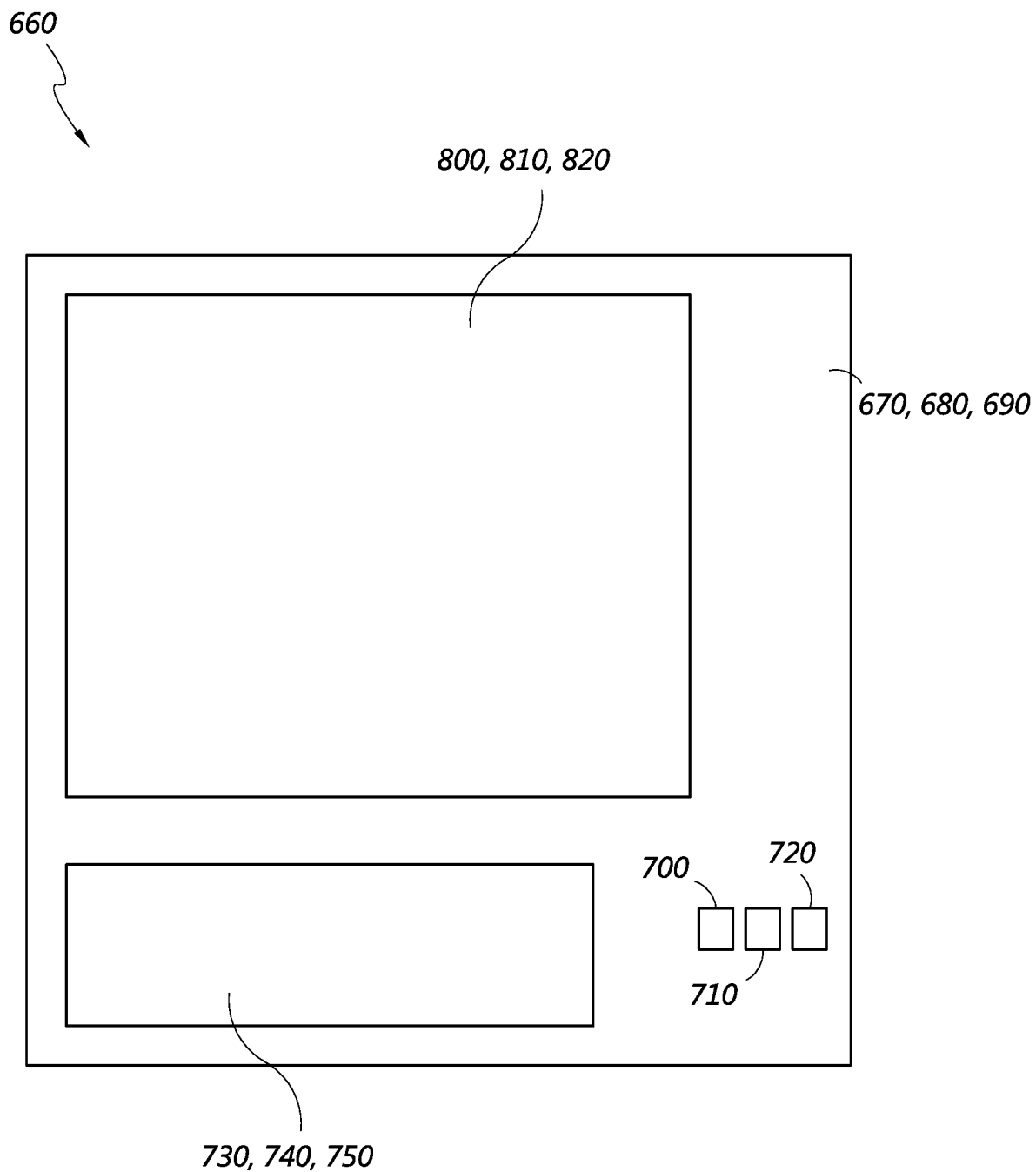
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. As illustrated, the waveguides 670, 680, 690, along with each waveguide's associated light distributing element 730, 740, 750 and associated out-coupling optical element 800, 810, 820, may be vertically aligned. However, as discussed herein, the in-coupling optical elements 700, 710, 720 are not vertically aligned; rather, the in-coupling optical elements are preferably non-overlapping (e.g., laterally spaced apart as seen in the top-down view). As discussed further herein, this nonoverlapping spatial arrangement facilitates the injection of light from different resources into different waveguides on a one-to-one basis, thereby allowing a specific light source to be uniquely coupled to a specific waveguide. In some embodiments, arrangements including nonoverlapping spatially-separated in-coupling optical elements may be referred to as a shifted pupil system, and the in-coupling optical elements within these arrangements may correspond to sub pupils.

Figure 9D:
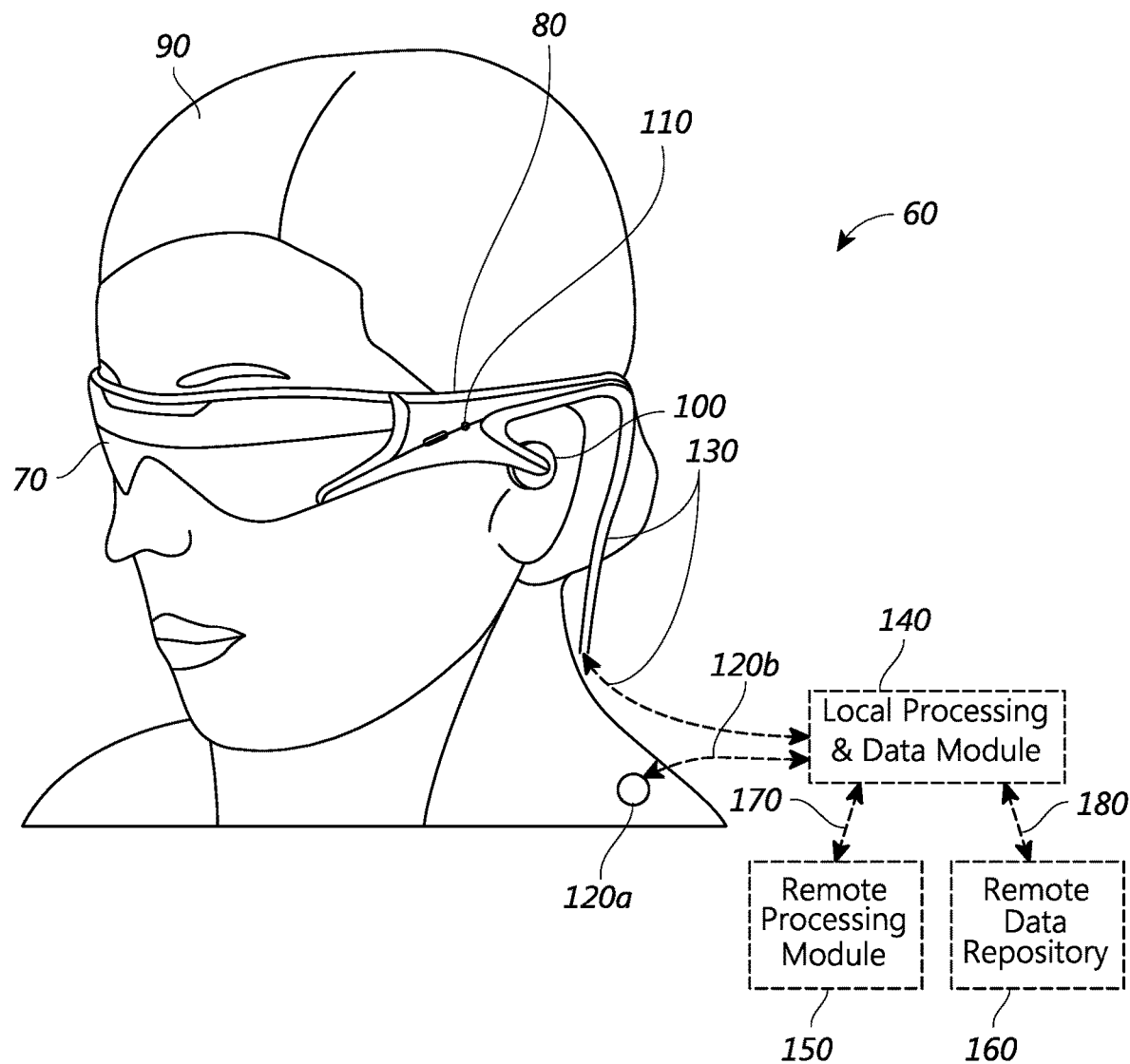
FIG. 9D illustrates an example of wearable display system.

FIG. 9D illustrates an example of wearable display system 60 into which the various waveguides and related systems disclosed herein may be integrated. In some embodiments, the display system 60 is the system 250 of FIG. 6, with FIG. 6 schematically showing some parts of that system 60 in greater detail. For example, the waveguide assembly 260 of FIG. 6 may be part of the display 70.

With continued reference to FIG. 9D, the display system 60 includes a display 70, and various mechanical and electronic modules and systems to support the functioning of that display 70. The display 70 may be coupled to a frame 80, which is wearable by a display system user or viewer 90 and which is configured to position the display 70 in front of the eyes of the user 90. The display 70 may be considered eyewear in some embodiments. In some embodiments, a speaker 100 is coupled to the frame 80 and configured to be positioned adjacent the ear canal of the user 90 (in some embodiments, another speaker, not shown, may optionally be positioned adjacent the other ear canal of the user to provide stereo/shapeable sound control). The display system 60 may also include one or more microphones 110 or other devices to detect sound. In some embodiments, the microphone is configured to allow the user to provide inputs or commands to the system 60 (e.g., the selection of voice menu commands, natural language questions, etc.), and/or may allow audio communication with other persons (e.g., with other users of similar display systems. The microphone may further be configured as a peripheral sensor to collect audio data (e.g., sounds from the user and/or environment). In some embodiments, the display system may also include a peripheral sensor 120a, which may be separate from the frame 80 and attached to the body of the user 90 (e.g., on the head, torso, an extremity, etc. of the user 90). The peripheral sensor 120a may be configured to acquire data characterizing a physiological state of the user 90 in some embodiments. For example, the sensor 120a may be an electrode.

With continued reference to FIG. 9I), the display 70 is operatively coupled by communications link 130, such as by a wired lead or wireless connectivity, to a local data processing module 140 which may be mounted in a variety of configurations, such as fixedly attached to the frame 80, fixedly attached to a helmet or hat worn by the user, embedded in headphones, or otherwise removably attached to the user 90 (e.g., in a backpack-style configuration, in a belt-coupling style configuration). Similarly, the sensor 120a may be operatively coupled by communications link 120b, e.g., a wired lead or wireless connectivity, to the local processor and data module 140. The local processing and data module 140 may comprise a hardware processor, as well as digital memory, such as non-volatile memory (e.g., flash memory or hard disk drives), both of which may be utilized to assist in the processing, caching, and storage of data. Optionally, the local processor and data module 140 may include one or more central processing units (CPUs), graphics processing units (GPUs), dedicated processing hardware, and so on. The data may include data a) captured from sensors (which may be, e.g., operatively coupled to the frame 80 or otherwise attached to the user 90), such as image capture devices (such as cameras), microphones, inertial measurement units, accelerometers, compasses, GPS units, radio devices, gyros, and/or other sensors disclosed herein; and/or b) acquired and/or processed using remote processing module 150 and/or remote data repository 160 (including data relating to virtual content), possibly for passage to the display 70 after such processing or retrieval. The local processing and data module 140 may be operatively coupled by communication links 170, 180, such as via a wired or wireless communication links, to the remote processing module 150 and remote data repository 160 such that these remote modules 150, 160 are operatively coupled to each other and available as resources to the local processing and data module 140. In some embodiments, the local processing and data module 140 may include one or more of the image capture devices, microphones, inertial measurement units, accelerometers, compasses, GPS units, radio devices, and/or gyros. In some other embodiments, one or more of these sensors may be attached to the frame 80, or may be standalone structures that communicate with the local processing and data module 140 by wired or wireless communication pathways.

With continued reference to FIG. 9D, in some embodiments, the remote processing module 150 may comprise one or more processors configured to analyze and process data and/or image information, for instance including one or more central processing units (CPUs), graphics processing units (GPUs), dedicated processing hardware, and so on. In some embodiments, the remote data repository 160 may comprise a digital data storage facility, which may be available through the internet or other networking configuration in a "cloud" resource configuration. In some embodiments, the remote data repository 160 may include one or more remote servers, which provide information, e.g., information for generating augmented reality content, to the local processing and data module 140 and/or the remote processing module 150. In some embodiments, all data is stored and all computations are performed in the local processing and data module, allowing fully autonomous use from a remote module. Optionally, an outside system (e.g., a system of one or more processors, one or more computers) that includes CPUs, GPUs, and so on, may perform at least a portion of processing (e.g., generating image information, processing data) and provide information to, and receive information from, modules 140, 150, 160, for instance via wireless or wired connections.

Liquid Crystal Materials for Adaptive Lens Assemblies

Generally, liquid crystals possess physical properties that may be intermediate between conventional fluids and solids. While liquid crystals are fluid-like in some aspects, unlike most fluids, the arrangement of molecules within liquid crystals exhibits some structural order. Different types of liquid crystals include thermotropic, lyotropic, and polymeric liquid crystals. Thermotropic liquid crystals disclosed herein can be implemented in various physical states, e.g., phases, including a nematic state/phase, a smectic state/phase, a chiral nematic state/phase or a chiral smectic state/phase.

As described herein, liquid crystals in a nematic state or phase can have calamitic (rod-shaped) or discotic (disc-shaped) organic molecules that have relatively little positional order, while having a long-range directional order with their long axes being roughly parallel. Thus, the organic molecules may be free to flow with their center of mass positions being randomly distributed as in a liquid, while still maintaining their long-range directional order. In some implementations, liquid crystals in a nematic phase can be uniaxial; i.e., the liquid crystals have one axis that is longer and preferred, with the other two being roughly equivalent. In some implementations, the liquid crystal molecules orient their long axis. In other implementations, liquid crystals can be biaxial; i.e., in addition to orienting their long axis, the liquid crystals may also orient along a secondary axis.

As described herein, liquid crystals in a smectic state or phase can have the organic molecules that form relatively well-defined layers that can slide over one another. In some implementations, liquid crystals in a smectic phase can be positionally ordered along one direction. In some implementations, the long axes of the molecules can be oriented along a direction substantially normal to the plane of the liquid crystal layer, while in other implementations, the long axes of the molecules may be tilted with respect to the direction normal to the plane of the layer.

Herein and throughout the disclosure, nematic liquid crystals are composed of rod-like molecules with the long axes of neighboring molecules approximately aligned to one another. To describe this anisotropic structure, a dimensionless unit vector n called the director, may be used to describe the direction of preferred orientation of the liquid crystal molecules.

Herein and throughout the disclosure, an azimuthal angle or a rotation angle $\varphi$ is used to describe an angle of rotation of a liquid crystal molecule about a layer normal direction, or an axis normal to a major surface of a liquid crystal layer, which is measured in a plane parallel to a major surface of the liquid crystal layers or of the substrate, e.g., the x-y plane, and measured between an alignment direction, e.g., an elongation direction or the direction of the director, and a direction parallel to the major surface, e.g., the y-direction.

Herein and throughout the disclosure, when an angle such as the rotation angle $\varphi$ referred to as being substantially the same or different between different regions, it will be understood that the average angles can, for example, be within about 1%, about 5% or about 10% of each other although the average angles can be larger in some cases.

As describe herein, some liquid crystals in a nematic state or a smectic state can also exhibit a twist in a layer normal direction. Such liquid crystals are referred to as being twisted nematic (TN) liquid crystals or twisted smectic (SN) liquid crystals. TN or SN liquid crystals can exhibit a twisting of the molecules about an axis perpendicular to the director, with the molecular axis being parallel to the director. When the degree of twist is relatively large, twisted liquid crystals may be referred to as being in a chiral phase or a cholesteric phase.

As described herein, TN or SN liquid crystals can be described as having a twist angle or a net twist angle ($\phi$), which can refer to, for example, the relative azimuthal angular rotation between an uppermost liquid crystal molecule and a lowermost liquid crystal molecule across a specified length, e.g., the thickness of the liquid crystal layer.

As described herein, "polymerizable liquid crystals" may refer to liquid crystal materials that can be polymerized, e.g., in-situ photopolymerized, and may also be described herein as reactive mesogens (RM).

The liquid crystal molecules may be polymerizable in some embodiments and, once polymerized, may form a large network with other liquid crystal molecules. For example, the liquid crystal molecules may be linked by chemical bonds or linking chemical species to other liquid crystal molecules. Once joined together, the liquid crystal molecules may form liquid crystal domains having substantially the same orientations and locations as before being linked together. The term "liquid crystal molecule" may refer to both the liquid crystal molecules before polymerization and to the liquid crystal domains formed by these molecules after polymerization. Once polymerized, the polymerized network may be referred to as liquid crystal polymer (LCP).

In some embodiments, unpolymerized liquid crystal molecules or polymerizable liquid crystal molecules prior to being polymerized may have at least limited rotational degree of freedom. These unpolymerized liquid crystal molecules can rotate or tilt, e.g., under an electrical stimulus, which results in alteration of the optical properties. For example, by applying an electric field, some liquid crystal layers including unpolymerized liquid crystal molecules may be switched between one or more states having different diffractive or polarization altering properties.

The inventors have recognized that the above-described properties of liquid crystals or reactive mesogens (RMs) can be advantageously applied to various components of switchable waveplates and waveplate lenses disclosed herein. For example, in some unpolymerized RMs, the orientations of LC molecules of can be altered after deposition, e.g., by application of an external stimulus, e.g., electric field. Based on this recognition, the inventors disclose herein waveplates and waveplate lenses that can be switched between a plurality of states by application of an external stimulus.

In addition, the inventors have recognized that, when unpolymerized, the orientations of LC molecules at surfaces or interfaces of some LCs or RMs can be aligned by controlling the surface or interface on which the LC molecules are formed. For example, a stack of multiple LC layers can be formed where, by controlling orientations of LC molecules closest to the surface of an LC layer, orientations of immediately adjacent LC molecules in the next LC layer can be controlled, e.g., to have the same orientation as the LC molecules closest to the surface in the previous LC layer or same orientation as elongated microstructures in adjacent layers. In addition, LC molecules between the LC molecules at surfaces or interfaces can be controlled to have a predetermined amount of twist. Based on recognition of these and other attributes including birefringence, chirality, and ease for multiple-coating, the inventors disclose herein waveplates and waveplate lenses that have useful properties such as broadband capability with tailored optical properties, e.g., diffraction efficiency, optical power and polarizability, to name a few.

Display Devices Having Adaptive Lens Assemblies

As described supra in reference to FIG. 6, some display systems according to embodiments include a waveguide assembly 260 configured to form images at a plurality of virtual depth planes. The waveguide assembly 260 includes waveguides 270, 280, 290, 300, 310 each configured to propagate light by total internal reflection (TIR), and includes out-coupling optical elements 570, 580, 590, 600, 610 each configured to extract light out of a respective one of the waveguides 270, 280, 290, 300, 310 by redirecting the light. Each of the waveguide 270, 280, 290, 300, 310 is configured to output light to form an image corresponding to a particular depth plane. The waveguide assembly 260 may also optionally include a plurality of lenses 320, 330, 340, 350 between the waveguides for providing different optical powers for forming the images at different virtual depth planes.

In the illustrated embodiment of the waveguide assembly 260 in FIG. 6, the number of depth planes may be directly proportional to the number of waveguides and lenses. However, the inventors have recognized various challenges associated with implementing a waveguide assembly configured for displaying images at a plurality of depth planes by having a proportional number of waveguides and lenses. For example, a high number of waveguides 270, 280, 290, 300, 310 and a high number of corresponding lenses 320, 330, 340, 350 can undesirably increase the overall thickness, weight, cost, and manufacturing challenges to the waveguide assembly 260. For example, when formed of a conventional lens material, e.g., glass, each of the lenses 320, 330, 340, 350 may add millimeters or tens of millimeters in thickness and corresponding weight to the displays. In addition, a high number of waveguides and lenses can produce undesirable optical effects to the user, e.g., relatively high absorption loss. Thus, in one aspect, the inventors have recognized a potential benefit in some cases for display systems that can generate images at a plurality of depth planes with fewer numbers of waveguides, fewer number of lenses, thinner and lighter waveguides and lenses and/or fewer numbers of lenses per waveguide.

As used herein, optical power (P, p or $\phi$), also referred to as refractive power, focusing power, or convergence power) refers to the degree to which a lens, mirror, or other optical system converges or diverges light. It is equal to the reciprocal of the focal length of the device: $P=1/f$. That is, high optical power corresponds to short focal length. The SI unit for optical power is the inverse meter ($m^{-1}$), which is commonly called the diopter (D).

As described herein, converging lenses that focus light passing therethrough are described as having a positive optical power, while diverging lenses that defocus light passing therethrough are described as having a negative power. Without being bound by theory, when light passes through two or more thin lenses that are relatively close to each other, the optical power of the combined lenses may be approximated as a sum of the optical powers of the individual lenses. Thus, when light passes through a first lens having a first optical power P1 and further passes through a second lens having a second optical power P2, the light may be understood to converge or diverge according to a sum of optical powers Pnet=P1+P2.

A medium having a refractive index that depends on the polarization and propagation direction of light is referred to be birefringent (or birefractive). As described throughout the specification and understood in the relevant industry, light whose polarization is perpendicular to the optic axis of a birefringent medium is described as having an ordinary refractive index ($n_o$), light whose polarization is parallel to the optic axis of the birefringent medium is described as having an extraordinary refractive index ($n_e$), and a difference of the refractive indices $n_e$-$n_o$ observed in the birefringent medium material is described as having a birefringence $\Delta n$. The phase retardation of light in a material medium having birefringence $\Delta n$ can be expressed as $\Gamma=2\pi\Delta nd/\lambda$ at different $\lambda$, where d is the thickness of the medium.

As described herein, a "transmissive" or "transparent" structure, e.g., a transparent substrate, may allow at least some, e.g., at least 20, 30, 50, 70 or 90%, of an incident light, to pass therethrough. Accordingly, a transparent substrate may be a glass, sapphire or a polymeric substrate in some embodiments. In contrast, a "reflective" structure, e.g., a reflective substrate, may reflect at least some, e.g., at least 20, 30, 50, 70, 90% or more of the incident light, to reflect therefrom.

Figure 10:
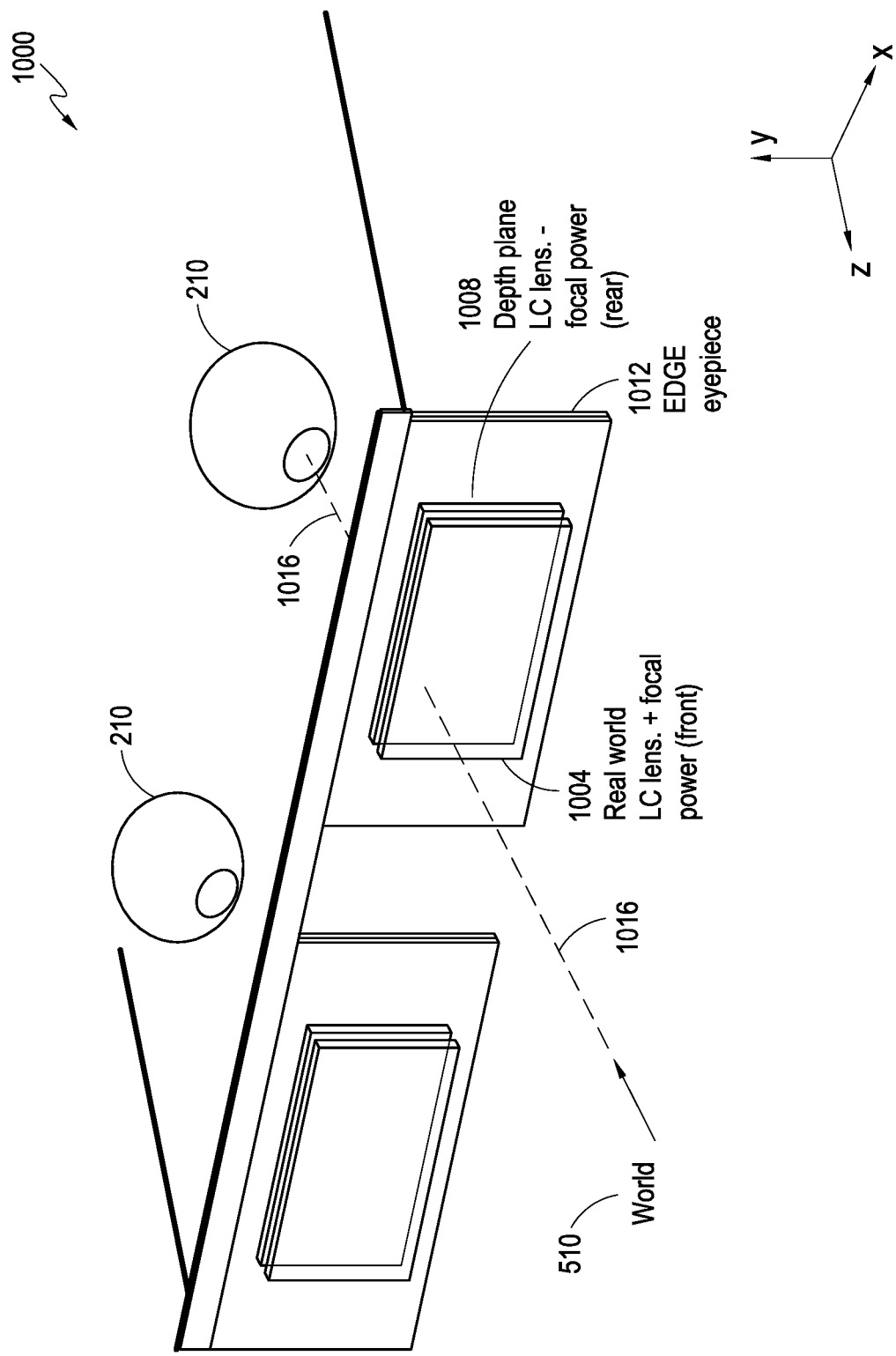
FIG. 10 illustrates an example of a display system comprising a pair of adaptive lens assemblies.

FIG. 10 illustrates an example of a display device 1000, e.g., a wearable display device, comprising one or more adaptive lens assemblies including a polarization-selective lens stack, e.g., a pair of adaptive lens assemblies 1004, 1008 in an optical path 1016 that are interposed by a waveguide assembly 1012. As described supra, the waveguide assembly includes a waveguide configured to propagate light (e.g., visible light) under total internal reflection and to outcouple the light in an optical axis extending from (e.g., in a direction normal to) a light output surface of the waveguide (e.g., a major surface of the waveguide). The light may be outcoupled by a diffraction grating in some embodiments. Each of the adaptive lens assemblies 1004, 1008 may be configured to at least partially transmit outcoupled light therethrough. In the illustrated embodiments, each of the adaptive lens assemblies may be configured to receive outcoupled light from the waveguide assembly 1012 and to converge or diverge the outcoupled light in the optical axis direction. Each of the adaptive lens assemblies 1004, 1008 comprises a polarization-selective lens stack comprising a birefringent lens and an isotropic lens contacting each other, wherein contacting surfaces of the birefringent lens and the isotropic lens form a conformal interface therebetween. The adaptive lens assembly is configured to be selectively switched between a plurality of states having different optical powers. The adaptive lens assembly are be configured to alter a polarization state of the outcoupled light passing therethrough when activated (e.g., electrically activated).

As used herein, an adaptive lens assembly refers to a lens assembly having at least one optical property that may be adjusted, e.g., reversibly activated and deactivated, using an external stimulus. Example optical properties that may be reversibly activated and deactivated include, among other properties, optical power (focal length), phase, polarization, polarization-selectivity, transmissivity, reflectivity, birefringence and diffraction properties, among other properties. In various embodiments, adaptive lens assemblies are capable of electrically varying the optical power and the polarization state of light passing therethrough.

In the illustrated embodiment, each of the pair of adaptive lens assemblies 1004, 1008 is configured to be selectively switched between at least two states, where, in a first state each is configured to pass the outcoupled light therethrough without altering a polarization state thereof, while in a second state each is configured to alter the polarization state of the outcoupled light passing therethrough. For example, in the second state, each of the adaptive lens assemblies 1004, 1008 reverses the handedness of circularly polarized light, while in the first state, each of the adaptive lens assemblies 1004, 1008 preserves the handedness of circularly polarized light.

Still referring to FIG. 10, the display device 1000 further comprises a waveguide assembly 1012 interposed between the pair of adaptive lens assemblies 1004, 1008. The waveguide assembly 1012 may be similar to the waveguide assembly 260 described above with respect to FIG. 6, which comprises one or more waveguides, similar to one or more waveguides 270, 280, 290, 300, 310 in FIG. 6. As described supra, e.g., with respect to FIGS. 6 and 7, the waveguide may be configured to propagate light under total internal reflection in a lateral direction parallel to a major surface of the waveguide. The waveguide may further be configured to outcouple the light, e.g., in a direction normal to the major surface of the waveguide.

Still referring to FIG. 10, a first adaptive lens assembly 1004 of the pair of adaptive lens assemblies is disposed on a first side of the waveguide assembly 1012, e.g., the side of the world 510 observed by a user, and a second adaptive lens assembly 1008 of the pair of lens assemblies is disposed on a second side of the waveguide assembly 1012, e.g., the side of the eye 210 of the user. As described infra, the pair of adaptive lens assemblies as configured provides to a user virtual content from the waveguide assembly 1012 at a plurality of virtual depth planes, as well the view of the real world. In some embodiments, there is little or no distortion due to the presence of the pair of adaptive lens assemblies. The virtual content and the view of the real world are provided to the user upon activation of the first and second adaptive lens assemblies 1004, 1008, as described infra with respect to FIGS. 11A and 11B.

Figures 11A, 11B:
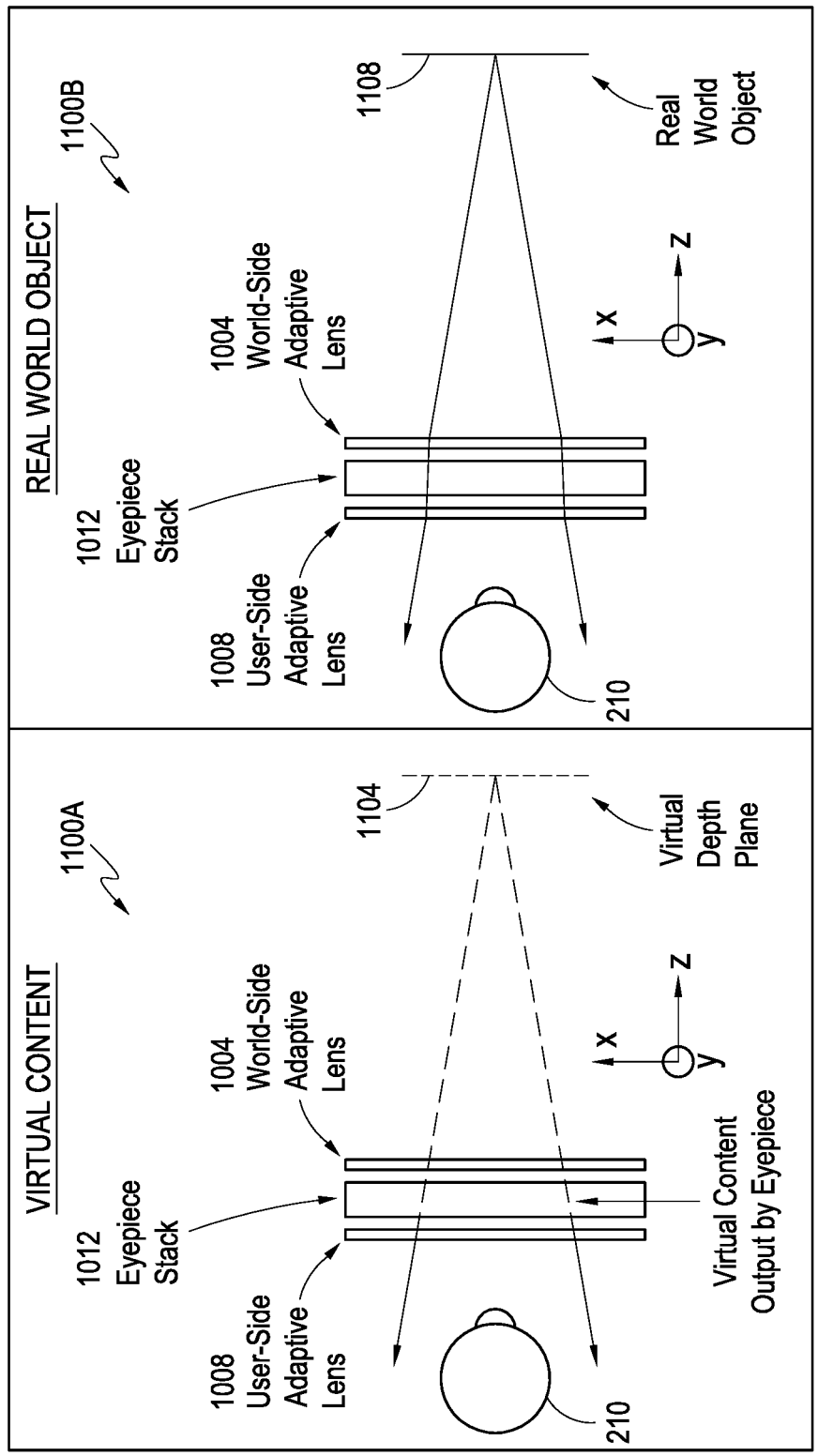
FIG. 11A illustrates an example of the display system of FIG. 10 displaying virtual content to a user at a virtual depth plane using an adaptive lens.
FIG. 11B illustrates an example of the display system of FIG. 10 providing a view of real world content to a user through adaptive lenses.

FIGS. 11A and 11B illustrate examples of display devices 1100A/1100B, each comprising adaptive lens assemblies in operation to output image information to a user. The display devices 1100A and 1100B in unpowered state are structurally identical, in some embodiments. The display device 1100A is used herein to describe outputting virtual image to the user, while the display device 1100B is used herein to describe transmitting a real world image through the display device 1100B to the user. The display device 1100A/1100B includes a pair of the switchable lenses assemblies 1004, 1008 that are configured to be electrically activated by, e.g., application of a voltage or a current. In some embodiments, in a deactivated state, e.g., when no voltage or current is applied, each of the first and second switchable lenses assemblies 1004, 1008 has a low, e.g., about zero, optical power. In some embodiments, in an activated state, e.g., when a voltage or a current is applied, the first adaptive lens assembly 1004 on the side of the world may provide a first net optical power (Pnet1) having a first sign, e.g., a positive optical power. When in an activated state, the second adaptive lens assembly 1008 on the side of the user may provide a second net optical power (Pnet2) having a second sign, e.g., a negative optical power. However, embodiments are not so limited, and in other embodiments, the first and second adaptive lens assemblies may provide the optical powers in the deactivated state while providing substantially zero power when activated.

FIG. 11A illustrates an example of the display system of FIG. 10 displaying virtual content to a user at a virtual depth plane, according to some embodiments. As described supra, the waveguide assembly 1012 interposed between the pair of the adaptive lens assemblies 1004, 1008 comprises a waveguide configured to receive light containing virtual image information and propagate the light under total internal reflection. The waveguide assembly 1012 is further configured to outcouple the light through, e.g., a diffraction grating, towards the eye 210. The outcoupled light passes through the second adaptive lens assembly 1008 prior to entering the eye 210. When activated, the second adaptive lens assembly 1008 has a second net optical power, Pnet2, which may have a negative value, such that the user sees the virtual image at a virtual depth plane 1104.

In some embodiments, the second net optical power Pnet2 may be adjusted electrically to adjust the second net optical power (Pnet2) of the second adaptive lens assembly 1008, thereby adjusting the distance to the virtual depth plane 1104. For example, as a virtual object "moves" closer and further relative to the eye 210 within a virtual three dimensional space, the second net optical power Pnet2 of the second adaptive lens assembly 1008 may be correspondingly adjusted, such that the virtual depth plane one 1104 adjusts to track the virtual object. Thus, the user may experience relatively little or no accommodation/vergence mismatch beyond an acceptable threshold. In some embodiments, the magnitude of the distance to the virtual depth plane 1104 may be adjusted in discrete steps, while in some other embodiments, the magnitude of the distance to the virtual depth plane 1104 may be adjusted continuously.

FIG. 11B illustrates an example of the display system of FIG. 10 providing a view of real world content to a user, according to some embodiments. When the second adaptive lens assembly 1008 is activated to have the second net optical power (Pnet2) to display the virtual content at the virtual depth plane 1104, light from the real world passing through the second adaptive lens assembly 1008 may also be converged or diverged according to Pnet2 of the activated second adaptive lens assembly 1008. Thus, objects in the real world may appear out of focus or distorted. To mitigate such distortion, according to embodiments, when activated, the first and second adaptive lens assemblies 1004, 1008 may be configured to have optical powers having opposite signs. In some embodiments, light passing through the first and second adaptive lens assemblies 1004, 1008 converges or diverges according to a combined optical power having a magnitude that is about a difference between magnitudes of first and second net optical powers Pnet1, Pnet2, of the first and second adaptive lens assemblies 1004, 1008, respectively. In some embodiments, the waveguide assembly 1012 may also have optical power and the adaptive lens assembly 1008 may be configured to account for the distortions caused by both the lens assembly 1004 and the waveguide assembly 1012. For example, the optical power of the adaptive lens assembly 1008 may be opposite in sign to the sum of the optical powers of the lens assembly 1004 and the waveguide assembly 1012.

In some embodiments, the first adaptive lens assembly 1004 is configured to have the first net optical power Pnet1 that has a magnitude that is close to or the same as the magnitude of the second net optical power Pnet2 of the second adaptive lens assembly 1008 while having an opposite sign. As a result, when both the first and second adaptive lens assemblies 1004, 1008 are activated simultaneously, objects in the real world appear relatively unaffected by the optical power of the second adaptive lens assembly 1008 provided for displaying the virtual content.

In some embodiments, first adaptive lens assembly 1004 may be configured such that when activated, the first net optical power Pnet1 dynamically matches the second net optical power Pnet2 of the second adaptive lens assembly 1008. For example, as the second net optical power. Pnet1 of the second switchable assembly 1008 is adjusted to track moving virtual objects within the virtual three dimensional space, the first net optical power Pnet1 of the first adaptive lens assembly 1004 may be dynamically adjusted, such that the magnitude of the combined optical power P=Pnet1+Pnet2 may be kept less than a predetermined value. Thus, according to embodiments, the objects in the real world may be prevented from being unacceptably out of focus by compensating the second net optical power (Pnet2) of the second adaptive lens assembly 1008, which may have a negative value, with the first net optical power (Pnet1) of the first adaptive lens assembly 1004, such that the combined optical power P=Pnet1+Pnet2 remains small, e.g., near about 0 m$^{-1}$.

Polarization-Selective Lens Stack Comprising Birefringent Lens and Isotropic Lens for Adaptive Lens Assemblies Various embodiments described herein provide adaptive lens assemblies that include a polarization-selective lens stack. In certain implementations, the polarization-selective lens stack comprises a birefringent lens, e.g., a Fresnel birefringent lens, and an isotropic lens contacting each other. Such assemblies can be compact (e.g., can have reduced thickness) and/or be lightweight. These assemblies may potentially also provide various advantageous optical functionalities such as high bandwidth, increased switching speeds, reduced chromatic aberrations, increased ease of alignment, and/or variable optical power. In addition, various embodiments described herein can provide adaptive lens assemblies with relatively low amount of leakage light that can otherwise lead to "ghost" images. According to various embodiments, adaptive assemblies comprise a polarization-selective lens stack comprising a birefringent lens and an isotropic lens, as described herein.

Referring to FIG. 12A, to provide images at a plurality of depth planes with high efficiency over a wide range of the visible spectrum, adaptive lens assemblies according to various embodiments include a polarization-selective lens stack 1200 configured to exert polarization-dependent optical power to linearly polarized light. The polarization-selective lens stack 1200 comprises a birefringent lens 1200 having an optic axis 1202 extending in a lateral direction, e.g., x-direction or y-direction direction, perpendicular to the direction of light propagation, e.g., the z-direction. The birefringent lens 1204 has a birefringence (Δn). As described above, Δn corresponds to a difference between an extraordinary refractive index ($n_e$) and an ordinary refractive index ($n_o$) of the birefringent lens 1204. The birefringent lens 1204 can have a radius of curvature (R1) such that it is configured to exert a first optical power ($p_1$) to light passing therethrough and having a polarization direction parallel to the optic axis, and to exert a second optical power ($p_2$) to light passing therethrough and having a polarization direction perpendicular to the optic axis.

The polarization-selective lens stack 1200 additionally includes an isotropic lens 1208 having a refractive index ($n_c$) and has a second radius of curvature (R2) such that it is configured to exert to light passing therethrough a third optical power (p3) opposite in sign as the first optical power (p1) and the second optical power (p2).

In the illustrated embodiment, without limitation, the $n_c$ of the isotropic lens 1208 has substantially the same value as the $n_o$ of the birefringent lens 1204. However, it will be appreciated that the $n_c$ can be different from the $n_o$ in some other embodiments.

In the illustrated embodiment, without limitation, the first radius of curvature (R1) and the second radius of curvature (R2) are substantially the same in magnitude (R) while having opposite signs. Furthermore, because the R1 and the R2 are substantially the same in magnitude, the birefringent lens 1204 and the isotropic lens 1208 make continuous contact along the interface having the radius of curvature R. That is, the contacting surfaces of the birefringent lens 1204 and the isotropic lens 1208 form a conformal interface therebetween.

With reference to FIG. 12B, the polarization-selective lens stack 1200 is illustrated in operation when an incident light 1212, e.g., linearly polarized light, has a direction of polarization that is parallel to the direction of the optic axis 1202. Under this condition, because light passing through the birefringent lens 1204 experiences a refractive index corresponding to $n_e$ and light passing through the isotropic lens 1208 experiences a refractive index corresponding to $n_o$, the lens stack 1200 exerts an optical power to the light that can be expressed as:

$$\varphi_1 = \frac{(n_e - n_o)}{R} = \frac{\Delta n}{R}$$

where R represents the magnitude of radii of the birefringent lens 1204 and the isotropic lens 1208.

With reference to FIG. 12C, the polarization-selective lens stack 1200 is illustrated in operation when an incident light 1216, e.g., linearly polarized light, has a direction of polarization that is perpendicular to the direction of the optical axis 1202. Under this condition, because light passing through the birefringent lens 1204 experiences a refractive index corresponding to $n_o$, which is the same as $n_o$ the refractive index experienced by light passing through the isotropic lens 1208, the lens stack 1200 exerts an optical power to the light that can be expressed as:

$$\varphi_1 = \frac{(n_o - n_o)}{R} \cong 0$$

where R represents the magnitude radii of the birefringent lens 1204 and the isotropic lens 1208.

Still referring to FIGS. 12A-12C, in some embodiments, the isotropic lens 1208 may be formed of an isotropic material, e.g., glass, acrylic, etc. On the other hand, the birefringent lens 1204 may be formed of or comprises a birefringent material, e.g., liquid crystals according to various embodiments. For example, the birefringent lens 1204 may comprise a transparent substrate e.g., a glass substrate, having formed thereon liquid crystal (LC) molecules that are elongated along a lateral direction (e.g., x-direction or y-direction) perpendicular to the light propagation direction (e.g., z-direction).

However, embodiments are not so limited and in other embodiments, the birefringent lens 1204 may be formed of or comprises a suitable birefringent material other than LCs. For example, the birefringent lens 1204 may comprise, e.g., $BaB_2O_4$, $Be_3Al_2(SiO_3)_6$, $CaCO_3$ $LiNO_3$ $TiO_2$ SiC, tourmaline and $ZrSiO_4$ to name a few.

Polarization-Selective Lens Stack Comprising a Birefringent Fresnel Lens and Isotropic Lens for Adaptive Lens Assemblies As described above with respect to FIGS. 12A-12C, a lens stack comprising a birefringent lens, e.g., LC-based birefringent lens, and an isotropic lens can provide polarization-selective lensing effect. In the following, a polarization-selective lens stack comprising a liquid crystal-based birefringent lens configured as a Fresnel lens is described.

A Fresnel lens can for example comprise a thin-plate type of lens, which comprises fractional prismatic structures formed by breaking a conventional curved (e.g., spherical) lens into a set of sections, e.g., concentric annular sections, known as Fresnel zones. The Fresnel zones replace the continuous curvature of a continuous refractive lens with a set of surfaces of the same shape having discontinuities between them. A substantial reduction in thickness can be achieved by employing such fractional sections and lenses with a relatively large aperture can be manufactured using a smaller volume of material.

Figure 13B:
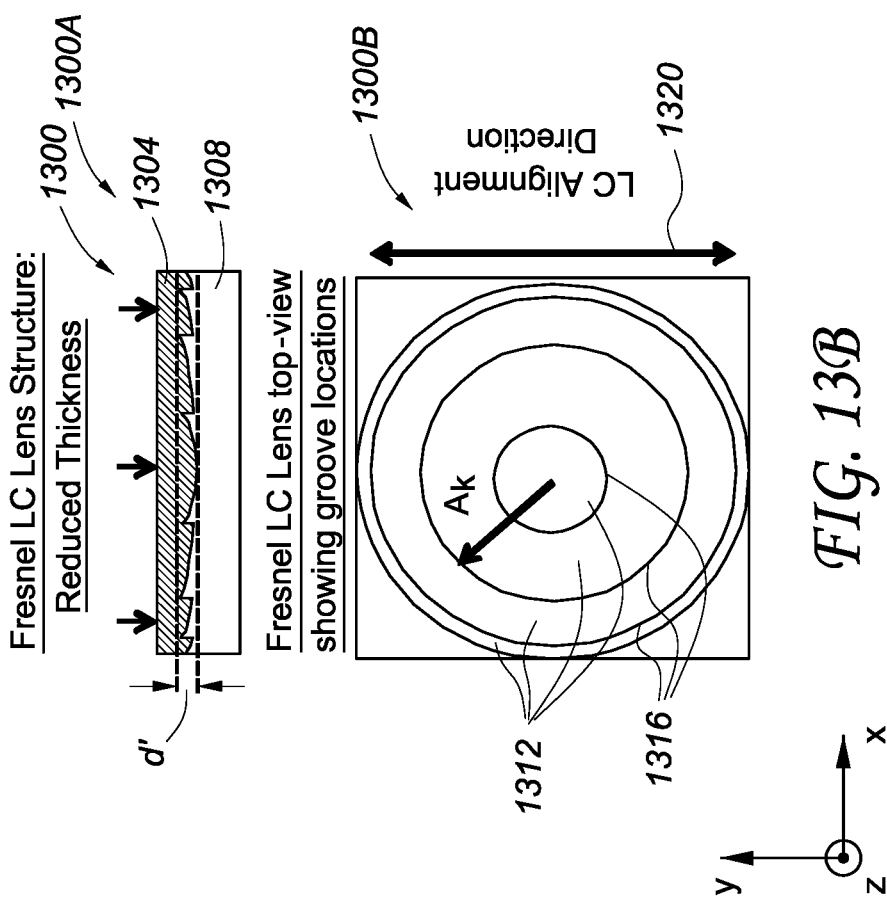
FIG. 13B illustrates cross-sectional and top down views of an example of a polarization-selective lens stack comprising a birefringent Fresnel lens and an isotropic lens.
Figure 13A:
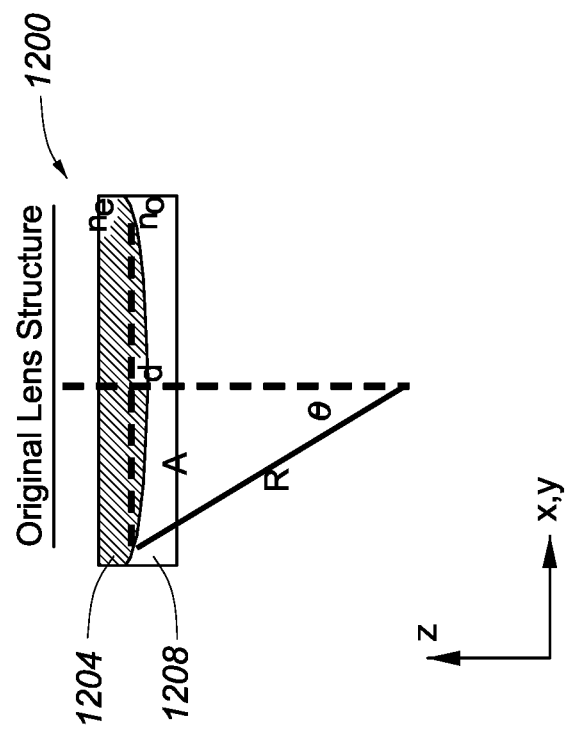
FIG. 13A illustrates the polarization-selective lens stack of FIG. 12A with annotated parameters.

FIG. 13A illustrates a cross-sectional side view of the lens stack 1200 described above with respect to FIGS. 12A-12C, annotated with relevant optical dimensions including the distance R to a given location on the birefringent lens 1204 from the focal point, the radial distance A to the given location from a central axis (e.g., optical axis) of the lens stack 1200, the angle θ defined by the distances R and A, and the thickness d of the curved portion of the birefringent lens 1204. As described above, in various implementations, because the birefringent lens 1204 and the isotropic lens 1208 have substantially the same radius of curvature, the birefringent lens 1204 and the isotropic lens 1208 make continuous contact along the interface formed therebetween having the radius of curvature R.

FIG. 13B illustrates a cross-sectional side view 1300A (top) and a top down view 1300B (bottom) of a lens stack 1300 comprising a birefringent Fresnel lens 1304 and a counterpart lens, e.g., an isotropic Fresnel lens 1308. By employing the Fresnel lens 1304, the groove thickness d' of the curved portion of the birefringent lens 1304 can be substantially reduced. Despite the substantially reduced thickness d', the lens stack 1300 has a corresponding curvature such as effective radius of curvature R corresponding to the actual radius of curvature R of the conventional lens illustrated with respect to FIG. 13A. Accordingly, while not illustrated, the lens stack 1300A additionally has a radial distance $A_k$ of a given Fresnel zone or a groove 1306 from a central axis of the lens stack 1300 and the angle θ defined by the distances R and $A_k$. In some implementations such as shown in FIG. 13B, despite the grooves separating the Fresnel zones, the birefringent Fresnel lens 1304 and the isotropic lens 1308 make continuous contact throughout the interface formed therebetween having the effective radius of curvature R. In some embodiments, successive Fresnel zones in the radially outward direction can have different radial distances $A_k$ and different distances between adjacent grooves 1306. For example, in the illustrated embodiment, the distances between adjacent Fresnel zones become smaller in the radially outward direction of the birefringent Fresnel lens 1304. However, embodiments are not so limited and in other embodiments, the radial distances $A_k$ of successive Fresnel zones can increase linearly with constant distances between adjacent Fresnel zones while having different groove thicknesses within each zone to provide similar or same optical effects as the illustrated embodiment.

Referring to FIG. 13B (bottom), the illustrated birefringent Fresnel lens 1304 comprises a plurality of concentric Fresnel zones according to embodiments. The birefringent Fresnel lens 1304 has a plurality of grooves 1316 forming boundaries of Fresnel zones 1312 at distances from the central axis represented by radii $A_k$. According to various embodiments, the groove thickness d' of the birefringent lens 1304 is designed such that the path length is a multiple of the design wavelength λ (i.e., $n_e d' = m\lambda$). This arrangement can create a 2 πm phase jump between the zones that leads to the same wavefront. The value of d' can be chosen (e.g., optimized) to balance fabrication tolerances and to reduce or minimize aberrations that can arise from sharp edges of the grooves 1316. In one example, the radius R, of the $k^{th}$ Fresnel zone can be calculated by setting the thickness of the curved region to be kd', by the following equation:

$$A_k = \sqrt{\frac{2\Delta n f k m \lambda}{n_o} - \left(\frac{k m \lambda}{n_o}\right)^2},$$

where k represents the number of the Fresnel zone counting from the center of the lens, and where the groove thickness d' is constant across the surface of the illustrated birefringent Fresnel lens 1304.

In some embodiments, the birefringent Fresnel lens 1304 includes LCs. The LC molecules may be laterally aligned, or have elongation directions extending, substantially in a lateral direction 1320 indicated by the arrow (e.g., y direction). In addition, the alignment directions of the LC molecules may be substantially homogenous throughout the thickness of the birefringent Fresnel lens 1304 without undergoing rotation. That is, the local director n of the LC molecules may be substantially constant laterally across the area and vertically across the thickness (e.g., in z direction) of the birefringent Fresnel lens 1304. The illustrated alignment may be suitable, e.g., for providing polarization selectivity for linearly polarized light. In these embodiments, linearly polarized light having polarization direction that is parallel to the direction of LC alignment (e.g., y direction) may experience one of $n_e$ or $n_o$, while linearly polarized light having polarization direction that is perpendicular to the direction of LC alignment (e.g., x direction) may experience the other of $n_e$ or $n_o$. As a result, the lens stack 1300 exerts an optical power of Δn/R for light having one linear polarization while exerting a substantially zero optical power for light having the other linear polarization, as described above.

In various embodiments herein and throughout the specification, the birefringent Fresnel lens 1304 can have an average, a local, a mean, a median, a maximum or a minimum birefringence (Δn) of 0.05-0.10, 0.15-0.20, 0.20-0.25, 0.25-0.30, 0.30-0.35, 0.35-0.40, 0.40-0.45, 0.45-0.50, 0.50-0.55, 0.55-0.60, 0.60-0.65, 0.65-0.70, or any value within any range defined by any of these values, for instance 0.05-0.40. In addition, the birefringent Fresnel lens 1304 can a have a within-layer birefringence (Δn) range of 0.01-0.05, 0.05-0.10, 0.15-0.20, 0.20-0.25, 0.25-0.30, 0.30-0.35, 0.35-0.40, or any value within any range defined by any of these values.

In various embodiments herein and throughout the specification, the birefringent Fresnel lens 1304 has a thickness of about 0.1 μm-200 μm, 0.1-5 μm, 5-50 μm, 50-100 μm, 100-150 μm, 150-200 μm, or a value within any range defined by these values, for instance 5-200 μm.

Adaptive Lens Assemblies Comprising Polarization-Selective Lens Stack Coupled with Switchable Waveplate To provide images at a plurality of depth planes with high efficiency over a wide range of the visible spectrum, adaptive lens assemblies according to various embodiments include a polarization-selective lens stack (e.g., 1200 in FIGS. 12A-12C, 1300 in FIG. 13B) comprising a birefringent lens and an isotropic lens. According to various embodiments, adaptive lens assemblies can be selectively switched between a plurality of states with different optical powers. In the following, adaptive lens assemblies are disclosed, in which the selective switching is performed by activating or deactivating a switchable waveplate coupled to a polarization-selective lens included in the adaptive lens assembly according to embodiments.

Referring to FIG. 14A, in some embodiments, the adaptive lens assembly 1400A is configured to be activated or deactivated by employing a switchable waveplate 1404 comprising LCs in the same optical path as the polarization-selective lens stack 1300 described above comprising a birefringent Fresnel lens 1304 and an isotropic lens 1308. The Fresnel lens 1304 may be formed using LCs or other birefringent materials. The adaptive lens assembly 1400A may be selectively switched between different states by electrically activating and deactivating the switchable waveplate 1404 (or otherwise changing the states of the waveplate, e.g., by applying different voltages). One example of the switchable waveplate 1404 is illustrated with respect to FIG. 14B.

Referring to FIG. 14B, in some embodiments, the switchable waveplate 1402 may be a half waveplate or a polarization rotator comprising a layer 1402 of unpolymerized twisted nematic (TN) liquid crystals (LCs), or reactive mesogens (RM) comprising TN LC molecules, which is configured to be switched upon application of an electric field across a thickness of the layer 1402 of TN LCs. The layer 1402 of TN LCs is disposed between a pair of transparent substrates 1412. Each of the transparent substrates 1412 has formed on the inner surface a conducting transparent electrode 1416, 1420. In some embodiments, the transparent electrodes 1416, 1420 may serve as substrates, and one or both of the substrates 1412 may be omitted.

The surfaces of the transparent electrodes 1416, 1420 and/or the substrates 1412 may be configured such that the TN LC molecules in contact with or immediately adjacent to the upper electrode 1416 tend to orient with their long axes extending in a first lateral direction, while the TN LC molecules in contact with or immediately adjacent to the lower electrode 1420 tend to orient with their long axes extending in a second lateral direction, which may cross, e.g., to form an angle of about 90 degrees relative to, the first lateral direction. Accordingly, the TN LC molecules between the electrodes 1416, 1420 undergo a twist.

Still referring to FIG. 14B (left), in operation, in the absence of an electric field (deactivated state) across the TN LC layer 1402, the nematic director of the TN LC molecules undergoes a smooth 90 degree twist across the thickness of the TN LC layer 1402. As illustrated, the incident light 1408 polarized in a first direction (same direction as the LC molecules closest to the lower electrodes 1412) is incident on the TN LC layer 1402. The twisted arrangement of the TN LC molecules within the TN LC layer 1402 serves as an optical wave guide and rotates the plane of polarization by a quarter turn (90 degrees) prior to the light reaching the upper electrodes 1416. In this state, the TN LC layer 1402 serves to shift the polarization direction of linearly polarized light passing therethrough from one linear polarization direction to another. Thus, the transmitted light 1406A is polarized in a second direction (same direction as the LC molecules closes to the upper electrodes 1416) opposite the first direction.

On the other hand, when a voltage exceeding a threshold voltage (V>Vth) of the TN LC switchable waveplate 1404 is applied to across the electrodes 1416, 1420 (right, activated state), the TN LC molecules within the TN LC layer 1402 tend to align with the resulting electric field and the optical wave guiding property of the TN LC layer 1402 described above with respect to the deactivated state is lost. In this state, the TN LC layer 1402 serves to preserve the polarization direction of light passing therethrough. Thus, the incident light 1408 and the transmitted light 1406B are polarized in the same first direction (same direction as the LC molecules closest to the lower electrodes 1420). When the electric field is turned off, the TN LC molecules relax back to their twisted state and the TN LC molecules of the TN LC layer 1402 in the activated state returns to the configuration of TN LC molecules of the TN LC layer 1402 in the deactivated state (left).

Still referring to FIG. 14A, in operation, as described above, the polarization-selective lens stack 1300 exerts a lens power to the incident light 1420 passing therethrough depending on the polarization direction of the incident light 1420. After having or not having exerted optical power thereto, depending on the relative polarization direction of the incident light, the light is incident on the switchable waveplate 1404. As described above, the LCs of the switchable waveplate 1404 are configured such that, when activated, e.g., electrically activated, the polarization of a linearly polarized light passing therethrough is preserved, while when deactivated, e.g., electrically deactivated, the polarization of the linearly polarized light passing therethrough is altered, e.g., flipped or rotated. That is, a linearly vertical polarized (LVP) light beam is converted to a linearly horizontal polarized (UP) light beam and vice versa, or the polarization is preserved, depending on whether the switchable waveplate 1404 is activated or deactivated.

In operation, the LCs of the birefringent Fresnel lens 1304 are configured such that, when the polarization direction of linearly polarized incident light 1420 is parallel to the optic axis of the birefringent Fresnel lens 1304, the polarization-selective lens stack 1300 exerts an optical power thereto, as described above with respect to FIG. 12B, while when the polarization direction of the linearly polarized incident light 1420 is perpendicular to the optic axis, the polarization-selective lens stack 1300 exerts substantially zero optical power thereto, as described above with respect to FIG. 12C. After passing through the birefringent lens stack 1300, when activated, e.g., electrically activated, the polarization of a linearly polarized light passing through the switchable waveplate 1404 is preserved, while when deactivated, e.g., electrically deactivated, the polarization of the linearly polarized light passing through the switchable waveplate 1404 is flipped or rotated, due to rearrangement of liquid crystal molecules.

With respect to FIGS. 14A-14B, adaptive lens assemblies comprising a passive polarization-selective lens stack coupled with a waveplate (FIG. 14A) for switchably exerting lens power have been described. The inventors have recognized that, by arranging a plurality of such elements, adaptive lens assemblies having a plurality of different lens powers can be formed. Thus, in the following, embodiments of adaptive waveplate lens assemblies comprising a plurality of passive polarization-selective lens stacks coupled with waveplates are disclosed. Such adaptive lens assemblies may be integrated with a waveguide either on the user side or the world side, to form display devices described with respect to, e.g., FIGS. 11A and 11B.

Figure 15A:
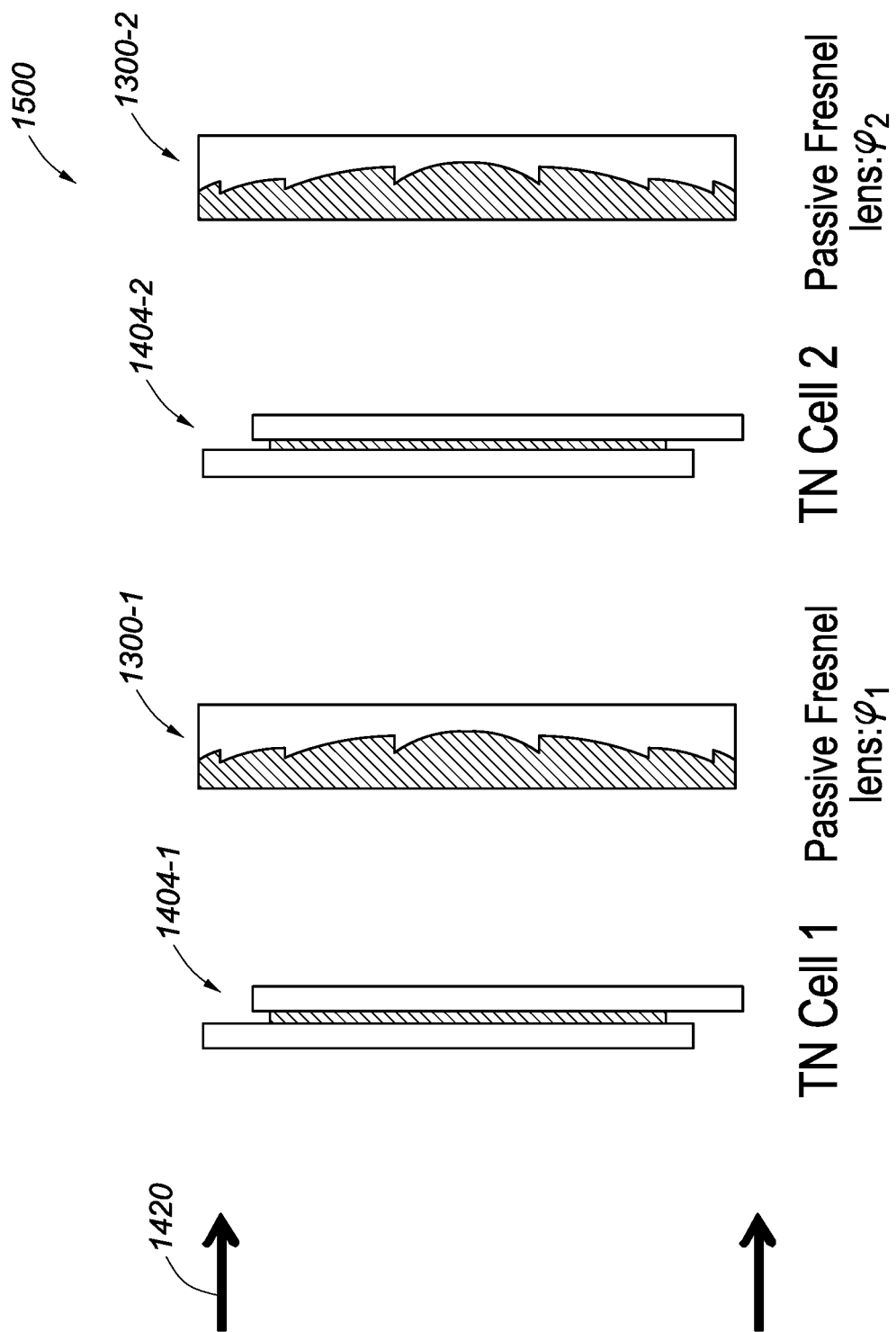
FIG. 15A illustrates a cross-sectional view of an example adaptive lens assembly comprising a first polarization-selective lens stack coupled with a first switchable waveplate comprising twisted nematic liquid crystals and a second polarization-selective lens stack coupled with a second switchable waveplate comprising twisted nematic liquid crystals.

FIG. 15A illustrates an example of an adaptive lens assembly 1500 comprising a plurality of passive polarization-selective lens stacks and a plurality of waveplates that are alternatingly arranged to exert a plurality, e.g., at least four, possible optical powers to light passing therethrough. The adaptive lens assembly 1500 comprises, in the order of light passing therethrough, a first switchable waveplate (HWP1) 1404-1, e.g., a switchable half waveplate, a first polarization-selective lens stack (L1) 1300-1, a second switchable waveplate (HWP2) 1404-2, e.g., a switchable half waveplate, and a second polarization-selective lens stack (L2) 1300-2. Each of the HWP1 1404-1 and HWP2 1404-2 is configured in a manner similar to that described above with respect to FIGS. 14A and 14B. In addition, each of the L1 1300-1 and L2 1300-2 is configured in a similar manner to that described above with respect to FIGS. 12A-12C and 13A-13B. However, the first and second polarization-selective lens stacks 1300-1, 1300-2 have different optic axes, different curvature (e.g., effective radii of curvature) and/or different birefringence. That is, the L1 1300-1 has a first optic axis (extending in a vertical or y direction) and is configured to exert a first optical power $\phi_1$ of $\Delta n_1/R_1$ or substantially zero to light incident thereon having a polarization direction parallel or perpendicular to the optic axis, respectively, while the L2 1300-2 has a second optic axis (extending in a horizontal or x-axis) and is configured to exert a second optical power $\phi_2$ of $\Delta n_2/R_2$ or substantially zero to light incident thereon having a polarization direction parallel or perpendicular to the optic axis, respectively.

Figure 15B:
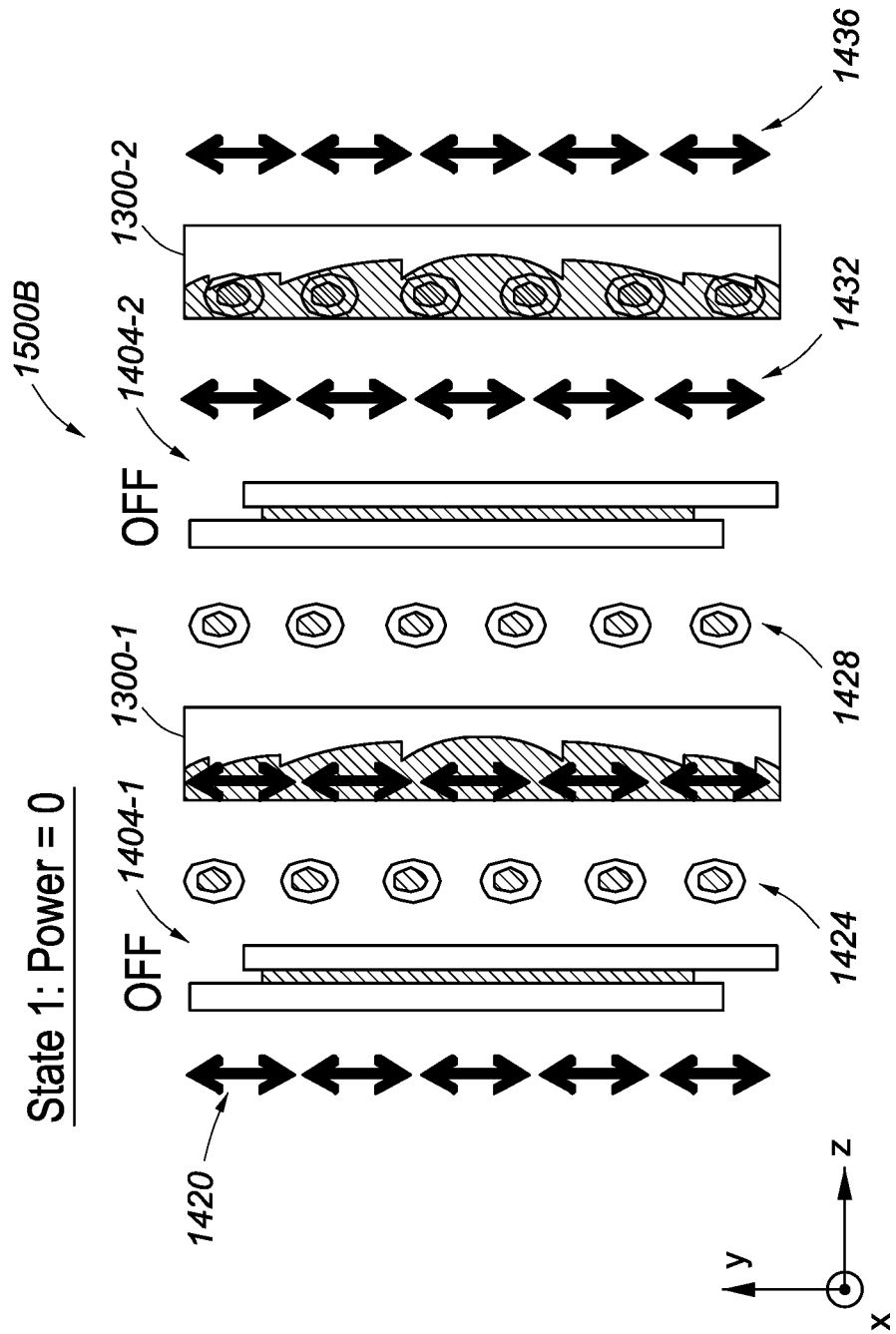
FIGS. 15B-15E illustrate the example adaptive lens assembly of FIG. 15A in operation under different configurations configured to exert different optical powers.
Figure 15C:
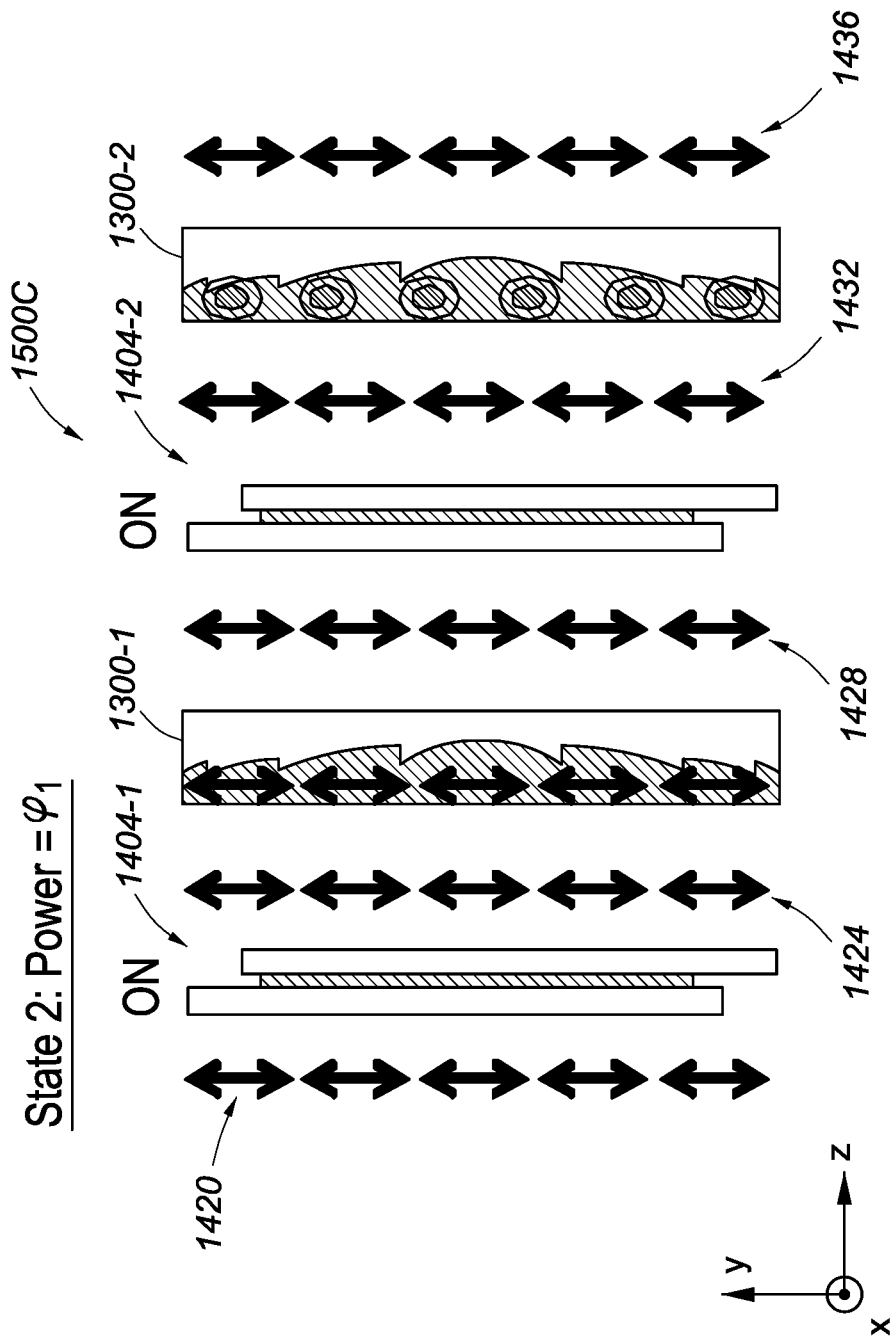
Figure 15D:
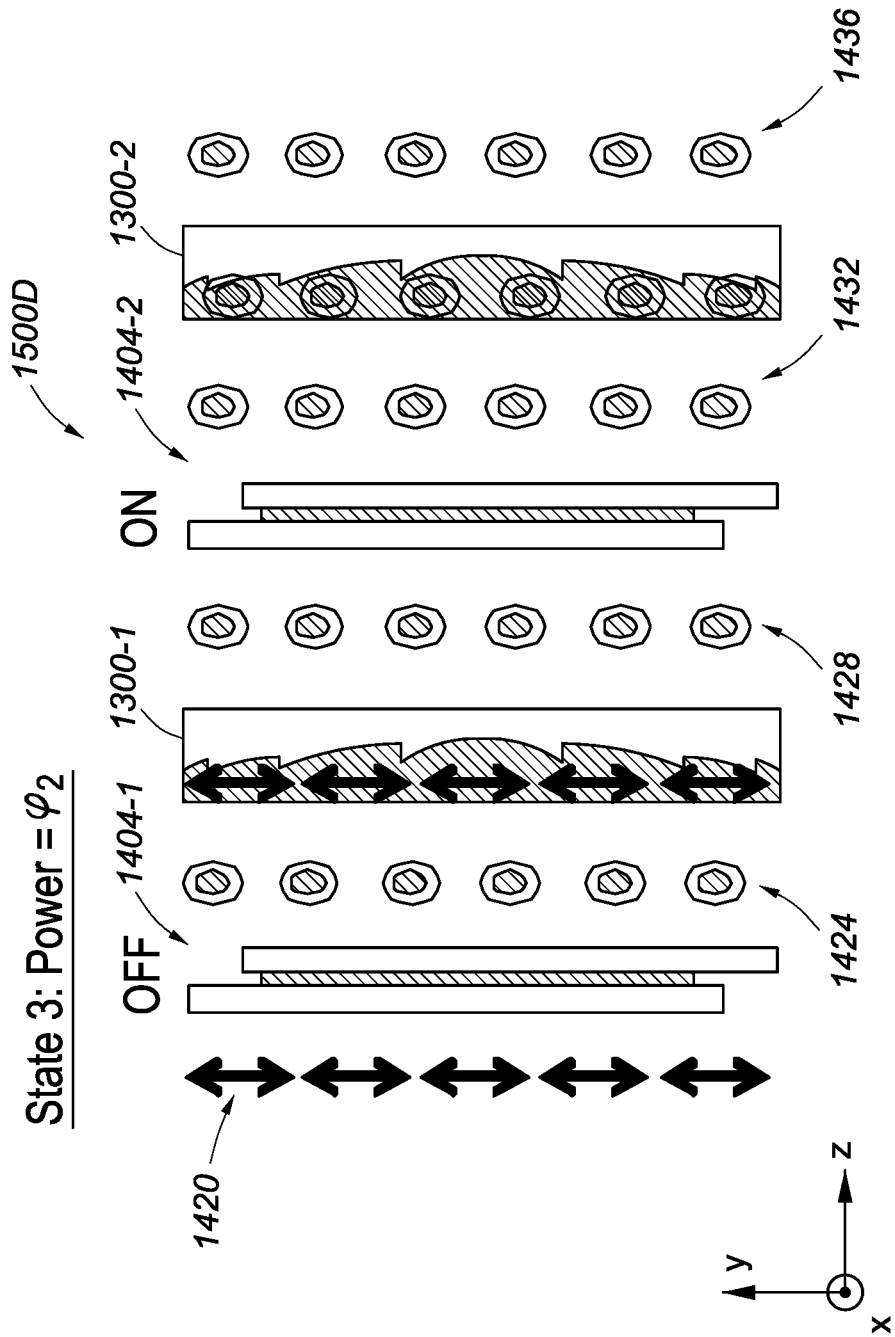
Figure 15E:
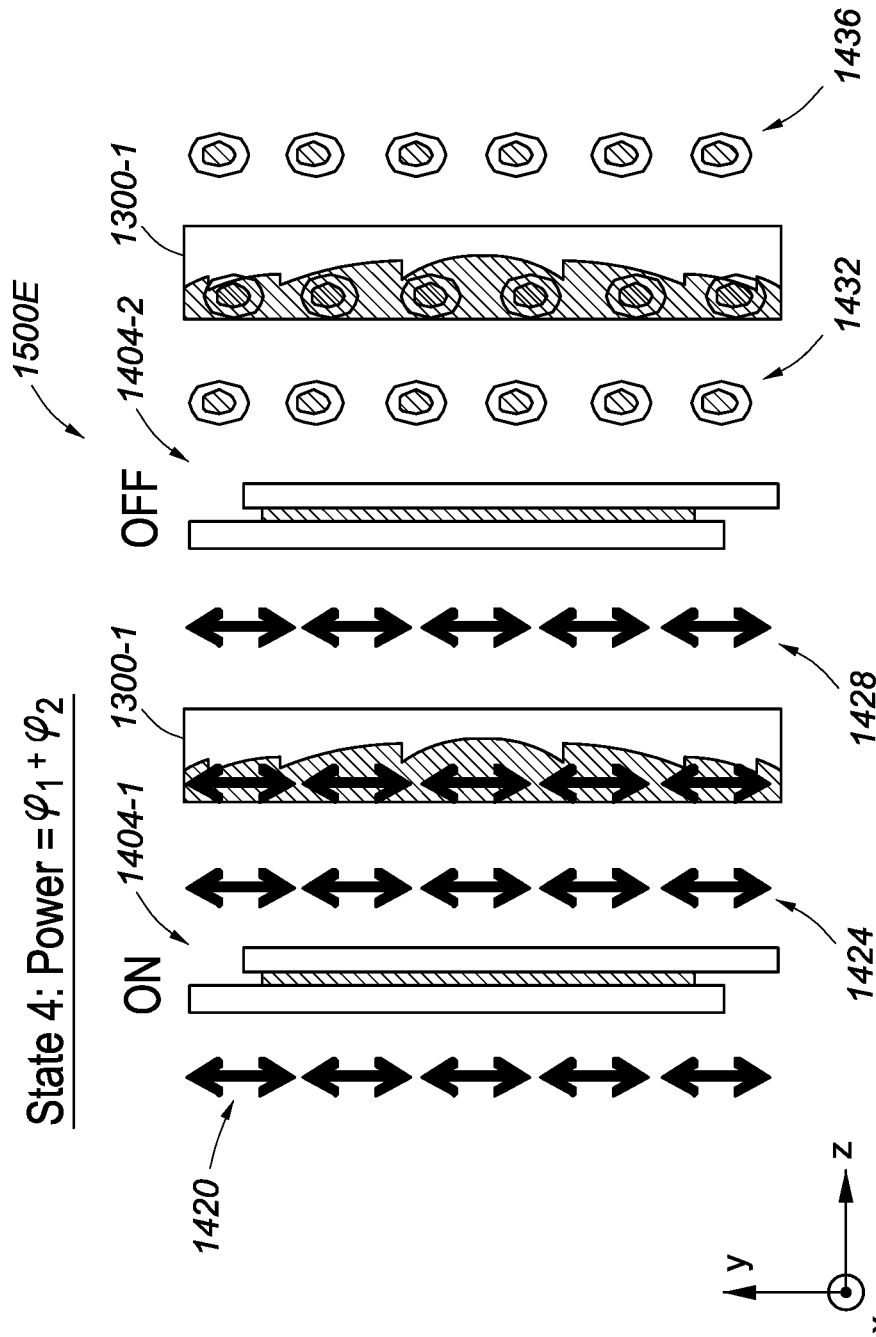

FIGS. 15B-15E illustrate the adaptive lens assembly 1500 in operation, for incident light 1420 having a polarization parallel to the optic axis of L1 1300-1, at four different states corresponding to HWP1 1404-1/HWP 1404-2 being deactivated (OFF)/deactivated (OFF) (FIG. 15B), activated (ON)/activated (ON) (FIG. 1.5C), OFF/ON (FIG. 15D), and ON/OFF (FIG. 15E). As described above, each of the HWP1 1404-1 and HWP2 1404-2 can be turned OFF and ON, or deactivated and activated, by removing and applying a voltage across the TN LC layer. Each of the HWP1 1404-1 and HWP2 1404-2 is configured to alter a polarization state, e.g., rotate or invert a polarization state, of light passing therethrough when electrically deactivated (OFF), while being configured to substantially pass light without altering the polarization state of light passing therethrough when activated (ON). The electrical signal, e.g., a current signal or a voltage signal, for switching each of the HWP1 1404-1 and HWP2 1404-2 may be provided by a switching circuit (not shown) electrically connected thereto. For illustrative purposes, in the following, both HWP1 1404-1 and HWP2 1404-2 are TN LC cells having optic axes along the y and x directions at their two substrates respectively, similar to FIG. 14B. In the illustrated embodiment, the incident light 1420 has a polarization parallel to y direction, i.e., a linear vertical polarization (LVP). However, it will be appreciated that the polarization axis the incident light 1420 can be polarized in a different direction, a linear horizontal polarization (LHP), to achieve the different optical power states.

Referring to FIG. 15B, each of the HWP1 1404-1 and HWP2 1404-2 is in the OFF state and configured to rotate the polarization of linearly polarized light having one of LVP and LHP into linearly polarized having the other of LVP and LHP. Thus, the incident light 1420 having LHP, upon passing through the HWP1 1404-1, is converted to light 1424 incident on L1 1300-1 having LHP, which exerts substantially zero optical power ($\phi_1$=0) due to the relative orthogonal orientations between the polarization of light 1424 and the optic axis of the L1 1300-1. Thereafter, light 1428 having LHP incident on the HWP2 1404-2 is converted to light 1432 having LVP. The L2 1300-2 exerts substantially zero optical power ($\phi_2$=0) due to the relative orthogonal orientations between the polarization of the L2 1300-2 and the optic axis of the L2 1300-2. In sum, the adaptive lens assembly 1500 exerts a net power $\phi_1+\phi_2$ equal to about zero to the incident light 1420 having LVP and does not after its polarization, to output light 1436 having LVP.

Referring to FIG. 15C, each of the HWP1 1404-1 and HWP2 1404-2 are in the ON state and configured to preserve the polarization of linearly polarized light passing therethrough. Thus, the polarization of incident light 1420 having LVP, upon passing through the HWP1 1404-1, is preserved into light 1424 incident on L1 1300-1, which exerts an optical power ($\phi_1$) due to the relative parallel orientations between the polarization of the light 1424 and the optical axis of the L1 1300-1. Thereafter, the polarization of light 1428 having LVP incident on the HWP2 1402-2 is preserved into light 1432. The L2 1300-2 exerts substantially zero optical power ($\phi_2$=0) due to the relative orthogonal orientations between the polarization of the light 1432 and the optic axis of the L2 1300-2. In sum, the adaptive lens assembly 1500 exerts a net power $\phi_1+\phi_2$ equal to about $\phi_1$ to the incident light 1420 having LVP to output light 1436 having LVP.

Referring to FIG. 15D, the HWP1 1404-1 is in the OFF state and configured to rotate the polarization of linearly polarized light having one of LVP and LEP into linearly polarized having the other of LVP and LHP, while the HWP2 1404-2 is in the ON state and configured to preserve the polarization of linearly polarized light. Thus, the incident light 1420 having LVP, upon passing through the HWP1 1404-1, is converted to light 1424 incident on the L1 1300-1 having LHP, which exerts substantially zero optical power ($\phi_1$=0) due to the relative orthogonal orientations between the polarization of the light 1424 and the optic axis of the L1 1300-1. Thereafter, the polarization of light 1428 having LHP passing through the HWP2 1402-2 is preserved into light 1432. The light 1432 incident on the L2 1300-2 has LHP, which exerts an optical power (412) due to the relative parallel orientations between the polarization of the light 1432 and the optic axis of the L2 1300-2. In sum, the adaptive lens assembly 1500 exerts a net power $\phi_1+\phi_2$ equal to about $\phi_2$ to the incident light 1420 having LVP to output light 1436 having LHP.

Referring to FIG. 15E, the HWP1 1404-1 is in the ON state and configured to preserve the polarization of linearly polarized light, while the HWP2 1404-2 is in the OFF state and is configured to rotate the polarization of linearly polarized light having one of LVP and LHP into linearly polarized having the other of LVP and LHP. Thus, the polarization of incident light 1420 having LVP, upon passing through the HWP1 1404-1, is preserved into light 1424 incident on the L1 1300-1 having LVP, which exerts an optical power ($\phi_1$) due to the relative parallel orientations between the polarization of the light 1424 and the optic axis of L1 1300-1. Thereafter, the light 1428 having LVP passing through the HWP2 1404-2 is converted into light 1432 having LHP. The L2 1300-2 exerts an optical power ($\phi_2$) due to the relative parallel orientations between the polarization of the light 1432 and the optic axis of the L2 1300-2. In sum, the adaptive lens assembly 1500 exerts a net power $\phi_1+\phi_2$ to the incident light 1420 having LVP to output light 1436 having LHP.

Thus, as illustrated by FIGS. 15A-15E, for light having a linear polarization, four possible net powers (0, $\phi_1$, $\phi_2$, and $\phi_1+\phi_2$) can be exerted on the light passing though the adaptive lens assembly 1500. By way of a numerical example, for $\phi_1$=0.75 D and $\phi_2$=1.5 D for the design wavelength, net optical powers of 0, 0.75 D, 1.5 D, and 2.25 D can be obtained using the adaptive lens assembly 1500.

Still referring to FIGS. 15A-15E in conjunction with FIGS. 11A-11B, in the illustrated embodiment, the incident light 1420 may represent a light beam incident on either the first adaptive lens assembly 1004 (FIGS. 11A-11B on the world side) or the second adaptive lens assembly 1008 (FIGS. 11A-11B on the user side). By placing the adaptive lens assembly 1500 on either or both sides, display systems described above, e.g., with respect to FIGS. 11A-11B, can be implemented, according to various embodiments described herein.

Display Devices Including Adaptive Lens Assemblies Having Polarization-Selective Lens Stack Coupled to Nonpolarizing Waveguide Assembly In the following example implementations, an adaptive lens assembly comprising a plurality of switchable polarization-selective lens stacks (e.g., the adaptive lens assembly 1500, FIGS. 15A-15E) has been integrated into a display device, such as for example, a display device such as described supra with respect to FIGS. 10, 11A and 11B.

Figure 16:
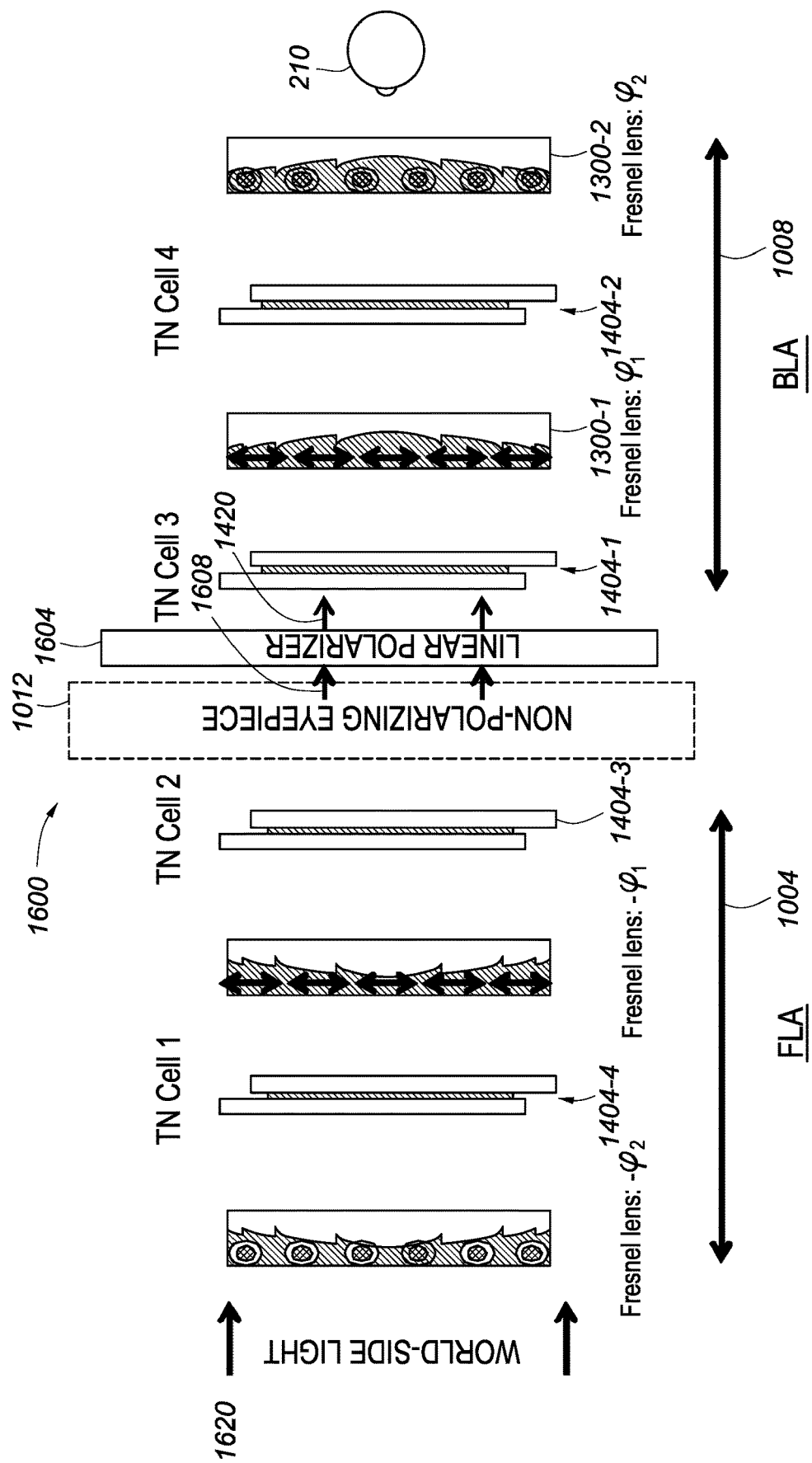
FIG. 16 illustrates a cross-sectional view of an example display device comprising a waveguide assembly interposed between a first adaptive lens assembly and a second adaptive assembly each having a polarization-selective lens stack.

FIG. 16 illustrates an example display device 1600 including a waveguide assembly 1012 interposed between a first or front adaptive lens assembly (FLA) 1004 and a second or back adaptive lens assembly (BLA) 1008. The overall configuration of the display device 1600 can be similar to the display device 1100A/1100B described above with respect to FIGS. 11A/11B. In the illustrated embodiment, the BLA 1008 is configured similarly to the adaptive lens assembly 1500 described above with respect to FIGS. 15A-15E, and includes a first switchable waveplate (HWP1) 1404-1, a first polarization-selective lens stack (L1) 1300-1, a second switchable waveplate (HWP2) 1404-2 and a second polarization-selective lens stack (L2) 1300-2. The first and second polarization-selective lens stacks 1300-1, 1300-2 have different, e.g., orthogonal optic axes, curvature (e.g., effective radii of curvature) and/or different birefringence, such that L1 1300-1 is configured to exert a first optical power $\phi_1$ of $\Delta n_1/R_1$ or substantially zero for light incident thereon having a polarization direction parallel or perpendicular to the optic axis, respectively, while the L2 1300-2 is configured to exert a second optical power $\phi_2$ of $\Delta n_2/R_2$ or substantially zero for light incident thereon having a polarization direction parallel or perpendicular to the optic axis, respectively.

The FLA 1004 includes a third switchable waveplate 1404-3, a third polarization-selective lens stack (L3) 1300-3, a fourth switchable waveplate (HWP4) 1404-4 and a fourth polarization-selective lens stack (L4) 1300-4. The third and fourth polarization-selective lens stacks 1300-3, 1300-4 have different, e.g., orthogonal optical axes, effective radii of curvature and/or different birefringence, such that L3 1300-3 is configured to exert a third optical power $\phi_3$ of $\Delta n_3/R_3$ or substantially zero to light incident thereon having a polarization direction parallel or perpendicular to the optic axis, respectively, while the L4 1300-4 is configured to exert a fourth optical power $\phi_4$ of $\Delta n_4/R_4$ or substantially zero to light incident thereon having a polarization direction parallel or perpendicular to the optic axis, respectively.

In various embodiments, the effective radii of curvature of L1 1300-1 and L2 1300-2 are such that the $\phi_1$ and $\phi_2$ have a first sign, e.g., positive sign, while the effective radii of curvature of L3 1300-3 and L4 1300-4 are such that the $\phi_3$ and $\phi_4$ have a second sign opposite the first sign, e.g., negative sign. That is, when the three possible non-zero net powers ($\phi_1$, $\phi_2$, and $\phi_1+\phi_2$) of the FLA 1004 may have one of converging or diverging effects (e.g., converging), the three possible non-zero net powers ($\phi_3$, $\phi_4$, and $\phi_3+\phi_4$) of the BLA 1008 may have the other of converging or diverging effects (e.g., diverging). In the illustrated embodiment, the FLA 1004 and the BLA 1008 are configured to be substantially the same, except for the curvatures of the interface between the birefringent and isotropic lenses (e.g., one is concave and other is convex or vice versa, etc.). In particular, the first adaptive lens assembly 1004 and the second adaptive lens assembly 1004 can be considered to form mirror images about the waveguide assembly 1012. Thus, as configured, L1 1404-1 and L3 1404-3 have optical powers $\phi_1$ and $\phi_3$, respectively, that are substantially the same in magnitude but opposite in sign, and L2 1404-2 and L4 1404-4 have optical powers $\phi_2$ and respectively, that are substantially the same in magnitude but opposite in sign. That is, $\phi_1$ is about equal to $-\phi_3$, and $\phi_2$ is about equal to $-\phi_4$.

Still referring to FIG. 16, in the illustrated embodiment, the waveguide assembly 1012 is configured to outcouple unpolarized light that has been totally internally reflected. In this configuration, the display device 1600 additionally includes a linear polarizer 1604 between the waveguide assembly 1012 and the BLA 1008 configured to reduce or eliminate, e.g., reflect or absorb, light having polarization state that does not lead to lens action by the BLA 1008. For example, in arrangements where light 1608 outcoupled from the waveguide assembly 1012, or light 1620 transmitted through the FLA 1004 unaffected is not linearly polarized, e.g., not LVP, the linear polarizer 1604 serves to linearly polarize the transmitted light to feed the incident light 1420 into the BLA 1008.

As configured, the BLA 1008 serves to provide variable optical powers ($\phi_1$, $\phi_2$, and $\phi_1+\phi_2$) to form images at a plurality of depth planes for the virtual images exiting the waveguide assembly 1012 towards the eye 210. While the BLA 1008 provides virtual images by focusing images from the waveguide assembly 1012 at a plurality of depth planes, the world image can be distorted by the BLA 1008. The FLA 1004 serves to compensate the distortion of the world image caused by the BLA 1008 by providing variable optical powers (e.g., $\phi_3=-\phi_1$, $\phi_4=-\phi_2$ and $\phi_3+\phi_4=-(\phi_1+\phi_2)$), such that the world image is presented to the eye 210 without substantial distortion.

In various embodiments, e.g., when deactivated, each of the FLA 1004 and BLA 1008 may provide a net optical power (positive or negative) in the range between about ±5.0 diopters and 0 diopters, ±4.0 diopters and 0 diopters, ±3.0 diopters and 0 diopters, ±2.0 diopters and 0 diopters, ±1.0 diopters and 0 diopters, including any range defined by any of these values, for instance 1.5 diopters. In some embodiments, the FLA 1004 between the waveguide assembly 1012 and the world may have a positive optical power, whereas the BLA 1008 between the waveguide assembly 1012 and the user may have a negative optical power, such that the optical powers of the FLA 1004 and BLA 1008 compensate each other in viewing the world.

As described supra, as the images of virtual objects produced by light outcoupled by the waveguide assembly 1012 move in 3D, the net optical power of the BLA 1008 on the user side is adjusted to adapt to the changing depth of the virtual depth plane. Simultaneously, according to embodiments, the net optical power of the FLA 1004 is correspondingly adjusted using a switching circuit, such that the view of the real world does not undesirably become defocused or distorted. To address this and other needs, in some embodiments, the display device 1600 comprises a controller (not shown) configured such that, when the net optical power of one of the FLA 1004 and BLA 1008 is electrically adjusted, the net optical power of the other of the FLA 1004 and BLA 1008 is correspondingly adjusted such that the combined net optical powers remain about constant, e.g., about zero. The controller circuitry and the switchable waveplates are configured such that the time to switch the HWP1 1404-1, HWP2 1404-2, HWP3 1404-3 and HWP4 1404-4, to adjust the virtual depth planes using the second adaptive lens assembly 1008 and to compensate the real world view using the first adaptive lens assembly 1004, is less than about 100 milliseconds, less than about 50 milliseconds, less than about less than about 10 milliseconds, less than about 5 milliseconds, less than about 1 millisecond, or a value within a range defined by any of these values.

Display Devices Including Adaptive Lens Assemblies Having Polarization-Selective Lens Stack Configured to Recycle Light for Improved Optical. Efficiency As described above, adaptive lenses can be used to focus virtual images at a plurality of depth planes. However, adaptive lens stacks according to embodiments comprise polarization-selective lens stacks. As a result, some display devices having polarization-selective lens stacks may lose as much as or even greater than 50% in brightness due to the loss of light having non-transmitting polarization. Thus, there is a need for efficient conversion of virtual image polarization to make compact/light-efficient variable focus light-field displays. According to embodiments, display devices having improved optical efficiency are described, that employ polarization-selective lens stacks in combination with notch reflectors to recycle light having non-transmitting polarization.

As described herein, a notch reflector generally refers to a light reflector that transmits most wavelengths of light substantially unaltered, while reflecting light in a specific range of wavelengths with relatively high efficiency. The specific range of wavelengths where light is reflected is termed the "notch." Notch reflectors can be formed from multiple dielectric layers (a multi-layer), liquid crystals, metamaterials or metastructures, etc. Notch reflectors can include diffractive optical elements, surface or volumetric holograms, etc. Notch reflectors can be laminated onto a substrate material (e.g., polymer or glass). In some of the implementations described herein, to reflect RGB light, the reflector comprises multiple notch reflectors, with the notch in each reflector tuned to one of the specific RGB colors (e.g., a reflector comprising an R-notch reflector, a G-notch reflector, and a B-notch reflector). Accordingly, the wavelength range of each notch can match the wavelength range of the light injected into the display (e.g., the R-notch is matched to the wavelength range of the red light injected by a red LED or laser, and similarly for the G and B notches).

Various embodiments described herein comprise a notch reflector that includes a transmissive substrate, e.g., a polished glass or polymer substrate, having formed thereon one or more optical layers. The one or more optical layers are configured to notch-reflect light having a wavelength range $\Delta\lambda$ of about 40 nm, about 70 nm, about 100 nm or about 150 nm or any range between any of these values, whose range is centered around a red light including light of one or more wavelengths in the range of about 620-780 nm, a green light including light of one or more wavelengths in the range of about 492-577 nm, or blue light including light of one or more wavelengths in the range of about 435-493 nm. In some embodiments, the wavelength range $\Delta\lambda$ may substantially cover the red light range of about 620-780 nm, the green light range of about 492-577 nm, or blue light range of about 435-493 nm.

Various embodiments described herein comprise a notch reflector configured as a polarization notch reflector. Within the notch-reflective range, a polarizing notch reflector allows light having one polarization to substantially pass therethrough, while substantially reflecting light having the opposite polarization. For example, when light having both left-hand circular polarization (LHCP) and right-hand circular polarization (RHCP) within the notch-reflective range is incident on a polarizing notch reflector, the notch reflector can substantially reflect light having one of the RHCP and LHCP, while substantially passing light having the opposite one of the RHCP and LHCP. Similarly, when light having both linear vertical polarization (LVP) and linear horizontal polarization (LHP) is incident on a polarizing notch reflector, the notch reflector can substantially reflect light having one of the LVP and LHP, while substantially passing light having the opposite one of the LVP and LHP.

Various embodiments described herein additionally comprise a notch reflector configured as a non-polarizing notch reflector. Within the notch-reflective range, a non-polarizing notch reflector substantially reflects light incident thereon regardless of its polarization. For example, when light having both LHCP and RHCP within the notch-reflective range is incident on a non-polarizing notch reflector, the notch reflector can substantially reflect light having both the RHCP and LHCP. Similarly, when light having both LVP and LHP is incident on a polarizing notch filter, the notch filter can substantially reflect light having both the LVP and LHP.

In various embodiments described herein, a notch reflector configured as a polarizing or non-polarizing notch reflector can also be configured as a polarization-converting notch reflector. Within the notch-reflective range, upon reflecting light having a polarization, the polarization-converting notch reflector converts the polarization of the reflected light to an opposite polarization. For example, when light having one of LHCP and RHCP within the notch-reflective range is incident on a polarization-converting notch reflector, the notch reflector converts the one of the RHCP and LHCP into an opposite one of the RHCP and LHCP. Similarly, when light having one of LVP and LHP is incident on a polarization converting notch reflector, the notch reflector converts one of the LVP and LHP into an opposite one of the LVP and LHP.

As described herein, within the notch-reflective range ($\Delta\lambda$), a notch reflector configured to reflect light having one or more polarizations can be configured to reflect substantially all of the light having the one or more polarizations incident thereon. For example, when a notch reflector is configured to reflect light having one or both of the RHCP and LHCP, the notch reflector may reflect, e.g., greater than 80%, greater than 90%, greater than 95%, greater than 99%, greater than 99.99%, greater than 99.999%, or greater than 99.9999% of the light having the one or both of the RHCP and LHCP incident thereon. On the other hand, when a notch reflector is configured to reflect light having one of the RHCP and LHCP, the notch reflector may reflect, e.g., greater than 80%, greater than 90%, greater than 95%, greater than 99%, greater than 99.99%, greater than 99.999%, or greater than 99.9999% of the light having the one of the RHCP and LHCP incident thereon. Conversely, the notch reflector is configured such that light that is not reflected, e.g., light having a wavelength outside the notch-reflective range ($\Delta\lambda$) or a polarization that the notch reflector is not configured to reflect, is substantially entirely transmitted, e.g., greater than 80%, greater than 90%, greater than 95%, greater than 99%, greater than 99.99%, greater than 99.999%, or greater than 99.9999% of the light incident thereon being transmitted.

Figures 17A, 17B:
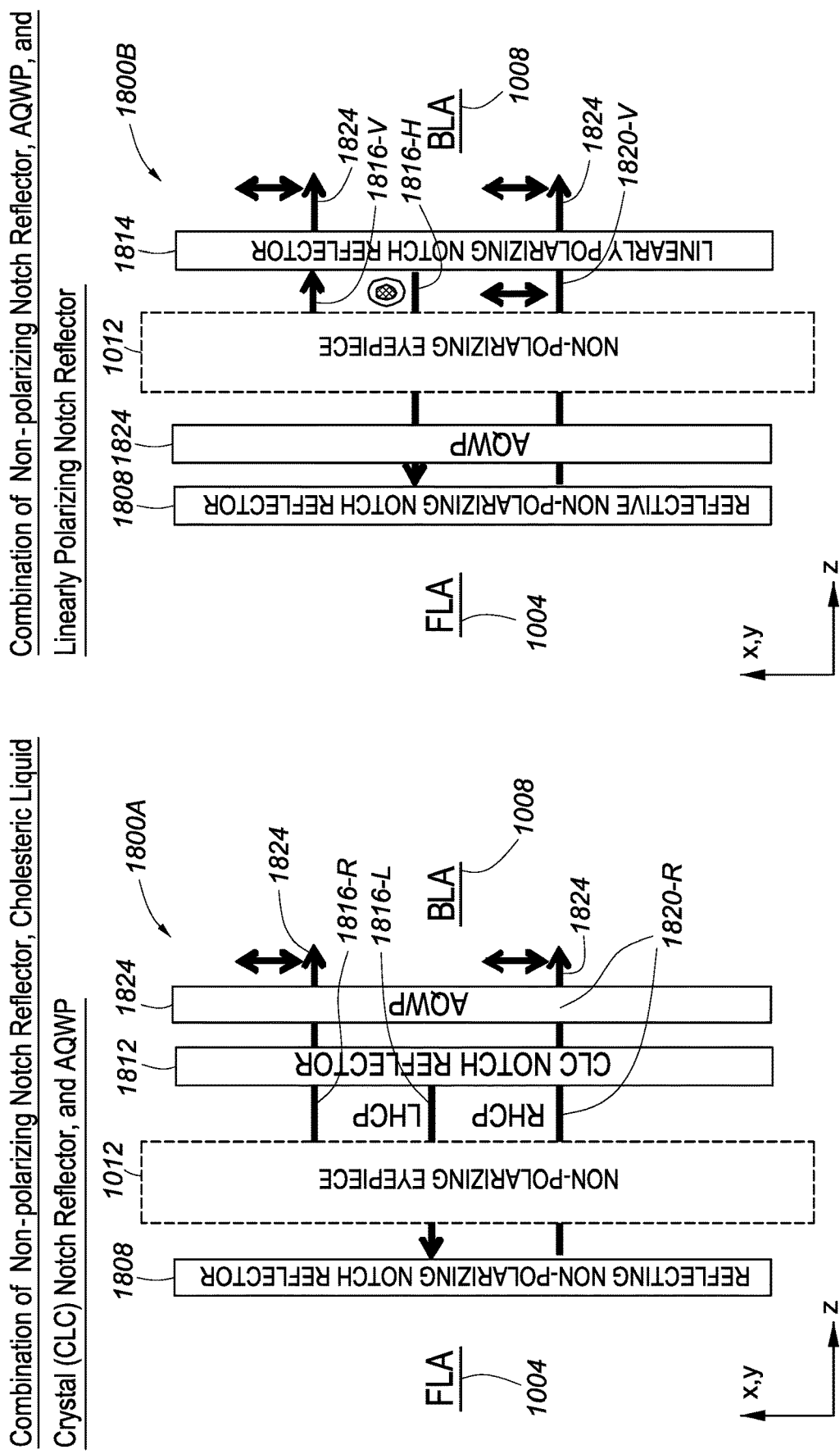
FIG. 17A illustrates a cross-sectional view of an example display device configured to display images using light outcoupled from the waveguide assembly having different circular polarizations.
FIG. 17B illustrates a cross-sectional view of an example display device configured to display images using light outcoupled from the waveguide assembly having different linear polarizations.

FIG. 17A illustrates a display device 1800A comprising an adaptive lens assembly configured to recycle light having non-transmitting polarization, according to embodiments.

The display device 1800A comprises a waveguide assembly 1012, e.g., a non-polarizing waveguide assembly, interposed between a FLA 1004 and BLA 1008, in a similar manner as described above with respect to FIG. 16. The display device 1800A further comprises a non-polarizing notch reflector 1808 interposed between the FLA 1004 and the waveguide assembly 1012, and a polarizing notch reflector 1812 interposed between the BLA 1008 and the waveguide assembly 1012.

Still referring to FIG. 17A, the non-polarizing notch reflector 1808 according to embodiments is configured such that, within the notch-reflective range, the notch reflector 1808 substantially reflects light incident thereon regardless of its polarization. Furthermore, in the illustrated embodiment, the non-polarizing reflector 1808 is configured as a polarization-converting notch reflector configured such that, within the notch-reflective range, upon reflecting light having a polarization, the polarization-converting notch reflector converts the polarization of the reflected light to an opposite polarization. The non-polarizing notch reflector 1808 includes a transmissive substrate, e.g., a polished glass or polymer substrate, having formed thereon one or more optical layers. In some embodiments of the notch reflectors described herein, the one or more optical layers formed on a substrate can include one or more dielectric coatings, whose combination gives rise to the various notch-reflective characteristics described above.

Still referring to FIG. 17A, the polarizing notch reflector 1812 according to embodiments is configured such that, within the notch-reflective range, the polarizing notch reflector 1812 substantially reflects light incident thereon in a polarization-selective manner. Furthermore, in the illustrated embodiment, the polarizing reflector 1812 is configured such that, unlike the non-polarizing notch reflector 1808, the notch reflector 1812 does not convert the polarization of the reflected light to an opposite polarization. The polarizing notch reflector 1812 includes a transmissive substrate, e.g., a polished glass or polymer substrate, having formed thereon one or more optical layers. In some embodiments, the one or more optical layers formed on a substrate can include one or more cholesteric liquid crystal (CLC) layers.

Still referring to FIG. 17A, the polarizing notch reflector 1812 comprises a CLC layer having LC molecules arranged as a plurality of chiral structures. In certain implementations, each of the chiral structures comprises a plurality of LC molecules that extend in a layer depth direction by at least a helical pitch and are successively rotated in a rotation direction. Without subscribing to any scientific theory, in various implementations, the CLC layer can advantageously be configured to substantially Bragg-reflect elliptically or circularly polarized light having a handedness of polarization that is matched to the rotation direction of the liquid crystal molecules, while being configured to substantially transmit elliptically or circularly polarized light having a handedness of polarization that is opposite to the rotation direction of the liquid crystal molecules. As configured, when incident light having a combination of light beams having LHCP and RHCP are incident on the polarizing notch reflector 1812, by Bragg-reflection, light with one of the circular polarization handedness is reflected by the polarizing notch reflector, while light with the opposite polarization handedness is transmitted therethrough without substantial interference. As described herein and throughout the disclosure, the handedness is defined as viewed in the direction of propagation.

In operation, the light out-coupled from the waveguide assembly 1012 includes a circularly polarized light beams 1816-L having LHCP and 1816-R having RHCP. The light beams 1816-L having LHCP and 1816-R having RHCP travel, e.g., in a positive z-direction, until the beams impinge on the polarizing notch reflector 1812. In the illustrated embodiment, the liquid crystal molecules of the chiral structures are rotated in a clockwise direction successively in the same rotation direction as the light beams 1816-R. As a result, the light beam having LHCP incident on the polarizing notch reflector 1812 is substantially reflected therefrom, as 1816-L, whereas the light beam 1816-R having RHCP is substantially transmitted through the polarizing notch reflector 1812.

The 1816-R transmitted through the polarizing notch reflector 1812 passes through a quarter waveplate (QWP) 1824, which converts the light beam 1816-R into a linear polarized light 1824 having LVP to enter the eye 210. On the other hand, the light beam 1816-L reflected by the polarizing notch reflector 1812 propagates toward the non-polarizing notch reflector 1808 and is substantially reflected therefrom, into a light beam 1820-R having the opposite polarization handedness, i.e., RHCP, due to the polarization-converting characteristics of the non-polarizing notch reflector 1808. The resulting light beam 1820-R having RHCP is substantially transmitted through the waveguide assembly 1012 and the polarizing notch reflector 1812, followed by a quarter waveplate (QWP) 1824, which converts the light beam 1820-R into a linear polarized light 1824 having LVP to enter the eye 210.

FIG. 17B illustrates a display device 1800B comprising an adaptive lens assembly configured to recycle light having non-transmitting polarization, according to some other embodiments. Similar to the display device described above with respect to FIG. 17A, the display device 1800B comprises a waveguide assembly 1012, e.g., nonpolarizing waveguide assembly, interposed between a FLA 1004 and a BLA 1008, and a non-polarizing notch reflector 1808 and a quarter waveplate (QWP) 1824 interposed between the FLA 1004 and the waveguide assembly 1012. The display device 1800B additionally includes a polarizing notch reflector 1814, e.g., a linear polarizing notch reflector, interposed between the waveguide assembly 1012 and the BLA 1812.

Still referring to FIG. 17B, similar to the polarizing notch reflector 1812 described above with respect to FIG. 17A, the polarizing notch reflector 1814 is configured such that, within the notch-reflective range, the notch reflector 1814 substantially reflects light incident thereon in a polarization-selective manner. Furthermore, unlike the non-polarizing notch reflector 1808, the polarizing reflector 1814 does not convert the polarization of the reflected light to an opposite polarization.

In addition, unlike the polarizing notch reflector 1812 (FIG. 17A), the polarizing notch reflector 1814 does not include a CLC layer. Instead, the polarizing notch reflector 1814 includes a transmissive substrate, e.g., a polished glass or polymer substrate, having formed thereon one or more optical layers. In some embodiments of the notch reflectors described herein, the one or more optical layers formed on a substrate can include one or more dielectric coatings, whose combination gives rise to the various notch-reflective characteristics described above.

Still referring to FIG. 17B, in operation, light out-coupled from the waveguide assembly 1012 includes linearly polarized light beams 1816-V having LVP and 1816-H having LHP. The light beams 1816-V and 1816-H travel, e.g., in a positive z-direction, until the beams impinge on the polarizing notch reflector 1814. Thereupon, the light beam 1816-H is substantially reflected off the polarizing notch reflector 1814, whereas the light beam 1816-V is substantially transmitted therethrough, to enter the eye 210.

The light beam 1816-H is reflected by the polarizing notch reflector 1814 and propagates toward and is transmitted through the quarter-wave plate 1824, to be reflected off of the non-polarizing notch reflector 1808 and further transmitted through the quarter-wave plate 1824 as a light beam 1820-V having the opposite polarization handedness, e.g., LVP, due to the polarization-converting characteristics of the non-polarizing notch reflector 1808. The resulting light beam 1820-V is substantially transmitted through the polarizing notch reflector 1814, to enter the eye 210.

Although notch reflectors have been discussed in examples above wherein the notch filter selectively alters the polarization state for certain polarizations of light, polarization elements other than notch reflectors may be use. Such polarization elements may, for example, alter the polarization state over a wide range of wavelengths.

Adaptive Lens Assemblies Comprising Switchable Polarization-Selective Lens Stack According to various embodiments disclosed herein, adaptive lens assemblies can generate images at multiple depth planes by selectively switching between a plurality of states with different optical powers. In the above, e.g., with respect to FIGS. 14A-14B and 15A-15E, adaptive lens assemblies in which selective switching is performed by activating or deactivating a switchable waveplate coupled to a polarization-selective lens were described. In some embodiments, the polarization-selective lens itself can be configured to be directly switchable, thereby allowing further simplification and/or compact integration of the adaptive lens assembly. In the following, adaptive lens assemblies in which selective switching is performed by activating or deactivating a switchable polarization-selective lens stack, instead of switching a switchable waveplate coupled thereto, according to embodiments.

As described above, some LC molecules can alter their orientation, e.g., rotate and/or tilt, e.g., under an electrical stimulus, which results in alteration of the optical properties. In some embodiments, the polarization-selective lens stack can be configured to be switchable in part by employing reactive mesogens (RMs) comprising unpolymerized LC molecules.

FIG. 18 illustrates a switchable polarization-selective lens stack 1900 comprising a polarization-selective lens stack 1904 formed between transparent electrodes 1916, 1920. The polarization-selective lens stack 1904 comprises a birefringent Fresnel lens 1304 and an isotropic lens 1308. Thus, the polarization-selective lens stack 1904 is similar to those described above, e.g., with respect to FIGS. 12A-12C and 13A-13B, except, instead of having a birefringent lens formed of polymerized LCs, the birefringent lens 1304 of the polarization-selective lens stack 1904 comprises or is formed of RMs having unpolymerized LC molecules that can alter their orientations under electric field. As configured, the switchable polarization-selective lens stack 1900 can perform similar functionalities as the combination of a passive polarization-selective lens stack and a switchable waveplate, as described above, e.g., with respect to FIG. 14A. That is, in operation, in the OFF state, e.g., in the absence of a voltage between the electrodes 1916, 1920, the LC molecules may be arranged in the same manner as described above with respect to FIGS. 12A-12C. Under this configuration, in a similar manner as described above with respect to FIG. 14A, in operation, the LCs of the polarization-selective lens stack 1904 are configured such that, when the polarization direction of linearly polarized incident light 1420, e.g., LVP light, incident thereon is parallel to the optic axis, the polarization-selective lens stack 1904 exerts an optical power thereto to output light 1436 having LVP, while when the polarization direction of linearly polarized incident light incident thereon is perpendicular to the optic axis, the polarization-selective lens stack 1904 exerts substantially zero optical power thereto. Thus, the switchable polarization-selective lens stack 1904 functions in a similar manner as a combination of a passive polarization selective lens stack and a switchable waveplate, as described above. However, in the ON state, e.g., in the presence of a voltage between the electrodes 1916, 1920, the polarization-selective lens stack 1904 can be configured to exert a varying optical power to linearly polarized light having a polarization direction that is parallel to the optic axis. The varying optical power can be caused by the LCs of the polarization-selective lens stack 1904 that are configured such that the birefringence is a function of voltage applied across the electrodes 1916, 1920, e.g., due to voltage-dependent tilt of the LC molecules (i.e., $\Delta n = f(V)$). On the other hand, for linearly polarized light having a polarization direction that is perpendicular to the optic axis, the polarization-selective lens stack 1904 exerts a zero or nearly zero optical power. The latter (zero or nearly zero optical power) can be accomplished by matching the index of the isotropic lens 1308 to the index of the birefringent lens 1304. In this manner, the optical power of the polarization-selective lens stack 1904 can be controlled by the applied voltage instead of stacking the combination of a passive polarization-selective lens stack and the switchable waveplate, as described above, e.g., with respect to FIG. 14A. However, other optical powers are possible, e.g., by not matching the index of the isotropic lens 1308 to the index of the birefringent lens 1304. Such implementation may be desirable, e.g., when the user normally benefits from wearing corrective lenses such as prescription lenses or glasses. For these users, a partial compensation may be desirable for the polarization-selective lens stack to serve at least partially as corrective lenses.

Display Devices Including Adaptive Lens Assemblies Having Switchable Polarization-Selective Lens Stack Coupled to Nonpolarizing Waveguide Assembly In the following, example display device described supra with respect to FIGS. 10, 11A and 11B, in which an adaptive lens assembly comprising a switchable polarization-selective lens stack (e.g., the polarization-selective lens stack 1904, FIG. 18) described above has been integrated, according to some embodiments.

Figure 19:
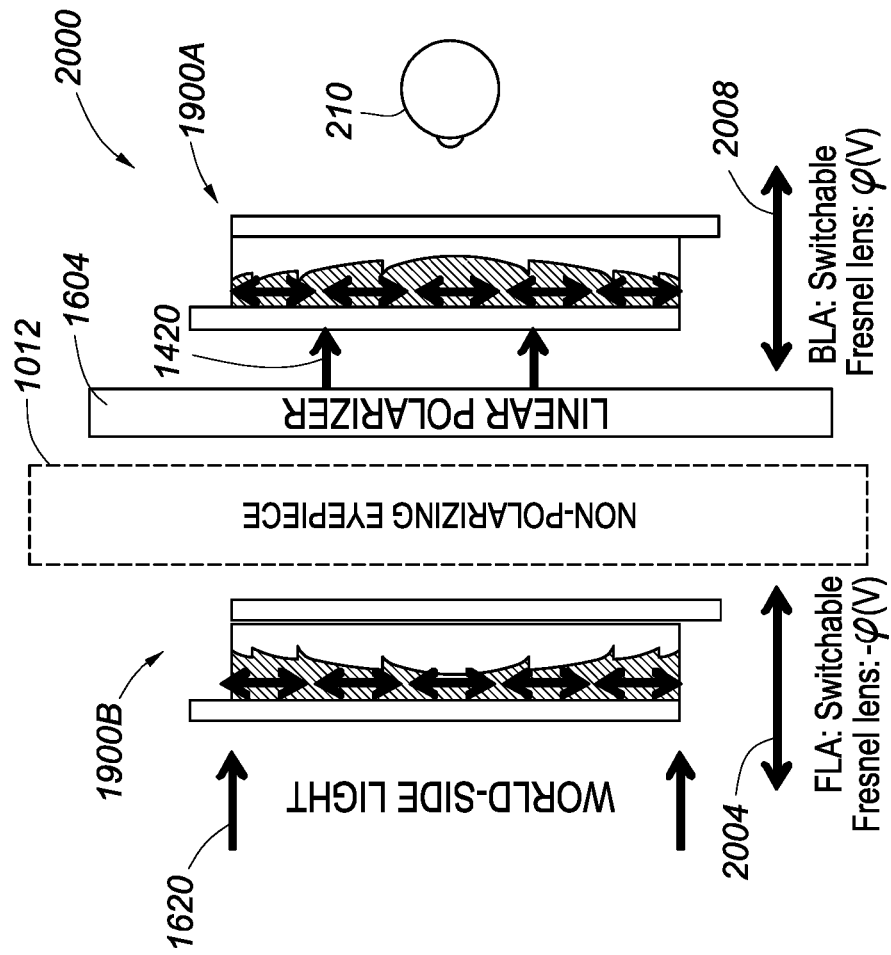
FIG. 19 illustrates a cross-sectional view of an example display device comprising a waveguide assembly interposed between a first adaptive lens assembly and a second adaptive assembly each having a switchable polarization-selective lens stack.

FIG. 19 illustrates an example display device 2000, similar to the display device described above with respect to FIG. 16, including a waveguide assembly 1012, e.g., a non-polarizing waveguide assembly, interposed between a first adaptive lens assembly (FLA) 2004 and a second adaptive lens assembly (BLA) 2008, and a linear polarizer 1604. However, unlike the FLA 1004 and BLA 1008 of the display device in FIG. 16, each of the FLA 2004 and BLA 2008 has a switchable polarization-selective lens stack similar to that described above with respect to FIG. 18. That is, the combination of switchable waveplates and the lens stacks included in the FLA 1004 and BLA 1008 of FIG. 16 are replaced with first and second switchable polarization-selective lens stacks 1900A and 1900B, respectively.

In operation, the BLA 2008 is configured to focus virtual images by exerting an optical power $\phi$ to linearly polarized light 1420, e.g., having LVP, from the waveguide assembly 1012, using the first switchable polarization-selective lens stack 1900A in the OFF state, as described above with respect to FIG. 18. In addition, in a similar manner as described above with respect to FIG. 16, to prevent the world image from being distorted by the optical power of the BLA 2008, the FLA 2004 serves to compensate by providing a compensating optical power $-\phi$ (by having the switchable polarization-selective lens stack 1900B in the OFF state), such that the world image is presented to the eye 210 without substantial distortion.

Figure 20:
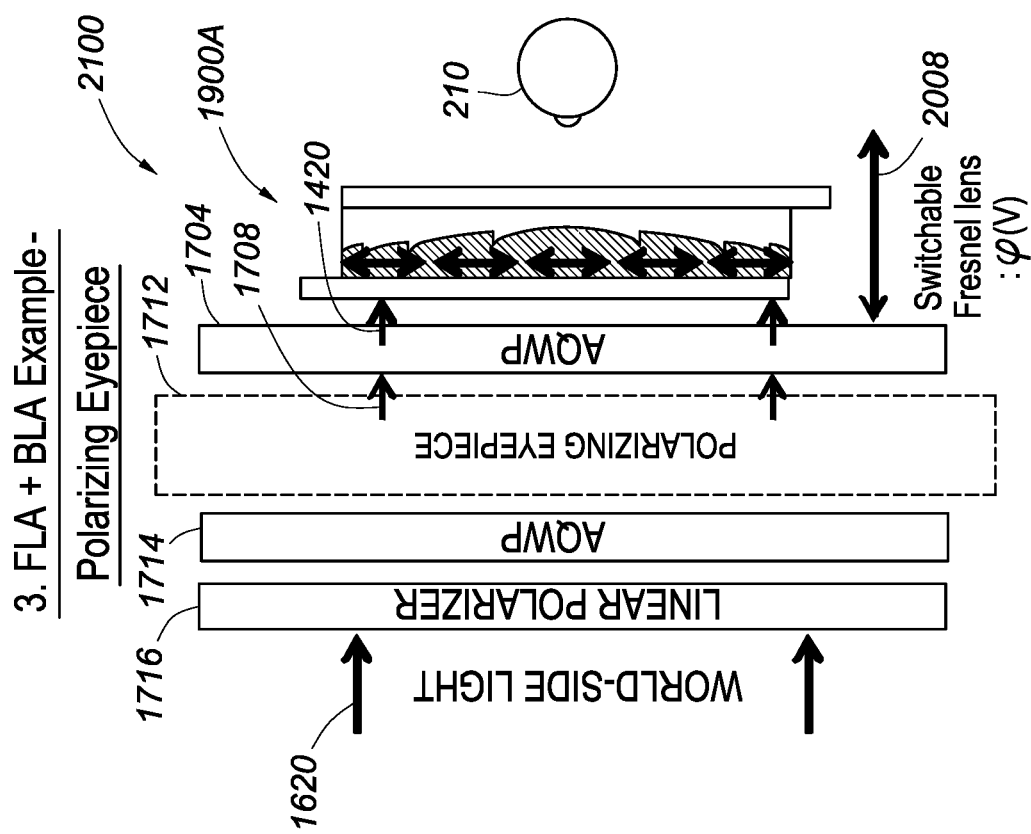
FIG. 20 illustrates a cross-sectional view of an example display device comprising a waveguide assembly interposed between a linear polarizer and a quarter wave plate on a first side and an adaptive assembly having a switchable polarization-selective lens stack on a second side.

FIG. 20 illustrates an example display device 2100, similar to the display device described above with respect to FIG. 19, including a waveguide assembly and a second adaptive lens assembly (BLA) 2008. However, unlike the display device described above with respect to FIG. 19, the display device 2100 includes a polarizing waveguide assembly 1712 that outcouples polarized light, e.g., circularly polarized light 1708-R or 1708-L, into the BLA 2008. The polarizing waveguide assembly 1712 can comprise cholesteric liquid crystals, as described above with respect to FIG. 18A. Accordingly, the BLA 2008 additionally includes a first quarter waveplate (QWP1) 1704, e.g., an achromatic quarter waveplate, configured to convert the light 1708-R, 1708-L outcoupled from the polarizing waveguide assembly 1712 into linear polarized light 1420 incident on the BLA 2008. Thus, the BLA 1008 operates in a similar manner as described above with respect to FIG. 19.

However, unlike the display device 2000 of FIG. 19, the display device 2000 does not have an FLA 2004 configured to cancel undesirable optical power exerted by the BLA 2008 to world-side light 1620 when the BLA 2008 exerts an optical power to light from the polarizing waveguide assembly 1712 containing virtual image information. Instead, when displaying the virtual image, the display device 2100 is configured to selectively focus light from the waveguide assembly 1712 while passing the world image substantially unaffected. This is achieved by replacing the FLA 2004 (FIG. 19) with a combination of a linear polarizer 1716 and a second quarter waveplate (QWP2) 1714, e.g., an achromatic quarter waveplate.

In some implementations, when displaying the world image, the display device 2100 does not exert substantial optical power. Under this configuration, light 1620 from the world, which is unpolarized, is linearly polarized, e.g., into horizontally linearly polarized (LHP) light by the linear polarizer 1716, which is subsequently converted to circularly polarized light by a second quarter wave plate (QWP2) 1714. The circularly polarized light incident on the polarizing waveguide assembly 1712 passes therethrough essentially unaffected, and is converted by the QWP1 1704 into linearly polarized light, e.g., LHP light. The BLA 1008, in which the switchable polarization-selective lens stack 1900A, is configured to exert substantially zero optical power by having its optical axis orthogonal to the polarization direction of the incident LHP light, thereby passing the incident light essentially unaffected to be seen by the eye 210.

Still referring to FIG. 20, when displaying virtual images, the BLA 2008 is configured to focus virtual images from waveguide assembly 1712 by exerting an optical power $\phi$ to linearly polarized light 1420 having LVP, from the waveguide assembly 1712, using the switchable polarization-selective lens stack 1900A. Since there is only one lens element in the BLA stack, the polarization state of the virtual images are unaltered and remain LVP and parallel to the optic axis of the switchable lens as described above with respect to FIG. 18. Thus, the world images are viewed undistorted by the user, while the virtual images receive a voltage dependent optical power $\phi(V)$ simultaneously.

Polarization-Selective Fresnel Lens Stack Comprising a Stack of Two One-Dimensional Fresnel Lenses Fabrication of polarization-selective Fresnel lens stacks such as that described above with respect to FIG. 13B can have many challenges. For example, because the grooves in the isotropic lens are circular, aligning LC molecules in a uniform horizontal direction may be difficult and/or costly. In the following, alternative designs of polarization-selective Fresnel lens stacks are described, which can be manufactured more easily by aligning LC molecules along grooves that are linear instead of being circular. For example, the groove can be are not rotationally symmetric. The grooves can be non-rotationally symmetric (e.g., cylindrical)

FIG. 21A illustrates a simplified design of a polarization-selective Fresnel lens stack comprising a one-dimensional (1D) polarization-selective Fresnel lens stack 2200A, according to some embodiments. Similar to the Fresnel lens stack described above with respect to FIG. 13B, the 1D polarization-selective Fresnel lens stack 2200A comprises a birefringent lens 2204 and an isotropic lens 2208. In addition, similar to the birefringent lens described above with respect to FIG. 13B, the LC molecules are aligned substantially in a horizontal direction 2212, e.g., y-direction, along grooves 2216 that form boundaries of Fresnel zones 2212. However, unlike the polarization-selective Fresnel lens stack having circular zones or grooves described above with respect to FIGS. 13A-13B, the 1D polarization-selective Fresnel lens stack 2200A is configured as a one-dimensional (1D) polarization-selective Fresnel lens stack, in which the grooves 2212 extend substantially parallel in a horizontal direction 2212, e.g., y-direction.

FIG. 21B illustrates a simplified design of a polarization-selective Fresnel lens stack comprising a two-dimensional (2D) polarization-selective Fresnel lens stack 2200B, according to some other embodiments. The polarization-selective Fresnel lens stack 2200B comprises a pair of 1D polarization-selective Fresnel lens stacks 2200A-1, 2200A-2, illustrated above with respect to FIG. 21A that are rotated by 90 degrees with respect to each other, and are interposed by a half wave plate (HWP) 2220, e.g., an achromatic HWP. Each of the pair of 1D polarization-selective Fresnel lens stacks 2200A-1, 2200A-2 comprises a birefringent lens 2204-1, 2204-2 and an isotropic lens 2208-1, 2208-2, respectively. In operation, the first 1D polarization-selective Fresnel lens stack 2200A-1 exerts a first lens power in a first lateral direction (x-direction) to linearly polarized incident light 1420 having the polarization direction parallel to the direction of grooves 2212 formed therein. Subsequently, the HWP 2220 rotates the linearly polarized light transmitted through the first 1D polarization-selective Fresnel lens stack 2200A-1 by 90° to align the polarization direction with the groove extension direction of second Fresnel lens stack 2200A-2, which exerts a second lens power in a second lateral direction (y-direction) to the linearly polarized light transmitted through the HWP 2220 and having the polarization direction parallel to the direction of grooves 2212 formed therein. As configured, the overall function of the two-dimensional (2D) polarization-selective Fresnel lens stack 2200B is comparable to that of the polarization-selective Fresnel lens stack described above with respect to FIG. 13B having circular symmetric grooves, except for possible additional aberrations due to increased number of grooves.

FIG. 21C illustrates a simplified design of a switchable polarization-selective Fresnel lens stack comprising a two-dimensional (2D) polarization-selective Fresnel lens stack 2200C, according to some other embodiments. The polarization-selective Fresnel lens stack 2200C comprises a pair of isotropic lenses 2208-1, 2208-2 that are rotated by 90° with respect to each other such that their grooves cross each other. The pair of isotropic lenses 2208-1, 2208-2 are interposed by a birefringent lens 2204 comprising RMs or switchable unpolymerized liquid crystal molecules. The LC molecules of the birefringent lens 2204 are configured such that the LC molecules adjacent the first isotropic lens 2208-1 are aligned in one lateral direction, e.g., y-direction, while the LC molecules adjacent the second isotropic lens 2208-1 are aligned in the other lateral direction, e.g., X-direction. The two-dimensional (2D) polarization-selective Fresnel lens stack 2200C additionally comprises a pair of transparent electrodes 1916, 1920 interposed by the isotropic lenses 2208-1, 2208-2 having the RMs formed therebetween. In operation, the LC molecules of the birefringent lens 2204 serves to provide a lens effect as well as serving as half wave plate, similar to the HWP 2220 of FIG. 21B. As configured, the overall function of the two-dimensional (2D) polarization-selective Fresnel lens stack 2200C is similar to that described above with respect to FIG. 21B.

Method of Fabricating Polarization-Selective Fresnel Lens Stack

FIGS. 22A-22D illustrate an example method for fabricating a polarization-selective Fresnel lens stack, according to embodiments.

FIG. 22A illustrates an intermediate structure 2300A comprising a template substrate 2304 formed by providing an isotropic material and forming therein grooves described above with respect to FIG. 13B via processes such as for example casting, molding or diamond cutting, to name a few. For fabricating a switchable polarization-selective Fresnel lens stack, a transparent electrode such as ITO (also metal nanowires, polyethylene dioxythiophene (PEDOT), etc.) may be conformally deposited on the template substrate 2304. Subsequently, a first LC alignment layer 2306 is formed on the template substrate 2304 via for example any of spin, slot, blade, spray coating techniques or combinations thereof, and then thermally baked (e.g., 100° C., 1 minute) to remove excess solvent.

FIG. 22B illustrates an intermediate structure 2300B formed by providing a second substrate 2308 and forming thereon a second LC alignment layer 2310 for example in a similar manner as described above with respect to FIG. 22A.

The substrates 2304 and 2308 can be formed of a transparent material including, e.g., an acrylic, a silicon dioxide, sapphire or any suitable transparent material.

The alignment layers 2306, 2310 can include a photoalignment layer on which, when LC molecules are deposited, the LC molecules may become oriented along a preferential direction, for example, due to anchoring energy exerted on the LC molecules by the photo-alignment layer. Examples of photo-alignment layers include polyimide, linear-polarization photopolymerizable polymer (LPP), azo-containing polymers, courmarine-containing polymers and cinnamate-containing polymers, to name a few.

The alignment layers 2306, 2310 may be formed by dissolving precursors, e.g., monomers, in a suitable solvent and coating the substrate with the solution using a suitable process, e.g., spin coating, slot coating, doctor blade coating, spray coating and jet (inkjet) coating, among other deposition processes. The solvent can thereafter be removed from the coated solution. The alignment layers 2306, 2310 may also be cured, e.g., UV cured, e.g., with a polarizer, in preparation for the subsequent alignment of the LC molecules thereon.

After coating, the alignment layers 2306, 2310 can be optically patterned or recorded. For example, the optical patterning can be performed using a linearly polarized light.

FIG. 22C illustrates an intermediate structure 2300C formed by bringing together the intermediate structures 2300A (FIG. 22A) and 2300B (FIG. 22B) such that the first and second LC alignment layers 2306 and 2310 face each other. In some embodiments, a plurality of spacers 2314 mixed with an adhesive may be disposed between the first and second LC alignment layers 2306 and 2310 to form a cell gap 2318. Thus formed intermediate structure 2300C comprising a sandwich structure is exposed to linearly polarized ultraviolet (UV) light to create a linear alignment pattern on both of the substrates 2304 and 2308 simultaneously. Alternatively, the alignment pattern can be formed using rubbed polyimide prior to creating the sandwich structure.

FIG. 22D illustrates an intermediate structure 2400D formed by filling the gap 2318 with unpolymerized LC material or reactive mesogens (RMs). The LC material may include a reactive mesogen mixture (including, e.g., liquid crystal monomers, solvents, photoinitiators, and surfactants).

Thereafter, thermal annealing, e.g., at 100° C., 1 minute, may be performed. For switchable polarization-selective Fresnel lens stacks, the process may end here. There are certain polymerizable LCs that can be filled in this manner (e.g., UCL-001 from DIC Corporation Japan Ltd.). Subsequently, to form passive a polarization-selective Fresnel lens stacks, the LC material or RMs are exposed to UC light to polymerize the LC material or RMs to form a passive polarization-selective Fresnel lens stack.

Other embodiments are possible. For example, instead of the gap-filling process described above, a LC polymer (LCP) layer may be coated directly on either or both of the substrates 2304, 2308 using a suitable process, including, e.g., spin coating, slot coating, doctor blade coating, spray coating and inkjet coating, among other deposition processes.

ADDITIONAL EXAMPLES

1. An adaptive lens assembly, comprising:
 a lens stack configured to exert polarization-dependent optical power to linearly polarized light,
 wherein the lens stack comprises a birefringent lens and an isotropic lens contacting each other to form a conformal interface therebetween,
 wherein the adaptive lens assembly is configured to be selectively switched between a plurality of states having different optical powers.

2. The adaptive lens assembly of Example 1, wherein
 the birefringent lens has an optic axis and a birefringence (Δn) and configured to exert a first optical power to light having a polarization direction parallel to the optic axis, and to exert a second optical power to light having a polarization direction perpendicular to the optic axis; and
 the isotropic lens has a refractive index and configured to exert to light passing therethrough a third optical power opposite in sign as the first optical power and the second optical power, 3. The adaptive lens assembly of Example 2, wherein the Δn corresponds to a difference between an extraordinary refractive index ($n_e$) in a direction parallel to the optic axis of the birefringent lens and an ordinary refractive index ($n_o$) in a direction perpendicular to the optic axis of the birefringent lens, and wherein the refractive index of the isotropic lens has substantially the same value as the $n_o$ of the birefringent lens.

4. The adaptive lens assembly of any one of the preceding Examples, wherein the third optical power is substantially the same in magnitude as the second optical power, such that the polarization-selective lens stack is configured to exert substantially no optical power to light having a polarization direction perpendicular to the optic axis.

5. The adaptive lens assembly of any one of the preceding Examples, wherein the lens stack is configured to exert an optical power proportional to the Δn to light having a polarization direction parallel to the optic axis.

6. The adaptive lens assembly of any one of the preceding Examples, wherein the birefringent lens is a Fresnel lens comprising a plurality grooves formed therein, and wherein adjacent ones of the grooves define a Fresnel zone of the Fresnel lens.

7. The adaptive lens assembly of Example 6, wherein the plurality of grooves comprise concentrically circular grooves.

8. The adaptive lens assembly of Example 6, wherein the plurality of grooves comprise parallel grooves extending in a direction parallel to a major surface of the lens stack.

9. The adaptive lens assembly of any one of the preceding Examples, wherein the birefringent lens comprises liquid crystals (LCs).

10. The adaptive lens assembly of Example 9, wherein LC molecules of the birefringent lens are substantially aligned in a lateral direction parallel to a major surface of the lens stack.

11. The adaptive lens assembly of any one of the preceding Examples, further comprising a switchable half waveplate comprising twisted nematic (TN) liquid crystals (LCs) optically coupled to the lens stack, wherein the switchable half waveplate is configured to preserve a polarization of linear polarized light passing therethrough when activated and to alter the polarization of linear polarized light passing therethrough when deactivated.

12. The adaptive lens assembly of any one of the preceding Examples, wherein the switchable half waveplate is disposed on a first side of the polarization-selective lens stack, the adaptive lens assembly further comprising on a second side of the polarization-selective lens stack:
a second switchable half waveplate comprising TN LCs optically coupled to the polarization-selective lens stack; and
a second lens stack configured to exert polarization-dependent optical power to linearly polarized light, wherein the second lens stack comprises a second birefringent lens and a second isotropic lens contacting each other to form a conformal interface therebetween,
wherein the adaptive lens assembly is configured to be selectively switched between at least four states by electrically activating and/or deactivating the switchable waveplate and/or the second switchable half waveplate.

13. The adaptive lens assembly of any one of Examples 1-10, wherein the birefringent lens comprises reactive mesogens, and wherein the lens stack comprises electrodes configured to apply an electric field across the birefringent lens such that the lens stack is configured to be electrically switchable between different optical power states.

14. A display device comprising:
a waveguide assembly configured to guide light in a lateral direction parallel to an output surface of the waveguide assembly, the waveguide assembly further configured to outcouple the guided light through the output surface; and
an adaptive lens assembly disposed on a first side of the waveguide assembly, the adaptive lens assembly disposed to receive outcoupled light from the waveguide assembly and to be selectively switched between a plurality of states having different optical powers,
wherein the adaptive lens assembly comprises a lens stack configured to exert polarization-dependent optical power to linearly polarized light, the lens stack comprising a birefringent lens and an isotropic lens contacting each other, wherein contacting surfaces of the birefringent lens and the isotropic lens form a conformal interface.

15. The display device of Example 14, wherein:
the birefringent lens has an optical axis and a birefringence (Δn) and is configured to exert a first optical power to light having a polarization direction parallel to the optic axis, and to exert a second optical power to light having a polarization direction perpendicular to the optic axis, and
the isotropic lens has a refractive index and is configured to exert to light passing therethrough a third optical power opposite in sign as at least one of the first optical power and the second optical power.

16. The display device of Example 15, wherein the birefringent lens is a Fresnel lens comprising a plurality grooves formed therein, and wherein adjacent ones of the grooves define a Fresnel zone.

17. The display device of Example 15, wherein the birefringent lens comprises liquid crystals (LCs), 18. The display device of Example 15, wherein LC molecules of the birefringent lens are substantially aligned in the same direction parallel to a major surface of the polarization-selective lens stack.

19. The display device of Example 14, further comprising:
a second adaptive lens assembly disposed on a second side of the waveguide assembly opposite the first side, the second adaptive lens assembly configured to be selectively switched between a plurality of states having different optical powers and comprising:
a second lens stack configured to exert polarization-dependent optical power to linearly polarized light, wherein the second lens stack comprises a second birefringent lens and a second isotropic lens contacting each other to form a conformal interface therebetween.

20. The display device of Example 19, wherein each of the first and second adaptive lens assemblies further comprises a switchable half waveplate comprising twisted nematic (TN) liquid crystals (LCs) optically coupled to a respective one of the lens stack or the second lens stack, wherein the switchable half waveplate is configured to preserve a polarization of linear polarized light passing therethrough when activated and to alter the polarization of linear polarized light passing therethrough when deactivated.

21. The display device of Example 20, wherein each of the plurality of optical powers exerted by the second adaptive lens assembly has a corresponding one of the plurality of optical powers exerted by the adaptive lens assembly having substantially the same magnitude and having an opposite sign.

22. The display device of any one of Examples 14-21, wherein the adaptive lens assembly is formed on a first side of the waveguide assembly, the display device further comprising a polarizing reflector interposed between the waveguide assembly and adaptive lens assembly, wherein the polarizing reflector is configured to pass therethrough linear polarized light having a first polarization to reflect linear polarized light having a second polarization.

23. The display device of Example 22, further comprising on a second side of the waveguide assembly a nonpolarizing reflector and a quarter waveplate interposed between the nonpolarizing reflector and the waveguide assembly, wherein the nonpolarizing reflector is configured to reflect and to alter the polarization of linear polarized light having the first polarization incident thereon.

24. The display device of any one of Examples 14-21, wherein the adaptive lens assembly is formed on a first side of the waveguide, the display device further comprising a polarizing reflector interposed between the adaptive lens assembly and the waveguide assembly, wherein the polarizing reflector comprises cholesteric liquid crystals configured such that the polarizing notch reflector is configured to pass therethrough circular polarized light having a first polarization and to reflect circular polarized light having a second polarization.

25. The display device of Example 24, further comprising on a second side of the waveguide assembly a nonpolarizing reflector, wherein the nonpolarizing reflector is configured to reflect and to alter the polarization of circular polarized light incident thereon having the second circular polarization.

26. The display device of Example 19, wherein each of the birefringent lens and the second birefringent lens comprises reactive mesogens, and wherein each of the lens stack and the second lens stack comprises electrodes configured to switch the each of the lens stack and the second lens stack between different optical power states.

27. The display device of Example 14, wherein the birefringent lens comprises reactive mesogens, and wherein the polarization-selective lens stack comprises electrodes for electrically switching the polarization-selective lens stack between at least two optical power states.

28. The display device of Example 27, further comprising on a second side opposite the first side of the waveguide assembly:
 a linear polarizer; and
 a quarter waveplate interposed between the waveguide assembly and the linear polarizer.

29. The display device any one of Examples 22-25 wherein the polarizing reflector comprises a polarizing notch reflector.

30. The display device any one of Examples 22-25 and 29, wherein the non-polarizing reflector comprises a non-polarizing notch reflector.

31. The display device any one of the Examples 14-30 disposed in a head mounted display.

32. The display device any one of Examples 14-31, further comprising a frame configured to be supported on a head of the user.

33. The display device of any one of Examples 14-32, wherein at least a portion of the display device is transparent and disposed at a location in front of a user's eye when the user wears the display device such that the transparent portion transmits light from a portion of the environment in front of the user and the display device to the user's eye to provide a view of the portion of the environment in front of the user and the display device.

34. The display device any one of Examples 14-33, wherein the display device is configured to project light into a user's eye to display virtual image content to the user's vision field at different amounts of at least one of divergence and collimation and thus the displayed virtual image content appears to originate from different depths at different periods of time.

35. The display device any one of Examples 14-34, wherein the adaptive lens assembly comprises a Fresnel lens.

36. The adaptive lens assembly of any one of Examples 1-13, wherein the lens stack comprises a Fresnel lens.

37. The adaptive lens assembly of any one of Examples 6 and 8-10, wherein grooves form abrupt discontinuities in the thickness of the birefringent lens.

38. The adaptive lens assembly of any one of Examples 6, 8-10, and 37, wherein the grooves comprises straight groove.

It will be appreciated that any one of the above examples may be combined with or used in the context of a wearable augmented reality head-mountable display system and/or a method of making or using the wearable augmented reality head-mountable display system. The head-mountable display may comprise one or more of the following: a light modulating system configured to output light to form an image, a head mountable frame, and/or one or more waveguides attached to the frame and configured to receive the light from the light modulating system.

ADDITIONAL CONSIDERATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. For example, referring to FIG. 15, it will be appreciated that one or more adaptive lens assemblies 1504-1 to 1504-3 may be disposed between individual ones of the waveguides 1012a, 1012b, and/or 1012c.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Accordingly, the claims are not intended to be limited to the embodiments shown herein, but are to be accorded the widest scope consistent with this disclosure, the principles and the novel features disclosed herein.

What is claimed is:

1. An adaptive lens assembly, comprising:
a lens stack configured to exert polarization-dependent optical power to linearly polarized light,
wherein the lens stack comprises a birefringent lens and an isotropic lens contacting each other to form a conformal interface therebetween,
wherein the adaptive lens assembly is configured to be selectively switched between a plurality of states having different optical powers,
wherein the birefringent lens has an optic axis and a birefringence ($\Delta n$) and is configured to exert a first optical power to light having a polarization direction parallel to the optic axis, and to exert a second optical power to light having a polarization direction perpendicular to the optic axis, and
wherein the isotropic lens has a refractive index and is configured to exert to light passing therethrough a third optical power opposite in sign as the first optical power and the second optical power.

2. The adaptive lens assembly of claim 1, wherein the $\Delta n$ corresponds to a difference between an extraordinary refractive index (ne) in a direction parallel to the optic axis of the birefringent lens and an ordinary refractive index (no) in a direction perpendicular to the optic axis of the birefringent lens, and wherein the refractive index of the isotropic lens has substantially the same value as the no of the birefringent lens.

3. The adaptive lens assembly of claim 1, wherein the third optical power is substantially the same in magnitude as the second optical power, such that the lens stack is configured to exert substantially no optical power to light having a polarization direction perpendicular to the optic axis.

4. The adaptive lens assembly of claim 1, wherein the lens stack is configured to exert an optical power proportional to the $\Delta n$ to light having a polarization direction parallel to the optic axis.

5. The adaptive lens assembly of claim 1, wherein the birefringent lens is a Fresnel lens comprising a plurality grooves formed therein, and wherein adjacent ones of the grooves define a Fresnel zone of the Fresnel lens.

6. The adaptive lens assembly of claim 5, wherein the plurality of grooves comprise concentrically circular grooves.

7. The adaptive lens assembly of claim 5, wherein the plurality of grooves comprise parallel grooves extending in a direction parallel to a major surface of the lens stack.

8. The adaptive lens assembly of claim 5, wherein the grooves form abrupt discontinuities in the thickness of the birefringent lens.

9. The adaptive lens assembly of claim 5, wherein the grooves comprises straight groove.

10. The adaptive lens assembly of claim 1, wherein the birefringent lens comprises liquid crystals (LCs).

11. The adaptive lens assembly of claim 10, wherein LC molecules of the birefringent lens are substantially aligned in a lateral direction parallel to a major surface of the lens stack.

12. The adaptive lens assembly of claim 1, wherein the lens stack comprises a Fresnel lens.

13. An adaptive lens assembly, comprising:
a lens stack configured to exert polarization-dependent optical power to linearly polarized light,
wherein the lens stack comprises a birefringent lens and an isotropic lens contacting each other to form a conformal interface therebetween, and
wherein the adaptive lens assembly is configured to be selectively switched between a plurality of states having different optical powers; and
a switchable half waveplate comprising twisted nematic (TN) liquid crystals (LCs) optically coupled to the lens stack, wherein the switchable half waveplate is configured to preserve a polarization of linear polarized light passing therethrough when activated and to alter the polarization of linear polarized light passing therethrough when deactivated.

14. The adaptive lens assembly of claim 13, wherein the switchable half waveplate is disposed on a first side of the lens stack, the adaptive lens assembly further comprising on a second side of the lens stack:
a second switchable half waveplate comprising TN LCs optically coupled to the lens stack; and
a second lens stack configured to exert polarization-dependent optical power to linearly polarized light, wherein the second lens stack comprises a second birefringent lens and a second isotropic lens contacting each other to form a conformal interface therebetween, wherein the adaptive lens assembly is configured to be selectively switched between at least four states by electrically activating and/or deactivating the switchable waveplate and/or the second switchable half waveplate.

15. An adaptive lens assembly, comprising:
a lens stack configured to exert polarization-dependent optical power to linearly polarized light,
wherein the lens stack comprises a birefringent lens and an isotropic lens contacting each other to form a conformal interface therebetween, and
wherein the adaptive lens assembly is configured to be selectively switched between a plurality of states having different optical powers,
wherein the birefringent lens comprises reactive mesogens, and
wherein the lens stack comprises electrodes configured to apply an electric field across the birefringent lens such that the lens stack is configured to be electrically switchable between different optical power states.

16. A display device comprising:
a waveguide assembly configured to guide light in a lateral direction parallel to an output surface of the waveguide assembly, the waveguide assembly further configured to outcouple the guided light through the output surface; and
an adaptive lens assembly disposed on a first side of the waveguide assembly, the adaptive lens assembly disposed to receive outcoupled light from the waveguide assembly and to be selectively switched between a plurality of states having different optical powers,
wherein the adaptive lens assembly comprises a lens stack configured to exert polarization-dependent optical power to linearly polarized light, the lens stack comprising a birefringent lens and an isotropic lens contacting each other, wherein contacting surfaces of the birefringent lens and the isotropic lens form a conformal interface,
wherein the birefringent lens has an optical axis and a birefringence ($\Delta n$) and is configured to exert a first optical power to light having a polarization direction parallel to the optic axis, and to exert a second optical power to light having a polarization direction perpendicular to the optic axis, and
wherein the isotropic lens has a refractive index and is configured to exert to light passing therethrough a third optical power opposite in sign as at least one of the first optical power and the second optical power.

17. The display device of claim 16, wherein the birefringent lens is a Fresnel lens comprising a plurality grooves formed therein, and wherein adjacent ones of the grooves define a Fresnel zone.

18. The display device of claim 16, wherein the birefringent lens comprises liquid crystals (LCs).

19. The display device of claim 16, wherein LC molecules of the birefringent lens are substantially aligned in the same direction parallel to a major surface of the lens stack.

20. The display device of claim 16, wherein the display device is disposed in a head mounted display.

21. The display device of claim 20, further comprising a frame configured to be supported on a head of the user.

22. The display device of claim 20, wherein at least a portion of the display device is transparent and disposed at a location in front of a user's eye when the user wears the display device such that the transparent portion transmits light from a portion of the environment in front of the user and the display device to the user's eye to provide a view of the portion of the environment in front of the user and the display device.

23. The display device of claim 16, wherein the adaptive lens assembly comprises a Fresnel lens.

24. A display device comprising:
a waveguide assembly configured to guide light in a lateral direction parallel to an output surface of the waveguide assembly, the waveguide assembly further configured to outcouple the guided light through the output surface;
an adaptive lens assembly disposed on a first side of the waveguide assembly, the adaptive lens assembly disposed to receive outcoupled light from the waveguide assembly and to be selectively switched between a plurality of states having different optical powers,
wherein the adaptive lens assembly comprises a lens stack configured to exert polarization-dependent optical power to linearly polarized light, the lens stack comprising a birefringent lens and an isotropic lens contacting each other, wherein contacting surfaces of the birefringent lens and the isotropic lens form a conformal interface; and
a second adaptive lens assembly disposed on a second side of the waveguide assembly opposite the first side, the second adaptive lens assembly configured to be selectively switched between a plurality of states having different optical powers and comprising:
a second lens stack configured to exert polarization-dependent optical power to linearly polarized light, wherein the second lens stack comprises a second birefringent lens and a second isotropic lens contacting each other to form a conformal interface therebetween.

25. The display device of claim 24, wherein each of the first and second adaptive lens assemblies further comprises a switchable half waveplate comprising twisted nematic (TN) liquid crystals (LCs) optically coupled to a respective one of the lens stack or the second lens stack, wherein the switchable half waveplate is configured to preserve a polarization of linear polarized light passing therethrough when activated and to alter the polarization of linear polarized light passing therethrough when deactivated.

26. The display device of claim 25, wherein each of the plurality of optical powers exerted by the second adaptive lens assembly has a corresponding one of the plurality of optical powers exerted by the adaptive lens assembly having substantially the same magnitude and having an opposite sign.

27. The display device of claim 24, wherein each of the birefringent lens and the second birefringent lens comprises reactive mesogens, and wherein each of the lens stack and the second lens stack comprises electrodes configured to switch the each of the lens stack and the second lens stack between different optical power states.

28. A display device comprising:
a waveguide assembly configured to guide light in a lateral direction parallel to an output surface of the waveguide assembly, the waveguide assembly further configured to outcouple the guided light through the output surface;
an adaptive lens assembly disposed on a first side of the waveguide assembly, the adaptive lens assembly disposed to receive outcoupled light from the waveguide assembly and to be selectively switched between a plurality of states having different optical powers, wherein the adaptive lens assembly comprises a lens stack configured to exert polarization-dependent optical power to linearly polarized light, the lens stack comprising a birefringent lens and an isotropic lens contacting each other, wherein contacting surfaces of the birefringent lens and the isotropic lens form a conformal interface; and a polarizing reflector interposed between the waveguide assembly and the adaptive lens assembly, wherein the polarizing reflector is configured to pass therethrough linear polarized light having a first polarization to reflect linear polarized light having a second polarization.

29. The display device of claim 28, further comprising on a second side of the waveguide assembly a nonpolarizing reflector and a quarter waveplate interposed between the nonpolarizing reflector and the waveguide assembly, wherein the nonpolarizing reflector is configured to reflect and to alter the polarization of linear polarized light having the first polarization incident thereon.

30. The display device of claim 28, wherein the polarizing reflector comprises a polarizing notch reflector.

31. The display device of claim 28, wherein the nonpolarizing reflector comprises a non-polarizing notch reflector.

32. A display device comprising:
a waveguide assembly configured to guide light in a lateral direction parallel to an output surface of the waveguide assembly, the waveguide assembly further configured to outcouple the guided light through the output surface;
an adaptive lens assembly disposed on a first side of the waveguide assembly, the adaptive lens assembly disposed to receive outcoupled light from the waveguide assembly and to be selectively switched between a plurality of states having different optical powers,
wherein the adaptive lens assembly comprises a lens stack configured to exert polarization-dependent optical power to linearly polarized light, the lens stack comprising a birefringent lens and an isotropic lens contacting each other, wherein contacting surfaces of the birefringent lens and the isotropic lens form a conformal interface; and
a polarizing reflector interposed between the adaptive lens assembly and the waveguide assembly, wherein the polarizing reflector comprises cholesteric liquid crystals configured such that the polarizing notch reflector is configured to pass therethrough circular polarized light having a first polarization and to reflect circular polarized light having a second polarization.

33. The display device of claim 32, further comprising on a second side of the waveguide assembly a nonpolarizing reflector, wherein the nonpolarizing reflector is configured to reflect and to alter the polarization of circular polarized light incident thereon having the second circular polarization.

34. A display device comprising:
a waveguide assembly configured to guide light in a lateral direction parallel to an output surface of the waveguide assembly, the waveguide assembly further configured to outcouple the guided light through the output surface; and
an adaptive lens assembly disposed on a first side of the waveguide assembly, the adaptive lens assembly disposed to receive outcoupled light from the waveguide assembly and to be selectively switched between a plurality of states having different optical powers,
wherein the adaptive lens assembly comprises a lens stack configured to exert polarization-dependent optical power to linearly polarized light, the lens stack comprising a birefringent lens and an isotropic lens contacting each other, wherein contacting surfaces of the birefringent lens and the isotropic lens form a conformal interface, wherein the birefringent lens comprises reactive mesogens, and wherein the lens stack comprises electrodes for electrically switching the lens stack between at least two optical power states.

35. The display device of claim 34, further comprising on a second side opposite the first side of the waveguide assembly:
a linear polarizer; and
a quarter waveplate interposed between the waveguide assembly and the linear polarizer.

36. A display device comprising:
a waveguide assembly configured to guide light in a lateral direction parallel to an output surface of the waveguide assembly, the waveguide assembly further configured to outcouple the guided light through the output surface; and
an adaptive lens assembly disposed on a first side of the waveguide assembly, the adaptive lens assembly disposed to receive outcoupled light from the waveguide assembly and to be selectively switched between a plurality of states having different optical powers,
wherein the adaptive lens assembly comprises a lens stack configured to exert polarization-dependent optical power to linearly polarized light, the lens stack comprising a birefringent lens and an isotropic lens contacting each other, wherein contacting surfaces of the birefringent lens and the isotropic lens form a conformal interface,
wherein the display device is disposed in a head mounted display, and
wherein the display device is configured to project light into a user's eye to display virtual image content to the user's vision field at different amounts of at least one of divergence and collimation and thus the displayed virtual image content appears to originate from different depths at different periods of time.

* * * * *

UNITED STATES PATENT AND TRADEMARK OFFICE
CERTIFICATE OF CORRECTION

Page 1 of 1

PATENT NO. : 11,656,462 B2
APPLICATION NO. : 16/978165
DATED : May 23, 2023
INVENTOR(S) : Ravi Kumar Komanduri et al.

It is certified that error appears in the above-identified patent and that said Letters Patent is hereby corrected as shown below:

In the Claims

Column 51, Claim 1, Line 61:
The wording "(Dn)" should read: --($\Delta$n)--.

Column 52, Claim 2, Line 3:
The wording "(Dn)" should read: --($\Delta$n)--.

Column 52, Claim 4, Line 18:
The wording "(Dn)" should read: --($\Delta$n)--.

Column 53, Claim 16, Line 42:
The wording "(Dn)" should read: --($\Delta$n)--.

Signed and Sealed this
First Day of April, 2025

Coke Morgan Stewart
*Acting Director of the United States Patent and Trademark Office*